Figure 1A:
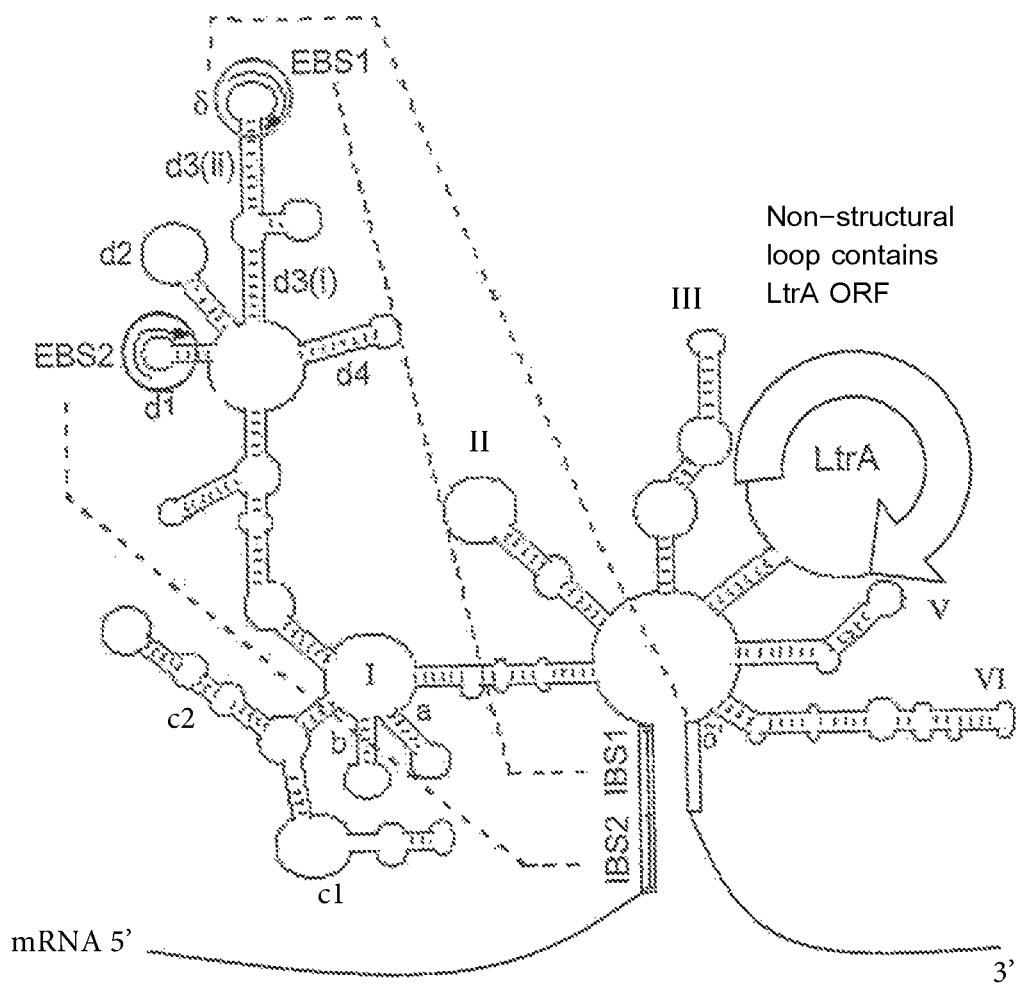

US010544422B2

(12) United States Patent
Minton et al.

(10) Patent No.

(56) References Cited

OTHER PUBLICATIONS

Cousineau et al (Apr. 27, 2000) *Nature* 404; 1018-1021.
Dai et al (2002) *Nucleic Acids Research* 30; 1091-1102.
Davis et al (2000) *J. Mol. Microbiol. Biotechnol.* 2; 59-69.
Davis et al (2005) Gene Cloning in *Clostridia*. Chaprer 3 In: Handbook on *Clostridia*(Dürre P, ed) pp. 37-52, CRC Press, Boca Raton, USA.
Desai et al (2004, e-pub. Mar. 6, 2004) *Appl Microbiol Biotechnol.* 65; 600-605.
Ehrenman et al (Aug. 1986) *Proc. Natl. Acad. Sci. USA* 83; 5875-5879.
Fox et al (1996) *Gene Ther.* 3; 173-178.
Frazier et al (Feb. 2003) *Appl. Environ. Microbiol.* 69; 1121-1128.
Freeman et al. (2001) *J. Antimicrob. Chemother.* 47; 244-246.
Geissendorfer et al (1990) *Appl. Microbiol. Biotechnol.* 33; 657-663.
GenBank Accession No. AE001437, last updated Jun. 10, 2010, located at <http://www.ncbi.nlm.nih.gov/nuccore/25168256>, last visited on Jan. 11, 2011, 296 pages.
GenBank Accession No. AM180355, last updated May 13, 2009, located at <http://www.ncbi.nlm.nih.gov/nuccore/115249003>, last visited on Jan. 11, 2011, 228 pages.
GenBank Accession No. AE015927, last updated Mar. 10, 2010, located at <http://www.ncbi.nlm.nih.gov/nuccore/28204652>, last visited on Jan. 11, 2011, 370 pages.
GenBank Accession No. BA000016, last updated May 19, 2007, located at <http://www.ncbi.nlm.nih.gov/nuccore/47118322>, last visited on Jan. 11, 2011, 456 pages.
Gilbert et al (1986) *J. Gen. Microbiol.* 132; 151-160.
Girbal et al (Aug. 2003) *Appl. Environ. Microbiol.* 69; 4985-4988.
Green et al (1996) *Appl. Biochem. Biotechnol.* 57-58; 213-221.
Green et al (1996) *Microbiol.* 142; 2079-2086.
Guo et al (Jul. 21, 2000) *Science* 289; 452-457.
Harris et al (Jul. 2002) *J. Bacteriol.* 184; 3586-3597.
Hasselmayer et al (2004) *Anaerobe* 10; 85-92.
Heap et al (2007) "The ClosTron: A universal gene knock-out system for the genus *Clostridium*," *Journal of Microbiological Methods* 70(3); 452-464.
Hensel et al (Jul. 21, 1995) *Science* 269; 400-403.
Horton et al (1990) *Biotechniques* 8(5); 528-535.
Houlihan et al. (2003) "The Susceptibility of Ionophore-Resistant Clostridium aminophilum F to other Antibiotics," *Journal of Antimicrobial Chemotherapy* 52: 623-628.
Ichiyanagi et al (2002) *Mol. Microbiol.* 46; 1259-1272.
Ichiyanagi et al (Dec. 23, 2003) "A bacterial group II intron favours retrotransposition into plasmid targets," *Proc. Natl. Acad. Sci. USA* 100; 15742-15747.
Jennert et al (2000) *Microbiology* 146; 3071-3080.
Ji et al (Sep. 21, 2001) *Science* 293; 2266-2269.
Jones et al (Dec. 1986) *Microbiol Rev.* 50; 484-524.
Karberg et al (Dec. 2001) "Group II introns as controllable gene targeting vectors for genetic manipulation of bacteria," *Nature Biotechnology* 19; 1162-1167.
Karunakaran et al (1999) *FEMS Microbiol. Letts.* 180; 221-227.
Kayser et al (Date Unknown). "Disruption of bacterial genes using retargeted group II introns," located at <http://www.sigmaaldrich.com/sigma/general%20information/targetronedinburghposter.pdf>, last visited on Jan. 11, 2011, 1 page.
Kuehne, S.A. et al. (Oct. 7, 2010). "The Role of Toxin A and Toxin B in *Clostridium difficile* Infection," *Nature* 467:711-714.
Kuehne et al. (2012) "ClosTron-Mediated Engineering of Clostridium," *Bioengineered* 3:4 247-254.
Lambowitz et al (2004, e-pub. May 25, 2004) *Annu. Rev. Genet.* 38; 1-35.
Lemmon et al (1997) *Gene Therapy* 4; 791-796.
Liu et al (2002) *Gene Therapy* 9; 291-296.
Liyanage et al (May 2001) *Appl. Environ. Microbiol.* 67; 2004-2010.

Mellaert et al. (2005). "Clostridia as Production Systems for Prokaryotic and Eukaryotic Proteins of Therapeutic Value in Tumor Treatment," in *Handbook on Clostridia*, Taylor & Francis Group, LLC, pp. 877-893.
Melville et al (Dec. 1994) *Infection and Immunity* 62; 5550-5558.
Miller et al (Mar. 2002) *Infect. Control Hosp. Epidemiol.* 23; 137-140.
Minton et al (1981) *J Gen Microbiol.* 127; 325-331.
Minton et al (1990) "Vector systems for the genetic analysis of *Clostridium acetobutylicum*," Chatper 38 In: *Anaerobes in Human Medicine and Industry* (eds P Boriello & J Hardie), Wrightson Publishing, Petersfield, UK pp. 187-201.
Minton (Dec. 2003) *Nat. Rev. Microbiol.* 1; 237-242.
Mohr et al (2000) *Genes & Development* 14; 559-573.
Mullany et al (1994) *Plasmid* 31; 320-323.
Muller et al (1996) *J Mol Biol.* 257; 21-29.
Mylonakis et al (Feb. 26, 2001) *Arch. Intern Med.* 161; 525-533.
Nair et al (Jan. 1999) *J. Bacteriol.* 181; 319-330.
O'Connor et al (2006) *Mol. Microbiol.* 61; 1335-1351.
Oultram et al (1988) *FEMS Microbiol Letts.* 56; 83-88.
Paredes et al (2005, e-pub. Oct. 24, 2005) *Nat. Rev. Microbiol.* 3; 969-978.
Pépin et al (Aug. 31, 2004) *CMAJ.* 171; 466-472.
Pépin et al (Nov. 1, 2005) *Clin. Infect Dis.* 41; 1254-1260.
Perelle et al (Apr. 1997) *Infect Immun.* 65; 1402-1407.
Perutka et al (2004) *J. Mol. Biol.* 336; 421-439.
Purdy et al (2002) *Mol. Microbiol.* 46; 439-452.
Riley (1998) *Eur. J. Clin. Microbiol. Infect Dis.* 17; 137-141.
Roberts et al (Feb. 2001) *J. Bacteriol.* 183; 1296-1299.
Roberts et al (2001) *Microbiol.* 147; 1243-1251.
Roberts, (2002) PhD thesis: *Investigation into the Molecular Genetics of the Conjugative Transposon Tn5397*, Chapter 5, University College London, 19 pages.
Roberts et al (2003) *J Microbiol Methods* 55; 617-624.
Roberts, A.P. et al. (2011, e-pub. Jul. 4, 2011). "Tn916-like Genetic Elements: A Diverse Group of Modular Mobile Elements Conferring Antibiotic Resistance," *FEMS Microbiol Rev* 35:856-871.
Roman et al (Mar. 1998) *Proc. Natl. Acad. Sci USA* 95(5); 2134-2139.
Saldanha et al (1999, e-pub. Jun. 22, 1999) *Biochemistry* 38; 9069-9083.
Sandegren et al (May 21, 2004) *J. Biol. Chem.* 279; 22218-22227.
Schneider et al (2003) "Iclaprim, a novel diaminopyrimidine with potent activity on trimethoprim sensitive and resistant bacteria," *Bioorganic & Med. Chem. Letts.* 13; 4217-4221.
Shimizu et al (Mar. 1994) *J. Bacteriol.* 176; 1616-1623.
Sigma Aldrich (2006). "TargeTron$^{TM}$, Gene Knockout System. User Guide," Catalog No. TA0100, 20 pages.
Sigma-Aldrich (2010). "Functional Genomics & RNAi. Multiple Knockouts" located at <http://www.sigmaaldrich.com/life-science/functional-genomics-and-rnai/targetron/targetron-vectors/multiple-knockouts.html>, last visited on Jan. 11, 2011, 2 pages.
Sigma-Aldrich (2010). "Functional Genomics RNAi. TargeTron Resources," located at <http://www.sigmaaldrich.com/life-science/functional-genomics-and-rnai/targetron/targetron-resources.html>, last visited on Jan. 11, 2011, 3 pages.
Sigma-Aldrich (2010). "Functional Genomics RNAi. FAQ," located at <http://www.sigmaaldrich.com/life-science/functional-genomics-and-rnai/targetron/faq.html>, last visited on Jan. 11, 2011, 2 pages.
Sigma-Aldrich (2010). "Functional Genomics RNAi. Other Organisms FAQ," located at <http://www.sigmaaldrich.com/life-science/functional-genomics-and-rnai/targetron/other-organisms-faq.html>, last visited on Jan. 11, 2011, 2 pages.
Sigma-Aldrich (2010). "Functional Genomics RNAi. *Staphylococcus*," located at <http://www.sigmaaldrich.com/life-science/functional-genomics-and-rnai/targetron/targetron-vectors/staphylococcus.html>, last visited on Jan. 11, 2011, 1 page.
Sigma Genosys (Date Unknown). "TargeTron Gene Knockout System," located at <http://www.sigma-genosys.com/targetron/>, last visited on Jan. 11, 2011, 1 page.
Sloan et al (1992) *Plasmid* 27; 207-219.

(56) References Cited

OTHER PUBLICATIONS

Spigaglia, P. et al. (Dec. 2005). "Horizontal Transfer of Erythromycin Resistance from *Clostridium difficile* to *Butyrivibrio fibrisolvens*," *Antimicrobial Agents and Chemotherapy* 49(12):5142-5145.
Swenson et al (Jul. 1980) *Antimicrob. Agents Chemother*. 18; 13-19.
Swinfield et al (1990) *Gene* 87; 79-90.
Takamizawa et al (2004, e-pub. May 14, 2004) *Protein Expression Purification* 36; 70-75.
Tasteyre et al (Dec. 2001) *Infect Immun*. 69; 7937-7940.
Thomas et al (2005) "Metabolic engineering of soventogenic clostridia," Chapter 37 In: Dürre, P. Handbook on Clostridia, CRC Press. pp. 813-830.
Tummala et al (Sep. 1999) *App. Environ. Microbiol*. 65; 3793-3799.
Tummala et al (Mar. 2003) *J. Bacteriol*. 185; 1923-1934.
Tummala et al (Jun. 2003). *J. Bateriol*. 185; 3644-3653.
Waligora et al (Apr. 2001) *Infect Immun*. 69; 2144-2153.
Wilcox et al (1996) *J. Hosp. Infect*. 34; 23-30.
Wilkinson et al (1994) *Microbiol*. 140; 89-95.
Williams et al (1990) "Development and optimisation of conjugative plasmid transfer from *Escherichia coli* to *Clostridium acetobutylicum* NCIB 8052," Chapter 43 In: *Clinical and Molecular Aspects of Anaerobes*,. Wrightson Biomedical Publishing Ltd. pp. 239-246.
Williams et al (1990) *J Gen Microbiol*. 136; 819-826.
Winzer et al (2000) *J. Mol. Microbiol. Biotechnol*. 2; 531-541.
Yao et al (2005) "Gene targeting using randomly inserted group II introns (targetrons) recovered from an *Escherichia coli* gene disruption library," *Nucleic Acids Research* 33; 3351-3362.
Yao et al (2006) "Use of targetrons to disrupt essential and nonessential genes in *Staphylococcus aureus* reveals temperature sensitivity of L1.LtrB group II intron splicing," *RNA* 12(7); 1271-1281.
Zhong et al (2003) "Targeted and random bacterial gene disruption using a group II intron (targetron) vector containing a retrotransposition-activated selectable marker," *Nucleic Acids Research* 31; 1656-1664.
Zimmerly et al (2001) *Nucleic Acids Res*. 29; 1238-1250.
Zimmerly Lab (Date Unknown). "General Introduction," located at <http://www.fp.ucalgary.ca/group2introns/generalintroduction.htm>, last visited on Jan. 11, 2011, 1 page.
Zimmerly Lab (Date Unknown). "Where are Group II Introns Found?" located at <http://www.fp.ucalgary.ca/group2introns/wherefound.htm>, last visited on Jan. 11, 2011, 1 page.
Zimmerly Lab (Jul. 23, 2008). "Welcome to the Zimmerly Lab Web Site for Mobile Group II INtrons," located at <http://www.fp.ucalgary.ca/group2introns/>, last visited on Jan. 11, 2011, 1 page.
Lee, S.Y. et al. (1993). "Determination in Clostridium of Plasmid Copy Number and Acetobutylicum ATCC 824," FEMS Microbiology Letters 108:319-324.

\* cited by examiner

Secondary Structure Model of Ll.LtrB Intron

Transcription of the selectable marker gene produces non-functional mRNA interrupted by *td*

Transcription of selectable marker gene produces a functional mRNA

- cells exhibit selectable phenotype
- re-targeting of the group II intron can be positively selected

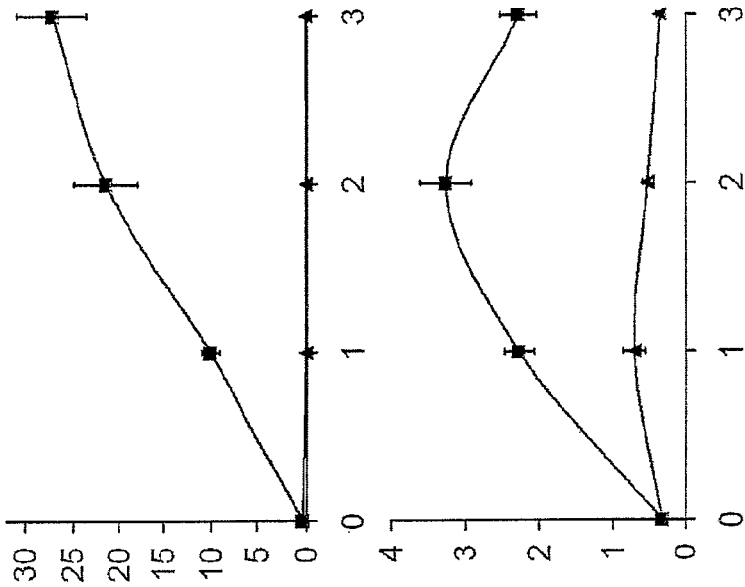
Fig. 3B
Fig. 3C
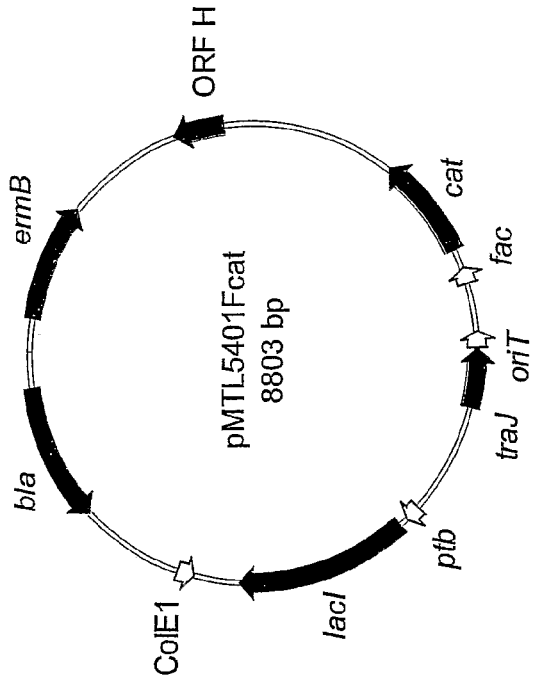
Fig. 3A

Frame 1
Amino acid sequence -   D     P     R     D/E
Nucleotide sequence -   GAC   CCA   AGA   GA Frame 2
Amino acid sequence -   R/G   P     K     R
Nucleotide sequence -   GA    CCC   AAG   AGA Frame 3
Amino acid sequence -   'X'   T     Q     E     'Z'
Nucleotide Sequence -   G     ACC   CAA   GAG   A

Fig. 4

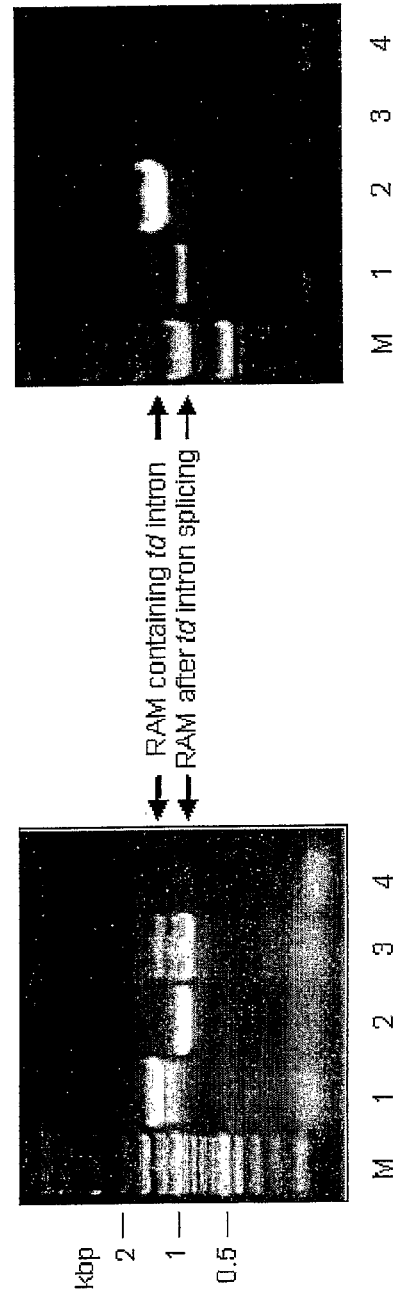
Fig. 5A
Fig. 5B
Fig. 5C

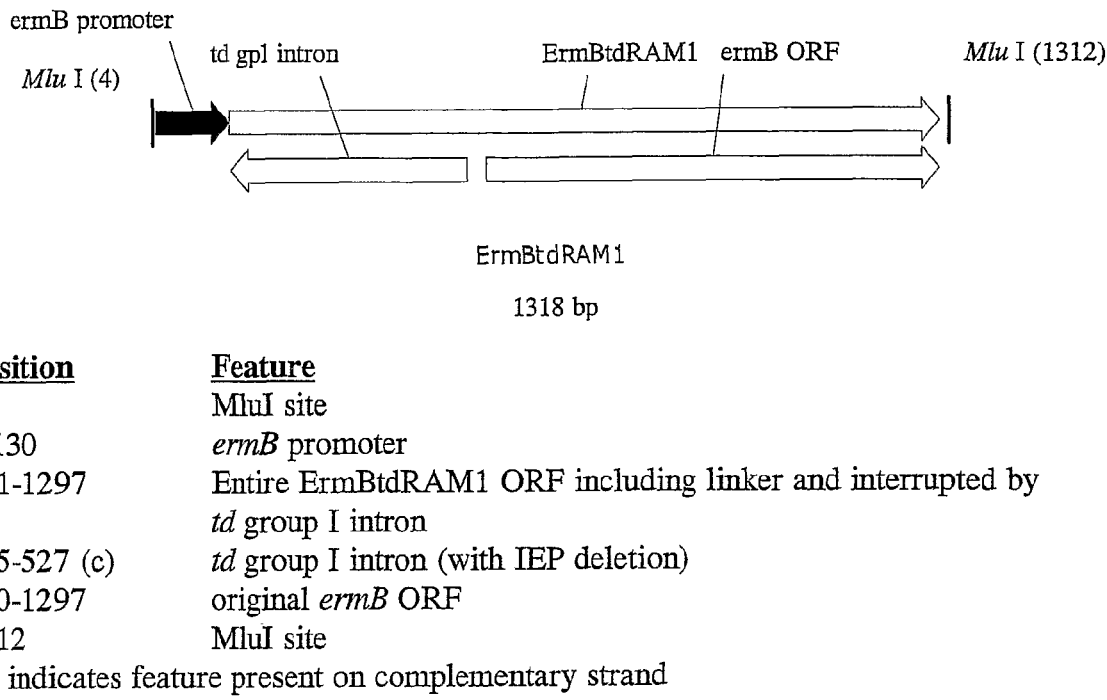

| Position | Feature |
|---|---|
| 4 | MluI site |
| 9-130 | *ermB* promoter |
| 131-1297 | Entire ErmBtdRAM1 ORF including linker and interrupted by *td* group I intron |
| 135-527 (c) | *td* group I intron (with IEP deletion) |
| 560-1297 | original *ermB* ORF |
| 1312 | MluI site |

(c) indicates feature present on complementary strand

ErmBtdRAM1 sequence:
```
CTACGCGTGG AAATAAGACT TAGAAGCAAA CTTAAGAGTG TGTTGATAGT GCAGTATCTT  60
AAAATTTTGT ATAATAGGAA TTGAAGTTAA ATTAGATGCT AAAAATTTGT AATTAAGAAG 120
GAGTGATTAC ATGGCATTAT GTTCAGATAA GGTCGTTAAT CTTACCCCGG AATTATATCC 180
AGCTGCATGT CACCATGCAG AGCAGACTAT ATCTCCAACT TGTTAAAGCA AGTTGTCTAT 240
CGTTTCGAGT CACTTGACCC TACTCCCCAA AGGGATAGTC GTTAGGCATT TATGTAGAAC 300
CAATTCCATT TATCAGATTT TACACGATAA GTAACTAATC CAGACGAAAT TTTCTCTAGA 360
GAAAGTATTT TTAATCTGAT AAATTCCGCT TTTCATAAAT ACCTCTTTAA ATATAGAAGT 420
ATTTATTAAA GGGCAGTCCT ACAATTTAGC ACGGGATTGT CTACTAGAGA GGTTCCCCGT 480
TTAGATAGAT TACAAGTATA AGTCACCTTA TACTCAGGCC TCAATTAACC CAAGAGATGC 540
TGGTGCTTCT GGTGCTGGTA TGAACAAAAA TATAAAATAT TCTCAAAACT TTTTAACGAG 600
TGAAAAAGTA CTCAACCAAA TAATAAAACA ATTGAATTTA AAAGAAACCG ATACCGTTTA 660
CGAAATTGGA ACAGGTAAAG GGCATTTAAC GACGAAACTG GCTAAAATAA GTAAACAGGT 720
AACGTCTATT GAATTAGACA GTCATCTATT CAACTTATCG TCAGAAAAAT TAAAACTGAA 780
TACTCGTGTC ACTTTAATTC ACCAAGATAT TCTACAGTTT CAATTCCCTA ACAAACAGAG 840
GTATAAAATT GTTGGGAGTA TTCCTTACCA TTTAAGCACA CAAATTATTA AAAAGTGGT 900
TTTTGAAAGC CATGCGTCTG ACATCTATCT GATTGTTGAA GAAGGATTCT ACAAGCGTAC 960
CTTGGATATT CACCGAACAC TAGGGTTGCT CTTGCACACT CAAGTCTCGA TTCAGCAATT 1020
GCTTAAGCTG CCAGCGGAAT GCTTTCATCC TAAACCAAAA GTAAACAGTG TCTTAATAAA 1080
ACTTACCCGC CATACCACAG ATGTTCCAGA TAAATATTGG AAGCTATATA CGTACTTTGT 1140
TTCAAAATGG GTCAATCGAG AATATCGTCA ACTGTTTACT AAAAATCAGT TTCATCAAGC 1200
AATGAAACAC GCCAAAGTAA ACAATTTAAG TACCGTTACT TATGAGCAAG TATTGTCTAT 1260
TTTTAATAGT TATCTATTAT TTAACGGGAG GAAATAATTC TATGAGTCGC ACGCGTTC   1318
```

Fig. 6 pBRR3-LtrB

AatII                           LtrB VT exons                                    EcoRI CCGACGT CACCCACGTC GATCGTGGAC ACATCCATAA CCATATCATT TTTAATGAAT TCTAA
GGCTGCA GTGGGTGCAG CTAGCACTTG TGTAGGTATT GGTATAGTAA AAATTACTTA AGATT pCR2.1-TOPO

SacI     SpeI                           EcoRI                                   NotI    XhoI               NsiI

...TG GTATCGAGCT CGGTACCCGG GGATCCTCTA GAATGCATGC TCGAGCGGCC GCACTAGTGA TCATATGACA TCATGTATAT CTCCTTCTTA AAGTT pBRR3-MCS1

AatII      XhoI   KpnI            NsiI          SpeI                   EcoRI      NotI

CCGACGT CTCGAGGT CATGCATAGG CCTGAGCTCA CTACTAGTGC GGCCGCGGAATTCT
GGCTGCA GAGCTCCATG GTACGTATCC GGACTCGAGT GATGATCACG CCGGCTTAAGA

Multicloning site fragment

-----CTCGAGGTACCATGCATAGGCCTGAGCTCACTAGTGCGGCCGCG-----
-----TGCAGAGCTCCATGGTACGTATCCGGACTCGAGTGATCACGCCGGCTTAA-

Fig. 8

```
WT thl promoter:      TTGATAAAAATAATAATAGTGGGTATAAT
                      ||||x|-------17bp------||||||
Consensus:            TTGACA-------17bp------TATAAT
                      ||xxx|-------16bp------||x|||
Mutant thl2           TTccTA-AAATAATAATAGTGGGTAaAAT
promoter:
```

Fig. 9

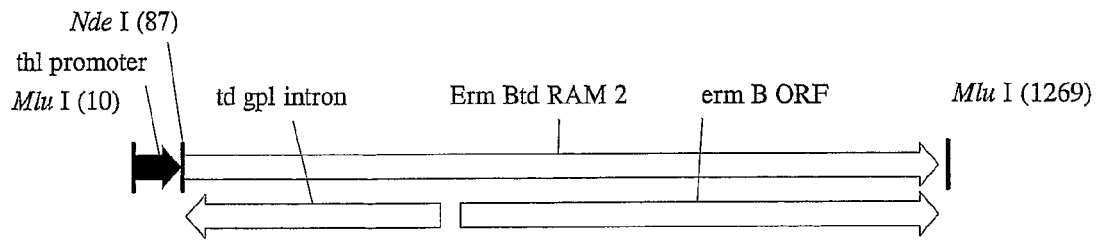

ErmBtdRAM2
1275 bp

| Position | Feature |
|---|---|
| 10 | MluI site |
| 15-84 | *thl* promoter with internal deletion |
| 85-90 | NdeI site |
| 88-1254 | Entire ErmBtdRAM2 ORF including linker and interrupted by *td* group I intron |
| 92-484 (c) | *td* group I intron (with IEP deletion) |
| 517-1254 | original *ermB* ORF |
| 1269 | MluI site |

(c) indicates feature present on complementary strand

ErmBtdRAM2 sequence:
```
CTACTAGTAC GCGTTATATT GATAAAAATA ATAATAGTGG GTATAATTAA GTTGTTAGAG   60
AAAACGTATA AATTAGGAGG GATTCATATG GCATTATGTT CAGATAAGGT CGTTAATCTT  120
ACCCCGGAAT TATATCCAGC TGCATGTCAC CATGCAGAGC AGACTATATC TCCAACTTGT  180
TAAAGCAAGT TGTCTATCGT TTCGAGTCAC TTGACCCTAC TCCCCAAAGG GATAGTCGTT  240
AGGCATTTAT GTAGAACCAA TTCCATTTAT CAGATTTTAC ACGATAAGTA ACTAATCCAG  300
ACGAAATTTT CTCTAGAGAA AGTATTTTTA ATCTGATAAA TTCCGCTTTT CATAAATACC  360
TCTTTAAATA TAGAAGTATT TATTAAAGGG CAGTCCTACA ATTTAGCACG GGATTGTCTA  420
CTAGAGAGGT TCCCCGTTTA GATAGATTAC AAGTATAAGT CACCTTATAC TCAGGCCTCA  480
ATTAACCCAA GAGATGCTGG TGCTTCTGGT GCTGGTATGA ACAAAAATAT AAAATATTCT  540
CAAAACTTTT TAACGAGTGA AAAAGTACTC AACCAAATAA TAAAACAATT GAATTTAAAA  600
GAAACCGATA CCGTTTACGA AATTGGAACA GGTAAAGGGC ATTTAACGAC GAAACTGGCT  660
AAAATAAGTA AACAGGTAAC GTCTATTGAA TTAGACAGTC ATCTATTCAA CTTATCGTCA  720
GAAAAATTAA AACTGAATAC TCGTGTCACT TTAATTCACC AAGATATTCT ACAGTTTCAA  780
TTCCCTAACA AACAGAGGTA TAAAATTGTT GGGAGTATTC CTTACCATTT AAGCACACAA  840
ATTATTAAAA AAGTGGTTTT TGAAAGCCAT GCGTCTGACA TCTATCTGAT TGTTGAAGAA  900
GGATTCTACA AGCGTACCTT GGATATTCAC CGAACACTAG GGTTGCTCTT GCACACTCAA  960
GTCTCGATTC AGCAATTGCT TAAGCTGCCA GCGGAATGCT TTCATCCTAA ACCAAAAGTA 1020
AACAGTGTCT TAATAAAACT TACCCGCCAT ACCACAGATG TTCCAGATAA ATATTGGAAG 1080
CTATATACGT ACTTTGTTTC AAAATGGGTC AATCGAGAAT ATCGTCAACT GTTTACTAAA 1140
AATCAGTTTC ATCAAGCAAT GAAACACGCC AAAGTAAACA ATTAAGTAC CGTTACTTAT 1200
GAGCAAGTAT TGTCTATTTT TAATAGTTAT CTATTATTTA ACGGGAGGAA ATAATTCTAT 1260
GAGTCGCACG CGTTC                                                 1275
```

Fig. 10

| Position | Feature |
|---|---|
| 1-2214 | Retargeting nucleic acid |
| 1 | HindIII site |
| 7-30 | IBS |
| 253-257 | EBS2 |
| 307-314 | EBS1d |
| 339 | BsrGI |
| 740-1906 (c) | ErmBtdRAM2 |
| 740-1477 (c) | ErmB ORF |
| 1510-1902 | td group I intron (with IEP deletion) |
| 1910-1979 (c) | thl promoter (containing internal deletion) |
| 2205-2214 | 3' exon of L1.LtrB group II intron |

| | |
|---|---|
| 2451-4250 | LtrA ORF |
| 4387-4676 | T1/T2 transcriptional terminators |
| 5153-6628 (c) | pCB102 replicon |
| 6893-7516 | *catP* gene |
| 8034-8579 | ColE1 replicon |
| 8877-9968 (c) | *lacI* ORF |
| 10563-11315 (c) | *oriT* origin of transfer |
| 11526-11728 | *fac* promoter |

(c) indicates feature present on complementary strand pMTL5402FlacZTTErmBtdRAM2 (aka pMTL007) sequence.

```
AGCTTATAAT TATCCTTACG TGACGGTTAA GTGCGCCCAG ATAGGGTGTT AAGTCAAGTA   60
GTTTAAGGTA CTACTCTGTA AGATAACACA GAAAACAGCC AACCTAACCG AAAAGCGAAA  120
GCTGATACGG GAACAGAGCA CGGTTGGAAA GCGATGAGTT ACCTAAAGAC AATCGGGTAC  180
GACTGAGTCG CAATGTTAAT CAGATATAAG GTATAAGTTG TGTTTACTGA ACGCAAGTTT  240
CTAATTTCGG TTTCACGTCG ATAGAGGAAA GTGTCTGAAA CCTCTAGTAC AAAGAAAGGT  300
AAGTTACGTT AACCGACTTA TCTGTTATCA CCACATTTGT ACAATCTGTA GGAGAACCTA  360
TGGGAACGAA ACGAAAGCGA TGCCGAGAAT CTGAATTTAC CAAGACTTAA CACTAACTGG  420
GGATACCCTA ACAAGAATG CCTAATAGAA AGGAGGAAAA AGGCTATAGC ACTAGAGCTT  480
GAAAATCTTG CAAGGGTACG GAGTACTCGT AGTAGTCTGA GAAGGGTAAC GCCCTTTACA  540
TGGCAAAGGG GTACAGTTAT TGTGTACTAA AATTAAAAAT TGATTAGGGA GGAAAACCTC  600
AAAATGAAAC CAACAATGGC AATTTTAGAA AGAATCAGTA AAAATTCACA AGAAAATATA  660
GACGAAGTTT TTACAAGACT TTATCGTTAT CTTTTACGTC CAGATATTTA TTACGTGGCG  720
ACGCGTGCGA CTCATAGAAT TATTTCCTCC CGTTAAATAA TAGATAACTA TTAAAAATAG  780
ACAATACTTG CTCATAAGTA ACGGTACTTA AATTGTTTAC TTTGGCGTGT TCATTGCTT  840
GATGAAACTG ATTTTTAGTA AACAGTTGAC GATATTCTCG ATTGACCCAT TTGAAACAA  900
AGTACGTATA TAGCTTCCAA TATTTATCTG GAACATCTGT GGTATGGCGG GTAAGTTTTA  960
TTAAGACACT GTTTACTTTT GGTTTAGGAT GAAAGCATTC CGCTGGCAGC TTAAGCAATT 1020
GCTGAATCGA GACTTGAGTG TGCAAGAGCA ACCCTAGTGT TCGGTGAATA TCCAAGGTAC 1080
GCTTGTAGAA TCCTTCTTCA ACAATCAGAT AGATGTCAGA CGCATGGCTT TCAAAAACCA 1140
CTTTTTTAAT AATTTGTGTG CTTAAATGGT AAGGAATACT CCCAACAATT TTATACCTCT 1200
GTTTGTTAGG GAATTGAAAC TGTAGAATAT CTTGGTGAAT TAAAGTGACA CGAGTATTCA 1260
GTTTTAATTT TTCTGACGAT AAGTTGAATA GATGACTGTC TAATTCAATA GACGTTACCT 1320
GTTTACTTAT TTTAGCCAGT TTCGTCGTTA AATGCCCTTT ACCTGTTCCA ATTTCGTAAA 1380
CGGTATCGGT TTCTTTTAAA TTCAATTGTT TTATTATTTG GTTGAGTACT TTTTCACTCG 1440
TTAAAAAGTT TTGAGAATAT TTTATATTTT TGTTCATACC AGCACCAGAA GCACCAGCAT 1500
CTCTTGGGTT AATTGAGGCC TGAGTATAAG GTGACTTATA CTTGTAATCT ATCTAAACGG 1560
GGAACCTCTC TAGTAGACAA TCCCGTGCTA AATTGTAGGA CTGCCCTTTA ATAAATACTT 1620
CTATATTTAA AGAGGTATTT ATGAAAGCG GAATTTATCA GATTAAAAAT ACTTTCTCTA 1680
GAGAAAATTT CGTCTGGATT AGTTACTTAT CGTGTAAAAT CTGATAAATG GAATTGGTTC 1740
TACATAAATG CCTAACGACT ATCCCTTTGG GGAGTAGGGT CAAGTGACTC GAAACGATAG 1800
ACAACTTGCT TTAACAAGTT GGAGATATAG TCTGCTCTGC ATGGTGACAT GCAGCTGGAT 1860
ATAATTCCGG GGTAAGATTA ACGACCTTAT CTGAACATAA TGCCATATGA ATCCCTCCTA 1920
ATTTATACGT TTTCTCTAAC AACTTAATTA TACCCACTAT TATTATTTTT ATCAATATAA 1980
CGCGTTGGGA AATGGCAATG ATAGCGAAAC AACGTAAAAC TCTTGTTGTA TGCTTTCATT 2040
GTCATCGTCA CGTGATTCAT AAACACAAGT GAATGTCGAC AGTGAATTTT TACGAACGAA 2100
CAATAACAGA GCCGTATACT CCGAGAGGGG TACGTACGGT TCCCGAAGAG GGTGGTGCAA 2160
```

Fig. 11 (cont.)

```
ACCAGTCACA GTAATGTGAA CAAGGCGGTA CCTCCCTACT TCACCATATC ATTTTCTGCA 2220
GCCCCCTAGA AATAATTTTG TTTAACTTTA AGAAGGAGAT ATACATATAT GGCTAGATCG 2280
TCCATTCCGA CAGCATCGCC AGTCACTATG GCGTGCTGCT AGCGCTATAT GCGTTGATGC 2340
AATTTCTATG CACTCGTAGT AGTCTGAGAA GGGTAACGCC CTTTACATGG CAAAGGGGTA 2400
CAGTTATTGT GTACTAAAAT TAAAAATTGA TTAGGGAGGA AAACCTCAAA ATGAAACCAA 2460
CAATGGCAAT TTTAGAAAGA ATCAGTAAAA ATTCACAAGA AAATATAGAC GAAGTTTTTA 2520
CAAGACTTTA TCGTTATCTT TTACGTCCAG ATATTTATTA CGTGGCGTAT CAAAATTTAT 2580
ATTCCAATAA AGGAGCTTCC ACAAAAGGAA TATTAGATGA TACAGCGGAT GGCTTTAGTG 2640
AAGAAAAAAT AAAAAAGATT ATTCAATCTT TAAAAGACGG AACTTACTAT CCTCAACCTG 2700
TACGAAGAAT GTATATTGCA AAAAAGAATT CTAAAAAGAT GAGACCTTTA GGAATTCCAA 2760
CTTTCACAGA TAAATTGATC CAAGAAGCTG TGAGAATAAT TCTTGAATCT ATCTATGAAC 2820
CGGTATTCGA AGATGTGTCT CACGGTTTTA GACCTCAACG AAGCTGTCAC ACAGCTTTGA 2880
AAACAATCAA AAGAGAGTTT GGCGGCGCAA GATGGTTTGT GGAGGGAGAT ATAAAAGGCT 2940
GCTTCGATAA TATAGACCAC GTTACACTCA TTGGACTCAT CAATCTTAAA ATCAAAGATA 3000
TGAAAATGAG CCAATTGATT TATAAATTTC TAAAAGCAGG TTATCTGGAA AACTGGCAGT 3060
ATCACAAAAC TTACAGCGGA ACACCTCAAG GTGGAATTCT ATCTCCTCTT TTGGCCAACA 3120
TCTATCTTCA TGAATTGGAT AAGTTTGTTT TACAACTCAA AATGAAGTTT GACCGAGAAA 3180
GTCCAGAAAG AATAACACCT GAATATCGGG AGCTCCACAA TGAGATAAAA AGAATTTCTC 3240
ACCGTCTCAA GAAGTTGGAG GGTGAAGAAA AAGCTAAAGT TCTTTTAGAA TATCAAGAAA 3300
AACGTAAAAG ATTACCCACA CTCCCCTGTA CCTCACAGAC AAATAAAGTA TTGAAATACG 3360
TCCGGTATGC GGACGACTTC ATTATCTCTG TTAAAGGAAG CAAAGAGGAC TGTCAATGGA 3420
TAAAAGAACA ATTAAAACTT TTTATTCATA ACAAGCTAAA AATGGAATTG AGTGAAGAAA 3480
AAACACTCAT CACACATAGC AGTCAACCCG CTCGTTTTCT GGGATATGAT ATACGAGTAA 3540
GGAGATCTGG AACGATAAAA CGATCTGGTA AAGTCAAAAA GAGAACACTC AATGGGAGTG 3600
TAGAACTCCT TATTCCTCTT CAAGACAAAA TTCGTCAATT TATTTTTGAC AAGAAAATAG 3660
CTATCCAAAA GAAAGATAGC TCATGGTTTC CAGTTCACAG GAAATATCTT ATTCGTTCAA 3720
CAGACTTAGA AATCATCACA ATTTATAATT CTGAACTCCG CGGGATTTGT AATTACTACG 3780
GTCTAGCAAG TAATTTTAAC CAGCTCAATT ATTTTGCTTA TCTTATGGAA TACAGCTGTC 3840
TAAAAACGAT AGCCTCCAAA CATAAGGGAA CACTTTCAAA AACCATTTCC ATGTTTAAAG 3900
ATGGAAGTGG TTCGTGGGGG ATCCCGTATG AGATAAAGCA AGGTAAGCAG CGCCGTTATT 3960
TTGCAAATTT TAGTGAATGT AAATCCCCTT ATCAATTTAC GGATGAGATA AGTCAAGCTC 4020
CTGTATTGTA TGGCTATGCC CGGAATACTC TTGAAAACAG GTTAAAAGCT AAATGTTGTG 4080
AATTATGTGG GACGTCTGAT GAAAATACTT CCTATGAAAT TCACCATGTC AATAAGGTCA 4140
AAAATCTTAA AGGCAAAGAA AATGGGAAA TGGCAATGAT AGCGAAACAA CGTAAAACTC 4200
TTGTTGTATG CTTTCATTGT CATCGTCACG TGATTCATAA ACACAAGTGA ATGTCGAGCA 4260
CCCGTTCTCG GAGCACTGTC CGACCGCTTT GGCCGCCGCC CAGTCCTGCT CGCTTCGCTA 4320
CTTGGAGCCA CTATCGACTA CGCGATCATG GCGACCACAC CCGTCCTGTG GATCGCCAAG 4380
CTCGCCGATG GTAGTGTGGG GTCTCCCCAT GCGAGAGTAG GGAACTGCCA GGCATCAAAT 4440
AAAACGAAAG GCTCAGTCGA AAGACTGGGC CTTTCGTTTT ATCTGTTGTT TGTCGGTGAA 4500
CGCTCTCCTG AGTAGGACAA ATCCGCCGGG AGCGGATTTG AACGTTGCGA AGCAACGGCC 4560
CGGAGGGTGG CGGGCAGGAC GCCCGCCATA AACTGCCAGG CATCAAATTA AGCAGAAGGC 4620
CATCCTGACG GATGGCCTTT TTGCGTTTCT ACAAACTCTT CCTGTCGTCA TATCTACAAG 4680
CCATCCCCCC ACAGATACGG TAAACTAGCC TCGTTTTTGC ATCAGGAAAG CAGAACGCCA 4740
TGAGCGGCCT CATTTCTTAT TCTGAGTTAC AACAGTCCGC ACCGCTGTCC GGTAGCTCCT 4800
TCCGGTGGGC GCGGGCATG ACTATCGTCG CCGCACTTAT GACTGTCTTC TTTATCATGC 4860
AACTCGTAGG ACAGGTGCCA GCTTGGCACT GGCCGTCGTT TTACAACGTC GTGACTGGGA 4920
AAACCCTGGC GTTACCCAAC TTAATCGCCT TGCAGCACAT CCCCCTTTCG CCAGCTGGCG 4980
TAATAGCGAA GAGGCCCGCA CCGATCGCCC TTCCCAACAG TTGCGCAGCC TGAATGGCGA 5040
ATGGCGCTAG CGAAGAGATG CAGCAGCCAT TATTTTTTTG AACAATTGAC AATTCATTTC 5100
TTATTTTTTA TTAAGTGATA GTCAAAAGGC ATAACAGTGC TGAATAGAAA GAATTTACA 5160
GAAAAGAAAA TTATAGAATT TAGTATGATT AATTATACTC ATTTATGAAT GTTTAATTGA 5220
```

Fig. 11 (cont.)

```
ATACAAAAAA AAATACTTGT TATGTATTCA ATTACGGGTT AAAATATAGA CAAGTTGAAA 5280
AATTTAATAA AAAAATAAGT CCTCAGCTCT TATATATTAA GCTACCAACT TAGTATATAA 5340
GCCAAAACTT AAATGTGCTA CCAACACATC AAGCCGTTAG AGAACTCTAT CTATAGCAAT 5400
ATTTCAAATG TACCGACATA CAAGAGAAAC ATTAACTATA TATATTCAAT TTATGAGATT 5460
ATCTTAACAG ATATAAATGT AAATTGCAAT AAGTAAGATT TAGAAGTTTA TAGCCTTTGT 5520
GTATTGGAAG CAGTACGCAA AGGCTTTTTT ATTTGATAAA AATTAGAAGT ATATTTATTT 5580
TTTCATAATT AATTTATGAA AATGAAAGGG GGTGAGCAAA GTGACAGAGG AAAGCAGTAT 5640
CTTATCAAAT AACAAGGTAT TAGCAATATC ATTATTGACT TTAGCAGTAA ACATTATGAC 5700
TTTTATAGTG CTTGTAGCTA AGTAGTACGA AAGGGGGAGC TTTAAAAAGC TCCTTGGAAT 5760
ACATAGAATT CATAAATTAA TTTATGAAAA GAAGGGCGTA TATGAAAACT TGTAAAAATT 5820
GCAAAGAGTT TATTAAAGAT ACTGAAATAT GCAAAATACA TTCGTTGATG ATTCATGATA 5880
AAACAGTAGC AACCTATTGC AGTAAATACA ATGAGTCAAG ATGTTTACAT AAAGGGAAAG 5940
TCCAATGTAT TAATTGTTCA AAGATGAACC GATATGGATG GTGTGCCATA AAAATGAGAT 6000
GTTTTACAGA GGAAGAACAG AAAAAAGAAC GTACATGCAT TAAATATTAT GCAAGGAGCT 6060
TTAAAAAAGC TCATGTAAAG AAGAGTAAAA AGAAAAAATA ATTTATTTAT TAATTTAATA 6120
TTGAGAGTGC CGACACAGTA TGCACTAAAA AATATATCTG TGGTGTAGTG AGCCGATACA 6180
AAAGGATAGT CACTCGCATT TCATAATAC ATCTTATGTT ATGATTATGT GTCGGTGGGA 6240
CTTCACGACG AAAACCCACA ATAAAAAAG AGTTCGGGGT AGGGTTAAGC ATAGTTGAGG 6300
CAACTAAACA ATCAAGCTAG GATATGCAGT AGCAGACCGT AAGGTCGTTG TTTAGGTGTG 6360
TTGTAATACA TACGCTATTA AGATGTAAAA ATACGGATAC CAATGAAGGG AAAAGTATAA 6420
TTTTTGGATG TAGTTTGTTT GTTCATCTAT GGGCAAACTA CGTCCAAAGC CGTTTCCAAA 6480
TCTGCTAAAA AGTATATCCT TTCTAAAATC AAAGTCAAGT ATGAAATCAT AAATAAAGTT 6540
TAATTTTGAA GTTATTATGA TATTATGTTT TTCTATTAAA ATAAATTAAG TATATAGAAT 6600
AGTTTAATAA TAGTATATAC TTAATGTGAT AAGTGTCTGA CAGCTGACCG GTCTAAAGAG 6660
GTCCCTAGCG CCTACGGGGA ATTTGTATCG ATAAGGGGTA CAAATTCCCA CTAAGCGCTC 6720
GGCGGGGATC GATCCCGGGT ACGTACCCGG CAGTTTTTCT TTTTCGGCAA GTGTTCAAGA 6780
AGTTATTAAG TCGGGAGTGC AGTCGAAGTG GGCAAGTTGA AAAATTCACA AAAATGTGGT 6840
ATAATATCTT TGTTCATTAG AGCGATAAAC TTGAATTTGA GAGGGAACTT AGATGGTATT 6900
TGAAAAAATT GATAAAAATA GTTGGAACAG AAAAGAGTAT TTTGACCACT ACTTTGCAAG 6960
TGTACCTTGT ACCTACAGCA TGACCGTTAA AGTGGATATC ACACAAATAA AGGAAAGGG 7020
AATGAAACTA TATCCTGCAA TGCTTTATTA TATTGCAATG ATTGTAAACC GCCATTCAGA 7080
GTTTAGGACG GCAATCAATC AAGATGGTGA ATTGGGGATA TATGATGAGA TGATACCAAG 7140
CTATACAATA TTTCACAATG ATACTGAAAC ATTTTCCAGC CTTTGGACTG AGTGTAAGTC 7200
TGACTTTAAA TCATTTTTAG CAGATTATGA AAGTGATACG CAACGGTATG GAAACAATCA 7260
TAGAATGGAA GGAAAGCCAA ATGCTCCGGA AAACATTTTT AATGTATCTA TGATACCGTG 7320
GTCAACCTTC GATGGCTTTA ATCTGAATTT GCAGAAAGGA TATGATTATT TGATTCCTAT 7380
TTTTACTATG GGGAAATATT ATAAAGAAGA TAACAAAATT ATACTTCCTT TGGCAATTCA 7440
AGTTCATCAC GCAGTATGTG ACGGATTTCA CATTTGCCGT TTTGTAAACG AATTGCAGGA 7500
ATTGATAAAT AGTTAACTTC AGGTTTGTCT GTAACTAAAA ACAAGTATTT AAGCAAAAAC 7560
ATCGTAGAAA TACGGTGTTT TTTGTTACCC TAAAATCTAC AATTTTATAC ATAACCACAG 7620
GTTAGTACAA AGACCTTGTG TTTCTTTTTG AAAGGCTTAA AACAAGGATT TTTCCTTGAT 7680
TTAAGCCCCG AAAAGCAACA CAACCAAGGT TTTAGTATCA ATCTGTGGTT TTTATATTTT 7740
CAGAGACCGG TCAGGAGTCA GGCAACTATG GATGAACGAA ATAGACAGAT CGCTGAGATA 7800
GGTGCCTCAC TGATTAAGCA TTGGTAACTG TCAGACCAAG TTTACTCATA TATACTTTAG 7860
ATTGATTTAA AACTTCATTT TTAATTTAAA AGGATCTAGG TGAAGATCCT TTTTGATAAT 7920
CTCATGACCA AAATCCCTTA ACGTGAGTTT TCGTTCCACT GAGCGTCAGA CCCCGTAGAA 7980
AAGATCAAAG GATCTTCTTG AGATCCTTTT TTTCTGCGCG TAATCTGCTG CTTGCAAACA 8040
AAAAACCAC CGCTACCAGC GGTGGTTTGT TGCCGGATC AAGAGCTACC AACTCTTTTT 8100
CCGAAGGTAA CTGGCTTCAG CAGAGCGCAG ATACCAAATA CTGTCCTTCT AGTGTAGCCG 8160
TAGTTAGGCC ACCACTTCAA GAACTCTGTA GCACCGCCTA CATACCTCGC TCTGCTAATC 8220
CTGTTACCAG TGGCTGCTGC CAGTGGCGAT AAGTCGTGTC TTACCGGGTT GGACTCAAGA 8280
```

Fig. 11 (cont.)

```
CGATAGTTAC CGGATAAGGC GCAGCGGTCG GGCTGAACGG GGGGTTCGTG CACACAGCCC 8340
AGCTTGGAGC GAACGACCTA CACCGAACTG AGATACCTAC AGCGTGAGCA TTGAGAAAGC 8400
GCCACGCTTC CCGAAGGGAG AAAGGCGGAC AGGTATCCGG TAAGCGGCAG GGTCGGAACA 8460
GGAGAGCGCA CGAGGGAGCT TCCAGGGGGA AACGCCTGGT ATCTTTATAG TCCTGTCGGG 8520
TTTCGCCACC TCTGACTTGA GCGTCGATTT TTGTGATGCT CGTCAGGGGG GCGGAGCCTA 8580
TGGAAAAACG CCAGCAACGC GGCCTTTTTA CGGTTCCTGG CCTTTTGCTG GCCTTTTGCT 8640
CACATGTTCT TTCCTGCGTT ATCCCCTGAT TCTGTGGATA ACCGTATTAC CGCCTTTGAG 8700
TGAGCTGATA CCGCTCGCCG CAGCCGAACG ACCGAGCGCA GCGAGTCAGT GAGCGAGGAA 8760
GCGGAAGCAG TAAGACGGGT AAGCCTGTTG ATGATACCGC TGCCTTACTG GGTGCATTAG 8820
CCAGTCTGAA TGACCTGTCA CGGGATAATT CCTAACTCAC ATTAATTGCG TTGCGCTCAC 8880
TGCCCGCTTT CCAGTCGGGA AACCTGTCGT GCCAGCTGCA TTAATGAATC GGCCAACGCG 8940
CGGGGAGAGG CGGTTTGCGT ATTGGGCGCC AGGGTGGTTT TCTTTTCAC CAGTGAGACG 9000
GGCAACAGCT GATTGCCCTT CACCGCCTGG CCCTGAGAGA GTTGCAGCAA GCGGTCCACG 9060
CTGGTTTGCC CCAGCAGGCG AAAATCCTGT TTGATGGTGG TTGACGGCGG GATATAACAT 9120
GAGCTGTCTT CGGTATCGTC GTATCCCACT ACCGAGATAT CCGCACCAAC GCGCAGCCCG 9180
GACTCGGTAA TGGCGCGCAT TGCGCCCAGC GCCATCTGAT CGTTGGCAAC CAGCATCGCA 9240
GTGGGAACGA TGCCCTCATT CAGCATTTGC ATGGTTTGTT GAAAACCGGA CATGGCACTC 9300
CAGTCGCCTT CCCGTTCCGC TATCGGCTGA ATTTGATTGC GAGTGAGATA TTTATGCCAG 9360
CCAGCCAGAC GCAGACGCGC CGAGACAGAA CTTAATGGGC CCGCTAACAG CGCGATTTGC 9420
TGGTGACCCA ATGCGACCAG ATGCTCCACG CCCAGTCGCG TACCGTCTTC ATGGGAGAAA 9480
ATAATACTGT TGATGGGTGT CTGGTCAGAG ACATCAAGAA ATAACGCCGG AACATTAGTG 9540
CAGGCAGCTT CCACAGCAAT GGCATCCTGG TCATCCAGCG GATAGTTAAT GATCAGCCCA 9600
CTGACGCGTT GCGCGAGAAG ATTGTGCACC GCCGCTTTAC AGGCTTCGAC GCCGCTTCGT 9660
TCTACCATCG ACACCACCAC GCTGGCACCC AGTTGATCGG CGCGAGATTT AATCGCCGCG 9720
ACAATTTGCG ACGGCGCGTG CAGGGCCAGA CTGGAGGTGG CAACGCCAAT CAGCAACGAC 9780
TGTTTGCCCG CCAGTTGTTG TGCCACGCGG TTGGGAATGT AATTCAGCTC CGCCATCGCC 9840
GCTTCCACTT TTTCCCGCGT TTTCGCAGAA ACGTGGCTGG CCTGGTTCAC CACGCGGGAA 9900
ACGGTCTGAT AAGAGACACC GGCATACTCT GCGACATCGT ATAACGTTAC TGGTTTCATA 9960
TGTTGCACCT CTACTTTAAT AATTTTTAAC TTTTATATAT GATTAATTTA ATTGTTTGTT 10020
AAATTTATAT CAATCAATGC TATGAATATT TCTTTATACC TTATTGTAAC AAAAAAATAT 10080
TGGAAATGTT GAATTTTCAG AATATTATTT TTATTATATT ATTAATTTTA TATATTCATT 10140
TTTATAAGAT TTCACAACAC GAACGTAATA TAATATATCT TCCTCATCTT CTGAAAAGAT 10200
TATACTAATT CTATTCATGT TACTTATAAT CTTATTTTGG TAAATCGAAT TTTTCAATTA 10260
TATGTTCGGC AACCTTTATC CCATCAACAG CCGCTGATAT TATACCACCT GCAAATCCTG 10320
CCCCTTCTCC AGTTGGATAA AGTCCGCATA CATTTATACT TTCAAGTGAA GCATTTCTAT 10380
TCAATCTAAC TGGTGCTGAT GTTCTTGTCT CAATTCCCGT TAAAATTGCA TCTTCTCTTG 10440
CATACCCTTT TATCTTTTTA TCAAAATTTA TAATTCCTTC TTTAAGAGCC TCTACAACAT 10500
AATCAGGTAA ACATTCTTTT AATTCCCTGA ATTATCTGCA GAATTCGCCC TTCCTGCTTC 10560
GGGGTCATTA TAGCGATTTT TTCGGTATAT CCATCCTTTT TCGCACGATA TACAGGATTT 10620
TGCCAAAGGG TTCGTGTAGA CTTTCCTTGG TGTATCCAAC GGCGTCAGCC GGGCAGGATA 10680
GGTGAAGTAG GCCCACCCGC GAGCGGGTGT TCCTTCTTCA CTGTCCCTTA TTCGCACCTG 10740
GCGGTGCTCA ACGGGAATCC TGCTCTGCGA GGCTGGCCGG CTACCGCCGG CGTAACAGAT 10800
GAGGGCAAGC GGATGGCTGA TGAAACCAAG CCAACCAGGA AGGGCAGCCC ACCTATCAAG 10860
GTGTACTGCC TTCCAGACGA ACGAAGAGCG ATTGAGGAAA AGGCGGCGGC GGCCGGCATG 10920
AGCCTGTCGG CCTACCTGCT GGCCGTCGGC CAGGGCTACA AAATCACGGG CGTCGTGGAC 10980
TATGAGCACG TCCGCGAGCT GGCCCGCATC AATGGCGACC TGGGCCGCCT GGGCGGCCTG 11040
CTGAAACTCT GGCTCACCGA CGACCCGCGC ACGGCGCGGT TCGGTGATGC CACGATCCTC 11100
GCCCTGCTGG CGAAGATCGA AGAGAAGCAG GACGAGCTTG CAAGGTCAT GATGGGCGTG 11160
GTCCGCCCGA GGGCAGAGCC ATGACTTTTT TAGCCGCTAA AACGGCCGGG GGTGCGCGT 11220
GATTGCCAAG CACGTCCCCA TGCGCTCCAT CAAGAAGAGC GACTTCGCGG AGCTGGTGAA 11280
GTACATCACC GACGAGCAAG GCAAGACCGA TCCCCATCCC GAAGTGGTCA GACTGGAAAA 11340
```

Fig. 11 (cont.)

```
TCAGAGGGCA GGAACTGCGA ACAGCAAAAA GTCAGATAGC ACCACATAGC AGACCCGCCA 11400
TAAAACGCCC TGAGAGCCCG TGACGGGCTT TTCTTGTATT ATGGGTAGTT TCCTTGCATG 11460
AATCCATAAA AGGCGCCCAA TACGCAAACC GCCTCTCCCC GCGCGTTGGC CGATTCATTA 11520
ATGCAGAATT CCCCGGATCG AGATAGTATA TGATGCATAT TCTTTAAATA TAGATAAAGT 11580
TATAGAAGCA ATAGAAGATT TAGGATTTAC TGTAATATAA ATTACACTTT TAAAAAGTTT 11640
AAAAACATGA TACAATAAGT TATGGTTGGA ATTGTTATCC GCTCACAATT CCAACTTATG 11700
ATTAAAATTT TAAGGAGGTG TATTTCATAT GACCATGATT ACGAATTCGA GCTCGGTACC 11760
CGGGGATCCT CTAGAGTCGA CGTCACGCGT CCATGGAGAT CTCGAGGCCT GCAGGCATGC 11820
A                                                                11821
```

Fig. 11 (cont.)

DNA MOLECULES AND METHODS

CROSS-REFERENCE TO RELATED APPLICATIONS

This application is a continuation of U.S. patent application Ser. No. 12/305,843, which adopts the international filing date of Jun. 21, 2007, which is a National Phase application under 35 U.S.C. § 371 of International Application No. PCT/GB2007/002308 filed Jun. 21, 2007 and claims the benefit of Great Britain Application No. 0612301.2 filed Jun. 21, 2006, the disclosures of which are incorporated herein by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 404172002201SubSeqList.txt, date recorded: Jan. 6, 2016, size: 49 KB).

The present invention relates to DNA molecules and methods using the molecules for introducing mutations into DNA in a Gram positive bacterial cell, particularly a cell of the class Clostridia.

The class Clostridia includes the orders Clostridiales, Halanaerobiales and Thermoanaerobacteriales. The order Clostridiales includes the family Clostridiaceae, which includes the genus Clostridium.

Clostridium is one of the largest bacterial genera. It is composed of obligately anaerobic, Gram-positive, spore formers. Certain members may be employed on an industrial scale for the production of chemical fuels, eg., Clostridium thermocellum and Clostridium acetobutylicum. This latter clostridial species, together with other benign representatives, additionally has demonstrable potential as a delivery vehicle for therapeutic agents directed against cancer. However, the genus has achieved greatest notoriety as a consequence of those members that cause disease in humans and domestic animals, eg, Clostridium difficile, Clostridium botulinum and Clostridium perfringens.

Despite the tremendous commercial and medical importance of the genus, progress either towards their effective exploitation, or on the development of rational approaches to counter the diseases they cause, has been severely hindered by the lack of a basic understanding of the organisms' biology at the molecular level. This is largely a consequence of an absence of effective genetic tools.

In recent years, the complete genome sequences of all of the major species have been determined from at least one representative strain, including C. acetobutylicum, C. difficile, C. botulinum and C. perfringens. In other bacterial species such knowledge can act as a springboard for more effective disease management or for the generation of strains with improved process properties. A pivotal tool in such undertakings is the ability to rationally integrate DNA into the genome. Such technology may be employed: (i) to generate specific mutants as a means of ascribing function to individual genes, and gene sets, as an essential first step towards understanding physiology and pathogenesis; (ii) to insertionally inactivate regulatory or structural genes as a means of enhancing the production of desirable commercial commodities, and; (iii) to stably introduce genetic information encoding adventitious factors. However, there are currently no effective integration vectors for mutational studies in any Clostridium sp. and the ability to insertionally inactivate genes in the genus remains woefully inadequate.

Previous attempts to make mutants in Clostridium sp. relied on homologous recombination between an integration vector and the host chromosome In C. perfringens strain 13, C. beijerinckii NCIMB 8052, C. acetobutylicum ATCC 824 and C. difficile CD37, replication-minus plasmids carrying regions of the host chromosome have been shown to integrate into the genome via homologous recombination (Shimizu et al (1994) J. Bacteriol. 176: 1616-23; Wilkinson and Young (1994) Microbiol. 140: 89-95; Green et al (1996) Microbiol. 142: 2079-2086; Liyanage et al (2001) Appl. Environ. Microbiol. 67: 2004-2010). In the case of C. beijerinckii and C. difficile, vectors were mobilized from E. coli donors. In C. perfringens and C. acetobutylicum, plasmids were introduced by transformation. Integrants arose in C. beijerinckii at frequencies of $10^{-6}$ to $10^{-7}$ per recipient, which represented some two orders of magnitude lower than the transfer frequency observed ($10^{-4}$ to $10^{-5}$) with replication proficient plasmids (Wilkinson and Young, 1994, supra). In the case of C. difficile, no indication of the frequencies attained was reported (Liyanage et al, 2001, supra). In C. acetobutylicum, integrants arose at a frequency of 0.8 to 0.9 'colonies' per µg of DNA (Green et al, 1996, supra). In the above integrants, plasmid sequences at the target site were flanked by two directly repeated copies of the DNA segment directing integration. As a consequence, they were segregationally unstable, e.g., losses per 30 generations of between 1.8 to $3.0 \times 10^{-3}$ for C. acetobutylicum (Green et al, 1996, supra) and between 0.37 to $1.3 \times 10^{-3}$ for C. beijerinckii (Wilkinson and Young, 1994, supra).

It follows that integrants resulting from allelic exchange are preferred. Accordingly, double crossover mutants were sought and obtained in C. perfringens (Awad et al (1995) Mol. Microbiol. 15: 191-202; Bannam et al (1995) Mol. Microbiol. 16: 535-551. However, allelic exchange only proved possible through the inclusion of rather long (3.0 kb) regions of homology on either side of the antibiotic resistance gene employed to inactivate the target gene. Furthermore, even with this provision, the isolation of mutants proved highly variable (i.e., plc mutants were only obtained in 2 of 10 independent experiments), and many mutants can take up to 6 months to isolate, while others may never be isolated at all. Rare integration events could be detected in C. perfringens as a consequence of the high frequency with which DNA can be transformed into this organism. Attempts to generate double crossover mutants in other clostridial species have been unsuccessful.

To date the generation of mutants in a range of clostridial species, other than C. perfringens, using classical homologous recombination has proven difficult. Thus, only five mutations have ever been made in C. acetobutylicum. Four (butK, CAC3075; pta, CAC1742; aad, CACP0162, and; solR, CACP061) were made by single cross-over integration of a replication deficient plasmids (Green et al., 1996, supra; Green and Bennett (1996) Appl. Biochem. Biotechnol. 213, 57-58; Harris et al (2002) J. Bacteriol. 184, 3586-3597) while a fifth in spo0A (CAC2071) was isolated by a strategy which attempted, but did not succeed, in the generation of a mutant by reciprocal exchange using a replication-defective plasmid (Nair et al (1999) J. Bacteriol. 181, 319-330). Similarly, the generation of only three directed mutants has been reported in C. difficile. One mutant (gldA, CD0274) was generated using a replication-deficient plasmid (Liyanage et al, 2001, supra) although this event appeared to be lethal and mutant cells could not be propagated. The other two genes inactivated (rgaR, CD3255 and rgbR, CD1089)

arose following the introduction of a replication-defective plasmid carrying internal fragments of the two structural genes (O'Connor et al (2006) *Mol. Microbiol.* 61, 1335-1351). These latter plasmids were apparently introduced with "some difficulty" and whilst integrants were isolated, no isolation frequencies were noted. Indeed, an assessment of the efficiencies of the mutagenesis procedures previously used in both organisms is difficult to make, as no indication of the frequency with which mutants are generated is generally presented. In the case of *C. acetobutylicum* it is acknowledged (Thomas et al, (2005) Metabolic engineering of soventogenic clostridia. In: Dürre, P. Handbook on Clostridia, CRC Press. pp 813-830) to be "less than one transformant per µg plasmid DNA". Moreover, as the majority of these mutants are made by single cross-over insertion, they are unstable due to plasmid excision. For example, Southern blotting of the *C. difficile* rgaR mutant revealed the presence of "looped out", independently replicating plasmid in some cells in the population (O'Connor et al, 2006, supra).

Increasingly, technologies are being devised which capitalise on the systems involving mobile genetic elements to bring about more effective modification of bacterial genomes. The Group II intron L1.LtrB of *Lactococcus lactis* is an element that mediates its own mobility through the action of an intron-encoded reverse transcriptase (LtrA) and the excised lariat RNA. Furthermore, it may be re-targeted to virtually any desired DNA sequence through modification of the intron RNA (Guo et al (2000) *Science* 289: 452-457; Mohr et al (2000) *Genes Dev.* 14: 559-573). Thus, by appropriately mutating individual bases in the 15 bp region of the intron involved in targeting, Karberg et al (*Nature Biotech.* (2001) 19: 1162-1167) were able to direct the insertion of the element into distinct, defined positions within several different *E. coli* genes at frequencies of between 0.1 to 22%. Disruption of one of these genes, thyA, gives rise to clones that are naturally trimethoprim resistant. Thus, integrants could be selected for by culturing in the presence of trimethoprim. Integrants in other genes were identified by screening individual colonies for the presence of the L1.LtrB intron. The plasmid used to disrupt the thyA gene in *E. coli* was also used to disrupt the thyA gene in *S. flexneri* and in *S. typhimurium*. Trimethoprim resistant colonies were obtained at a frequency of 1% and 0.3% respectively.

The Group II intron L1.LtrB of *Lactococcus lactis* was used to generate knock-outs in the plc gene of *C. perfringens* (Chen et al (2005) *Appl Environ Microbiol.* 71: 7542-7). A chloramphenicol resistant plasmid containing, inter alia, a modified L1.LtrB intron designed to target the plc gene was electroporated into *C. perfringens*. Transformants were selected on chloramphenicol and were tested for the presence of the insertion in the plc gene by PCR. Of 38 colonies tested, most were negative for the insertion but two colonies contained both wild-type and intron-inserted plc gene. The latter colonies were deemed to have arisen from a single transformed bacterium, which gave rise to progeny in which the insertion occurred and progeny in which the insertion did not occur. Bacteria from these mixed colonies gave rise to pure clones, 10% of which contained intron-inserted plc gene. Thus, insertion mutants were identified via two rounds of screening without the need for selection for growth on an antibiotic, other than selection on chloramphenicol for transformation. In fact, the lack of any introduction of an antibiotic resistance gene into the chromosome was identified as a particular advantage of the method. In particular, the authors envisaged that the method could be used to construct multiple gene disruptions in the same bacterial cell using the same shuttle plasmid carrying different modified L1.LtrB introns. The frequency of transfer to *C. perfringens* is high, some two orders of magnitude greater than other Clostridial species. Moreover, the gene knockout (in plc) gives rise to an easily detected phenotype, which may be visualised readily on agar plates.

Yao at al (RNA (2006) 12: 1-11) used L1.LtrB to disrupt genes without selection in *Staphylococcus aureus*. A cadmium-induced promoter was used to direct expression of the L1.LtrB intron in *S. aureus;* induction with cadmium was beneficial to obtaining insertion mutants in one gene. When mutants were made in another gene, all colonies tested positive for insertion of the intron in the absence of cadmium.

Zhong at al (*Nucleic Acids Res.* (2003) 31: 1656-64) described a method of positively selecting for re-targeting of the Group II intron involving inserting into the Group II intron a "retrotransposition-activated selectable marker" or RAM consisting of a trimethoprim (Tp) resistance cassette containing the td intron of phage T4. The Tp resistance gene encodes a type II dihydrofolate reductase. The td intron is a Group I intron, i.e. a self-catalytic RNA-element which, in its correct orientation, can splice itself from an RNA transcript in which it is located. The orientation in which td is inserted into $Tp^R$ is such that when the gene is transcribed, the element is not spliced. Thus, the mRNA remains mutant, and the protein required for Tp resistance is not produced. When the Group II element is transcribed into RNA, during re-targeting, the opposite strand of the RAM is now present in an RNA form. Under these circumstances the td element is orientated correctly, and is spliced. As a consequence, when the Group II element retargets to the chromosome, the $Tp^R$ gene has lost its td insertion, and is now functional. As a consequence, cells in which successful re-targeting has taken place are Tp resistant. They may therefore be directly selected. The method was used in *Escherichia coli* cells.

Clostridial species are frequently resistant to trimethoprim, making the use of a RAM based on a Tp resistance cassette unworkable. For instance in the study of Swenson et al (1980) *Antimicrob. Agents Chemother.* 18: 13-19 the vast majority of the isolates tested were resistant. Resistance is also common in the non-pathogenic, industrially useful strains. Indeed, the intrinsic resistance of *C. cellulolyticum* forms the basis of the conjugation method used for gene transfer experiments in Jennert et al (2000) *Microbiology.* 146: 3071-80.

A kit for performing gene knockouts (principally in *E. coli*) based on a RAM consisting of a kanamycin resistance ($Km^r$) cassette is marketed as "TargeTron™ Gene Knockout System" by Sigma-Aldrich. *Clostridium* spp. are naturally resistant to kanamycin, so kanamycin resistance cannot be used as a selection marker in *Clostridium.*

The inability to make defined gene knock-outs in Clostridial genomes, by reciprocal marker exchange, is a major impediment to the commercial exploitation of members of the class Clostridia, and particularly the genus *Clostridium*. It impinges on all areas. Thus, the application of metabolic engineering to generate industrial stains with improved fermentation characteristics presently cannot be contemplated (eg *C. acetobutylicum* and the Acetone-Butanol fermentation process; strains carrying chromosomally located therapeutic genes useful in cancer therapy cannot be generated (a prerequisite for clinical trials, eg *C. sporogenes* and Clostridial-Directed Enzyme Prodrug Therapy); and fundamental information on pathogenic mechanisms, an essential first step in the formulation of effective countermeasures, is being severely impaired (eg *C. difficile* and hospital-acquired infections).

The listing or discussion of a prior-published document in this specification should not necessarily be taken as an acknowledgement that the document is part of the state of the art or is common general knowledge.

The inventors have devised DNA molecules and methods which allow for the efficient insertion of DNA into the genome of *Clostridium* spp and other bacteria of the class Clostridia, thereby allowing the targeted mutation of genes in the genome.

A first aspect of the invention provides a DNA molecule comprising:
- a modified Group II intron which does not express the intron-encoded reverse transcriptase but which contains a modified selectable marker gene in the reverse orientation relative to the modified Group II intron, wherein the selectable marker gene comprises a region encoding a selectable marker and a promoter operably linked to said region, which promoter is capable of causing expression of the selectable marker encoded by a single copy of the selectable marker gene in an amount sufficient for the selectable marker to alter the phenotype of a bacterial cell of the class Clostridia such that it can be distinguished from the bacterial cell of the class Clostridia lacking the selectable marker gene; and
- a promoter for transcription of the modified Group II intron, said promoter being operably linked to said modified Group II intron; and wherein the modified selectable marker gene contains a Group I intron positioned in the forward orientation relative to the modified Group II intron so as to disrupt expression of the selectable marker; and wherein the DNA molecule allows for removal of the Group I intron from the RNA transcript of the modified Group II intron to leave a region encoding the selectable marker and allows for the insertion of said RNA transcript (or a DNA copy thereof) at a site in a DNA molecule in a bacterial cell of the class Clostridia.

Group II introns are mobile genetic elements which are found in eubacteria and organelles. In nature, they use a mobility mechanism termed retrohoming, which is mediated by a ribonucleoprotein (RNP) complex containing the intron-encoded reverse transcriptase (IERT) and the excised intron lariat RNA. It is believed that the excised intron RNA inserts directly into one strand of a double-stranded DNA target site by a reverse splicing reaction, while the IERT also site-specifically cleaves the opposite strand and uses the 3'-end of the cleaved strand for target DNA-primed reverse transcription (TPRT) of the inserted intron RNA. As a result, the intron (and any nucleic acid carried in a modified intron) are inserted into the target DNA. The TPRT system requires only the IERT and the excised intron RNA (see Saldanha et al (1999) *Biochemistry* 38, 9069-9083). Details of Group II introns are found in Karberg et al (2001) *Nature Biotechnology* 19, 1162-1167, incorporated herein by reference, and in references cited therein.

The IERT is also known in the art as the intron-encoded protein (IEP). The IEP (IERT) has reverse transcriptase activity as well as endonuclease and maturase activities which allow a copy of the intron to be inserted into DNA.

The process of cleaving the DNA substrate and inserting nucleic acid molecules involves base pairing of the Group II intron RNA of the RNP complex to a specific region of the DNA substrate. Additional interactions occur between the intron-encoded reverse transcriptase and regions in the DNA substrate flanking the recognition site. Typically, the Group II intron RNA has two sequences, EBS1 and EBS2, that are capable of hybridizing with two intron RNA-binding sequences, IBS1 and IBS2, on the top strand of the DNA substrate. Typically, the Group II intron-encoded reverse transcriptase binds to a first sequence element and to a second sequence element in the recognition site of the substrate. Typically, the Group II intron RNA is inserted into the cleavage site of the top strand of the DNA substrate. The first sequence element of the recognition site is upstream of the putative cleavage site, the IBS1 sequence and the IBS2 sequence. The first sequence element comprises from about 10 to about 12 pairs of nucleotides. The second sequence element of the recognition site is downstream of the putative cleavage site and comprises from about 10 to about 12 nucleotides.

As denoted herein, nucleotides that are located upstream of the cleavage site have a (−) position relative to the cleavage site, and nucleotides that are located downstream of the cleavage site have a (+) position relative to the cleavage site. Thus, the cleavage site is located between nucleotides −1 and +1 on the top strand of the double-stranded DNA substrate. The IBS1 sequence and the IBS2 sequence lie in a region of the recognition site which extends from about position −1 to about position −14 relative to the cleavage site.

Typically, EBS1 is located in domain I of the Group II intron RNA and comprises from about 5 to 7 nucleotides that are capable of hybridizing to the nucleotides of the IBS1 sequence of the substrate.

Typically, EBS2 is located in domain I of the Group II intron RNA upstream of EBS1 and comprises from about 5 to 7 nucleotides that are capable of hybridizing to the nucleotides of IBS2 sequence of the substrate.

In order to cleave the substrate efficiently, it is preferred that the nucleotide or sequence, which immediately precedes the first nucleotide of EBS1 of the Group II intron RNA, be complementary to the nucleotides at +1 in the top strand of the substrate.

The modified Group II intron contained in the DNA molecule of the invention does not express the IERT. Preferably, the Group II intron does not contain a functional open reading frame for the IERT. Preferably, domain IV of the Group II intron, which typically contains the IERT is partially deleted such that it does not contain the IERT.

Various Group II introns which may be useful in the practice of the invention are known. These include bacterial introns such as the eubacterial introns reviewed in Dia and Zimmerly (2002) *Nucleic Acids Res.* 30: 1091-1102, and also include mitochondrial and chloroplast introns referred to in Zimmerly, Hausner and Wu (2001) *Nucleic Acids Res.* 29: 1238-1250. It is preferred if the Group II intron is the *Lactococcus lactis* L1.LtrB intron (Mohr et al (2000) supra). The IERT in this Group II intron is the LtrA protein. The aI1 and aI2 nucleotide integrases of *Saccharomyces cerevisiae* are also suitable.

Another alternative is the Group II intron from the clostridial conjugative transposon Tn5397 (Roberts et al (2001) *J. Bacteriol.* 183: 1296-1299).

The LtrA RNP complex comprises an excised, wild-type or modified excised Group L1.LtrB Group II intron RNA of the *Lactococcus lactis* LtrB gene, hereinafter referred to as the "L1.LtrB intron" RNA, and a wild-type or modified L1.LtrB intron-encoded reverse transcriptase, referred to as the LtrA protein. The EBS1 of the L1.LtrB intron RNA comprises 7 nucleotides and is located at positions 457 to 463. The EBS1 sequence of the wildtype L1.LtrB intron RNA has the sequence 5'-GUUGUGG (SEQ ID No. 1). The EBS2 of the L1.LtrB intron RNA comprises 6 nucleotides and is located at positions 401 to and including 406. The EBS2 sequence of the wild-type L1.LtrB intron RNA has the sequence 5'AUGUGU (SEQ ID No. 2).

The Group II intron in the DNA molecule of the invention has been modified to include a modified selectable marker gene. A selectable marker gene is any gene which confers an altered phenotype in a bacterial cell in which it is expressed, compared to the bacterial cell in which it is not expressed. The modified selectable marker gene is modified (compared to the unmodified selectable marker gene) by containing a Group I intron which disrupts the expression of the selectable marker. The term "unmodified selectable marker gene" includes a gene comprising a promoter and a coding region of a gene, where the promoter is not the promoter of the naturally occurring gene. "Unmodified selectable marker" also includes where the promoter is the promoter of the naturally occurring gene. Further details of the modification of the selectable marker gene are described below but, in essence, the presence of the Group I intron prevents the expression of the selectable marker but, upon excision of the Group I intron, the resulting nucleic acid (ie unmodified selectable marker gene) is able to express the selectable marker. Preferably, the selectable marker gene is located in domain IV of the Group II intron.

It will be appreciated that the Group I intron may be positioned at any location within the selectable marker gene as long as expression of the selectable marker is prevented by the presence of the Group I intron. It will be appreciated that the Group I intron may be positioned, for example, within the promoter, such as between the −10 and −35 elements of the promoter, between the promoter and the coding region or in the coding region.

The selectable marker gene containing the Group I intron (ie the modified selectable marker gene) may be considered to be a retrotransposition activated marker (RAM).

Group I introns are self-splicing introns which may or may not require auxiliary factors such as proteins in order to be excised. Various Group I introns which may be useful in the practice of the invention are known including bacteriophage introns (Sandegran and Sjöberg (2004) *J. Biol. Chem.* 279: 22218-22227), and Tetrahymena Group I intron (Roman (1998) *Biochem.* 95: 2134-2139). It is preferred that the Group I introns do not require auxiliary factors in order to be excised. It is preferred if the Group I intron is the td Group I intron from Phage T4 (EhrenMan et al (1986) *Proc. Natl. Acad. Sci. USA* 83: 5875-5879).

It will be appreciated that the orientation of the various components within the DNA molecule is very important. Thus, from FIG. 2 it will be seen that the modified selectable marker gene is present within the Group II intron in the reverse orientation to the Group II intron. Also, the Group I intron which is present within the modified selectable marker gene in a reverse orientation to the selectable marker gene but in the same forward orientation as the Group II intron. If the Group I intron were in the same orientation as the selectable marker gene, the intron would be able to excise from the mRNA transcript of the selectable marker gene and the phenotype conferred by the selectable marker would be present irrespective of whether the Group II intron containing the selectable marker had retargeted to the chromosome. Therefore, the Group I intron and the selectable marker gene must be in opposite orientations.

If the selectable marker gene were in the same orientation as the Group II intron, following the above logic, the Group I intron would have to be in the opposite orientation to the Group II intron. However, in this orientation, it would not excise from the mRNA trancript and so, even if the Group II intron did retarget to the chromosome, there would be no selectable phenotype.

Only when the various components are orientated as shown in FIG. 2 will retargeting of the Group II intron to the chromosome be necessary and sufficient for expression of the selectable marker phenotype.

When the DNA molecule of the invention is used to introduce a nucleic acid molecule into a site of a DNA molecule in a bacterial cell of the class Clostridia (as is described in more detail below), the Group I intron is removed from the RNA transcript produced from the modified Group II intron to leave a region encoding the selectable marker, and the RNA transcript (or a DNA copy thereof) is introduced into a site in a DNA molecule in a bacterial cell of the class Clostridia. In this way, the nucleic acid introduced into a DNA molecule in a bacterial cell of the class Clostridia has a selectable marker gene which is able to express the selectable marker in the bacterial cell.

In a preferred embodiment, the modified Group II intron is flanked by exons, which exons allow splicing of an RNA transcript of the Group II intron.

The promoter of the selectable marker gene is capable of causing expression of the selectable marker when it is encoded by a single copy of the selectable marker gene in an amount sufficient for the selectable markers to alter the phenotype of a bacterial cell of the class Clostridia such that it can be distinguished from the bacterial cell of the class Clostridia lacking the selectable marker gene. For example, the promoter may be one which, when present in a single copy in the bacterial chromosome, and when in operable linkage with the coding region of the selectable marker, expresses the selectable marker in a detectable amount. The promoter of the selectable marker gene is one which is functional in a bacterial cell of the class Clostridia and causes adequate expression when present in a single copy as described above. It is preferred that the promoter is functional in a *Clostridium* sp. Suitable promoters include the fdx gene promoter of *C. perfringens* (Takamizawa et al (2004) *Protein Expression Purification* 36: 70-75); the ptb, thl and the adc promoters of *C. acetobutylicum* (Tummala et al (1999) *App. Environ. Microbiol.* 65: 3793-3799) and the cpe promoter of *C. perfringens* (Melville, Labbe and Sonenshein (1994) *Infection and Immunity* 62: 5550-5558) and the thiolase promoter from *C. acetobutylicum* (Winzer et al (2000) *J. Mol. Microbiol. Biotechnol.* 2: 531-541). Preferably, the promoter of the selectable marker gene is the promoter of the thl gene of *C. acetobutylicum*.

To test whether a promoter is likely to be effective as a promoter of a selectable marker of the invention, a spliced variant of the RAM (ie encoding the selectable marker since the Group I intron has been removed) may be placed under its transcriptional control and introduced into the Clostridia to be targeted at a low copy number, preferably equivalent to the copy number of the chromosome. This can be achieved by using a low copy number plasmid, such as the low copy number derivatives of plasmid pAMβ1 described in Swinfield et al (1990) *Gene.* 87:79-90 or more ideally using a conjugative transposon and the method described in Mullany et al (*Plasmid* (1994) 31: 320-323) and Roberts et al (*J Microbiol Methods* (2003) 55: 617-624). To achieve the latter, the spliced RAM together with the promoter under evaluation may be cloned into a vector that is unable to replicate in a Gram-positive bacterium but which carries an antibiotic resistance gene (eg catP) and a segment of DNA derived from a conjugative transposon, such as Tn916. The plasmid is then transformed into a *Bacillus subtilis* cell that carries the appropriate conjugative transposon in its genome (Tn916), and transformants selected on plates containing chloramphenicol. As the plasmid cannot replicate, the only way that chloramphenicol resistant colonies can arise is if the plasmid integrates into the genome as a consequence of homologous recombination between Tn916 and the region of homology carried by the plasmid. This results in a transposon::plasmid cointegrate carrying the spliced RAM and promoter under test that is located in a single copy in the genome. The *Bacillus subtilis* transconjugant obtained may now be used as a donor in a conjugation with the Clostridia to be targeted. In these matings, transfer of the transposon:: plasmid cointegrate into the Clostridia recipient can be selected on the basis of acquisition of resistance to thiamphenicol. Once obtained, transconjugants may be tested for the resistance encoded by the RAM, eg., erythromycin.

The promoter for regulating the transcription of the modified Group II intron may be any suitable promoter which is functional in a bacterial cell of the class Clostridia. The promoter may be a constitutive promoter or an inducible promoter. An inducible promoter may be derepressed such that it drives expression in a constitutive fashion. In particular experiments described in the Examples, the inventors found that regulated expression of the modified Group II intron confers no advantage in allowing for a high intron insertion frequency compared to constitutive expression. However, in other situations, it may be useful to be able to regulate expression of the modified Group II intron. A person of ordinary skill can perform experiments to determine whether a particular promoter is suitable to allow for a satisfactory intron insertion rate.

Girbal et al (2003) *Appl. Environ. Microbiol.* 69: 4985-4988 describe a preferred xylose-inducible promoter in *C. acetobutylicum*, which is based on the *Staphylococcus xylosus* xylose operon promoter-repressor regulatory system. Suitable inducible promoters are IPTG or xylose-inducible. Conveniently, for example when the DNA molecule is for use in Clostridial cells, the promoter is the promoter region of the *C. pasteurianum* ferredoxin gene under the control of the lac operator region of the *E. coli* lac operon. Conveniently, the DNA molecule further comprises the lacI gene of *E. coli*.

A promoter for regulating the transcription of the modified Group II intron may be a constitutive promoter. The skilled person will appreciate that in general all promoters are regulated under one condition or another, even if such conditions are not known. Therefore, we intend "constitutive promoter" to be interpreted broadly to encompass a promoter that is active in the Clostridial cells under the normal culture conditions employed in the retargeting protocol, without the need for addition of an agent to activate expression driven by the promoter. Promoters of genes that are essential to primary metabolism may be suitable "constitutive promoters". For example, the thiolase promoter, thl, described in the Examples may be a suitable promoter. Other suitable promoters are the *C. acetobutylicum* promoters hbd, crt, etfA, etfB amd bcd (Alsaker and Papoutsakis (2005) *J Bacteriol* 187:7103-7118). Promoters suggested as being suitable for driving expression of the modified selectable marker in the RAM may also be suitable.

The use of an inducible promoter allows transcription of the Group II intron containing the selectable marker gene interrupted by the Group I intron (which may be termed a RAM) to be switched off following retargeting of the RAM to the bacterial chromosome. When the RAM is transcribed from the inducible promoter, expression of the selectable marker is ineffective. This may be because of duplex formation between the transcripts of the coding strand transcribed from the chromosome and the non-coding strand transcribed from the DNA molecules.

The DNA molecule of the invention preferably is capable of replication in a bacterial cell of the class Clostridia. More preferably, it is capable of conditional replication. Conveniently, the DNA molecule contains a suitable origin of replication and any necessary replication genes to allow for replication in the Gram-positive bacterial cell (ie suitable rep genes). Preferably, the DNA is a plasmid. Alternatively, the DNA may be linear or it may be filamentous phage like M13. Conveniently, the DNA molecule is a shuttle vector which allows for replication and propagation in a Gram-negative bacterial cell such as *Escherichia coli* and for replication in a Gram-positive cell, particularly a cell of the class Clostridia and more particularly of the genus *Clostridium*. Additionally or alternatively, the DNA molecule of the invention contains a region which permits conjugative transfer from one bacterial cell to a bacterial cell of the class Clostridia. It is particularly preferred if the DNA molecule contains a region which permits conjugative transfer between *E. coli* and a bacterium of the class Clostridia, and more particularly of the genus *Clostridium*. For example, the DNA molecule may contain the oriT (origin of transfer) region, including the traJ gene.

Methods of transformation and conjugation in Clostridia are provided in Davis, I, Carter, G, Young, M and Minton, N P (2005) "Gene Cloning in Clostridia", In: Handbook on Clostridia (Durre P, ed) pages 37-52, CRC Press, Boca Raton, USA.

The selectable marker may be any suitable selectable marker which can be expressed in and used to select a cell of the class Clostridia containing the selectable marker. Suitable selectable markers include enzymes that detoxify a toxin, such as prodrug-converting enzymes. Selectable markers also include a prototrophic gene (for use in a corresponding auxotrophic mutant). Preferably, the selectable marker is one which gives a growth advantage to the bacterial cell of the class Clostridia in which it is expressed. Thus, typically, under a given growth condition the bacterial cell which expresses the selectable marker is able to grow (or grow more quickly) compared to an equivalent cell that does not express the selectable marker.

Convenient selectable markers include antibiotic resistance factors. Thus, suitably, the selectable marker gene is a gene which confers antibiotic resistance on a bacterial cell of the class Clostridia.

Not all antibiotic resistance genes can be used in all cells of the class Clostridia. For example, *Clostridium* sp. are naturally resistant to kanamycin, and are frequently resistant to trimethoprim. Thus, it is preferred that the selectable marker gene is not a kanamycin resistance gene or a trimethoprim resistance gene particularly when the bacterial cell is of the genus *Clostridium*. Suitable antibiotic resistance genes for use in Clostridial cells, such as *Clostridium* sp., include erythromycin resistance genes (such as Erm) and chloramphenicol resistance genes (such as catP). Another suitable antibiotic resistance gene is tetM, for example tetM from the *Enterococcus faecalis* Tn916 conjugative transposon (Roberts et al (2001) *Microbiol.* 147: 1243-1251). Another suitable antibiotic resistance gene, widely used in bacteria of the class Clostridia, is spectinomycin adenyltransferase, aad (Charpentier et al (2004) *Appl. Environ. Microbiol.* 70, 6076-6085).

The methods and DNA molecules of the invention may also be used to investigate genes the function of which is not known. For example, the DNA molecule of the invention may be adapted to contain a unique oligonucleotide sequence referred to as a tag which will be introduced into the DNA in the cell of the class Clostridia. Conveniently, a plurality of DNA molecules of the invention are produced, each containing a different tag sequence. When the DNA inserts into the bacterial chromosome, the tag is present in the genomic DNA and may be detected for example by amplification by hybridising to a labelled oligonucleotide probe, a portion of which has a sequence complementary to a portion of the tag. Suitable tags, probes and methods of amplifying and hybridising are described in Hensel et al (1995) *Science* 269: 400-403. A plurality of mutants may be generated by the method of the invention in which each has the DNA inserted into a different gene, and each may be identified by its unique tag. Typically, each different retargeting nucleic acid contains targeting portions which direct it to a different gene in the DNA of the cell of the class Clostridia. The plurality of mutants may be introduced into an environment for a period of time. Mutants may then be recovered from the environment. The ability of individual tags to be detected in the recovered pool of mutants gives an indication of whether a particular mutant has been able to grow or survive as well as other mutants. In this way, genes that are required for growth or survival in the environment may be identified. Hensel et al (1995; supra) used a similar approach to identify virulence genes in *Salmonella.*

In a modification of the above method, DNA molecules of the invention having the same tag but different randomised Group II intron targeting portions and corresponding exon sequences may be generated, pooled and used to make bacterial mutants. Group II introns with randomised targeting portions are described in WO 01/29059. Many of the DNA molecules may be unable to insert anywhere in the bacterial genome. However, some may be able to insert at an unknown location in the bacterial genome governed by the sequence of the targeting portions. A sufficiently large pool of DNA molecules of the invention may be used in the method such that one or more colonies are obtained in which the DNA has inserted into the chromosome. A single clone may be selected. The process may be repeated for a pool of DNA molecules of the invention having a different unique tag, to obtain another single mutant bacterial clone with a unique tag. In this way, a plurality of bacterial mutants, each with a unique tag are generated. The plurality of mutants may be exposed to an environment as described above, to identify particular mutants that are compromised for growth or survival in that environment. A mutant identified from such a screen may then be characterised to determine in which gene the DNA has inserted.

Further details of genes encoding modified selectable markers which contain a Group I intron which disrupts the expression of the selectable marker are given below.

The selectable marker gene or its coding region may be associated with regions of DNA for example flanked by regions of DNA that allow for the excision of the selectable marker gene or its coding region following its incorporation into the chromosome. Thus, a clone of a mutant Clostridial cell expressing the selectable marker is selected and manipulated to allow for removal of the selectable marker gene. Recombinases may be used to excise the region of DNA. Typically, recombinases recognise particular DNA sequences flanking the region that is excised. Cre recombinase or FLP recombinase are preferred recombinases. Alternatively, an extremely rare-cutting restriction enzyme could be used, to cut the DNA molecule at restriction sites introduced flanking the selectable marker gene or its coding region. A preferred restriction enzyme is I-SceI.

A mutant bacterial cell from which the selectable marker gene has been excised retains the Group II intron insertion. Accordingly, it has the same phenotype due to the insertion with or without the selectable marker gene. Such a mutant bacterial cell can be subjected to a further mutation by the method of the invention, as it lacks the selectable marker gene present in the RAM.

Although the modified Group II intron in the DNA molecule of the invention does not express the IERT, conveniently the DNA molecule contains in another location a gene which is able to express the IERT.

Where the Clostridial cell into which the Group II intron is to be inserted uses a different genetic code from the Group II intron and its associated Group II intron-encoded reverse transcriptase, it is preferred that the sequence of the Group II intron-encoded reverse transcriptase is modified to comprises codons that correspond to the genetic code of the host cell.

A particularly desirable embodiment of the invention is wherein the modified Group II intron comprises targeting portions. Typically, the targeting portions allow for the insertion of the RNA transcript of the modified Group II intron into a site within a DNA molecule in the Clostridial cell. Typically, the site is a selected site, and the targeting portions of the modified Group II intron are chosen to target the selected site. In a preferred embodiment, the selected site is in the chromosomal DNA of the Clostridial cell. Typically, the selected site is within a particular gene, or within a portion of DNA which affects the expression of a particular gene. Insertion of the modified Group II intron at such a site typically disrupts the expression of the gene and leads to a change in phenotype.

Genes may be selected for mutation for the purposes of metabolic engineering. For example, in organisms such as *Thermoanaerobacterium saccharolyticum*, or other members of the class Clostridia which have a similar metabolism, deletion of lactate dehyrogenase and phosphotransacetylase to prevent formation of lactate and acetate, respectively, could be used to elevate levels of ethanol (Desai et al, (2004) *Appl Microbiol Biotechnol.* 65: 600-5). In solventogenic clostridia, such as *Clostridium acetobutylicum* and *Clostridium beijerinckii*, specific deletions may be made to the genes encoding the enzymes responsible for solvent and acid production as a means of maximising acetone and butanol (see Jones and Woods (1986) *Microbiol Rev.* 50: 484-524). Thus, strains could be generated that produce only acetone or butanol, by elimination of enzymes responsible for production of acetate (phosphotransacetylase and or acetate kinase), butyrate (phosphotransbutyrylase and or butyrate kinase), butanol (butanol dehydrogenase A and/or butanol dehydrogenase B) and/or acetone (acetyoacetate decarboxylase and/or acetoacetyl-CoA transferase). Moreover, the fermentative ability of such strains could be extended by gene addition into the chromosome, such that new substrates could be degraded (sugars, lignocellulose, hemicellulose, etc.) and/or new end products made (isopropanol, 1,3-propanediol, etc.).

Genes may be selected for mutation in order to determine the role of their encoded products in virulence, a prerequisite to the development of vaccines and other countermeasures. In *C. difficile*, for example, the relative roles of toxin A and toxin B (CdtA and CdtB) remain to be established (Bongaerts and Lyerly (1994) *Microbial Pathogenesis* 17: 1-12) due to a previous inability to generate isogenic mutants. Certain strains (Perelle et al (1994) *Infect Immun.* 65:

1402-1407) also produce an actin-specific ADP-ribosyltransferase CDT (CdtA and CdtB). Other factors undoubtedly contribute to virulence, particularly the initial colonisation process. The participation of a number of gene products has been proposed (Tasteyre et al (2001) *Infect Immun* 69: 7937-7940; Calabi et al (2002) *Infect Immun* 70: 5770-5778; Waligora et al (2001) *Infect Immun* 69: 2144-2153), including those involved in adhesion, the S-layer proteins (SplA) and motility (FliC and FliD). Definitive proof of the involvement of these factors in disease through the generation of mutants has until now not been possible.

The DNA sequences of the genomes of many bacteria of the class Clostridia are known. For example, the DNA sequences of the genomes of *C. acetobutylicum* (ATCC 824 (GenBank Accession No AE001437), *C. difficile* (GenBank Accession No AM180355), *C. tetani* E88 (GenBank Accession No AE015927) and *C. perfringens* strain 13 (GenBank Accession No BA000016) and *C. botulinum* are known. The sequence of a *C. sporogenes* genome is partially known and is very similar to the sequence of the *C. botulinum* genome. From this information, sites for insertion are readily identified, for example within open reading frames. It is preferred if the DNA molecule of the invention contains a modified Group II intron which contains targeting portions which targets the RNA transcript of the modified Group II intron (or a DNA copy thereof) into a gene in the genome of one of these bacterial species.

As described above, Group II introns naturally contain regions which target the intron to a specified sequence in target DNA. Because the recognition site of the DNA substrate is recognized, in part, through base pairing with the excised Group II intron RNA of the RNP complex, it is possible to control the site of nucleic acid insertion within the DNA substrate. This may be done by modifying the EBS 1 sequence, the EBS2 sequence or the δ sequence, or combinations thereof. Such modified Group II introns produce RNP complexes that can cleave DNA substrates and insert nucleic acid molecules at new recognition sites in the genome. For example, by reference to the L1.LtrB Group II intron of *Lactococcus lactis* illustrated in FIGS. 1A and 1B the EBS1, EBS2 and δ are modified to permit base pairing of the RNA transcript of the modified Group II intron with a target site. Rules for DNA target-site recognition by L1.LtrB Group II intron which enable retargeting of the intron to specific DNA sequences are described in Mohr et al (2000) *Genes & Development* 14, 559-573, incorporated herein by reference. Computer-aided design of targeting portions are also described in Perutka et al (2004) *J. Mol. Biol.* 336, 421-429, incorporated herein by reference.

WO 01/29059 to the Ohio State University Research Foundation, incorporated herein by reference, describes a selection-based approach in which the desired DNA target site is cloned into a recipient vector upstream of a promoterless $tet^R$ gene. Introns that insert into that site are selected from a combinatorial donor library having randomized targeting portions (EBS and δ) and IBS exon sequences. The modified L1.LtrB intron contains a heterologous promoter, such that when it inserts into the target site in the recipient vector, the $tet^R$ gene is transcribed and the bacterial cell containing the vectors may be selected for. The sequence of the modified intron may be determined by PCR. Thus, a modified Group II intron DNA may be isolated that allows for insertion into the target DNA site within a Clostridial cell.

In the case of the L1.LtrB Group II intron, it is thought that the interaction of the δ region with a 5' region of the target DNA is not critical to efficient retrohoming of the Group II intron. However, the interactions between EBS2 and EBS1 in the intron RNA and IBS2 and IBS1 in the target DNA are more important.

When the Group II intron excises from the RNA transcript, it is believed that it transiently base pairs with portions of the flanking exon RNA. In particular, the EBS2 and EBS1 regions base-pair with the IBS2 and IBS1 regions of the 5' exon respectively. Therefore, it is preferred that the IBS2 and IBS 1 region of the 5' exon is modified so as to promote base-pairing with the modified EBS2 and EBS1 regions of the intron RNA. This facilitates efficient excision of the Group II intron from its RNA trancript.

Modification of the EBS2 and EBS1δ sites and the IBS2 IBS1 site may conveniently be performed using any suitable site directed mutagenesis methods known in the art, for example oligonucleotide-directed mutagenesis or PCR-based methods.

Typically, the DNA molecule of the invention is able to express an antibiotic resistance marker which is different to the selectable marker. For example, if the selectable marker gene is a first antibiotic resistance gene the DNA includes a second antibiotic resistance gene. It is particularly preferred if both antibiotic resistance genes are ones which give rise to antibiotic resistance in Clostridial cells. For example, the selectable marker gene in the DNA molecule may be an erythromycin resistance gene and the DNA molecule may further contain a chloramphenicol resistance gene (or vice versa). When the DNA molecule is for use in a *Clostridium* sp. it is particularly preferred that any antibiotic resistance genes are selected from erythromycin resistance genes (eg ermB) or chloramphenicol resistance genes (eg catP).

It will be appreciated that although it is convenient for the DNA molecule of the invention to itself contain a gene which is able to express the IERT, this may be provided on a separate DNA molecule. Thus, a further aspect of the invention provides a kit of parts comprising a DNA molecule of the first aspect of the invention and a separate DNA molecule which is able to express the IERT. Typically, the DNA molecules are plasmids, preferably compatible plasmids. It will be appreciated that the kit may further contain a DNA molecule (typically a plasmid) which is able to express the lac repressor protein. This is useful in the situation where the DNA molecule of the invention comprises an IPTG-inducible promoter which is operatively linked to the Group II intron, but when the DNA molecule of the invention does not include the lacI gene.

A third aspect of the invention provides a method of introducing a nucleic acid molecule into a site of a DNA molecule in a bacterial cell of the class Clostridia, the method comprising the steps of:
  (i) providing a bacterial cell of the class Clostridia with the DNA molecule of the invention and a DNA molecule capable of expressing a Group II intron-encoded reverse transcriptase; and
  (ii) culturing the bacterial cell under conditions which allow for removal of the Group I intron from the RNA transcript of the modified Group II intron and the insertion of said RNA transcript containing the selectable marker gene (or a DNA copy thereof) into said site.

Preferably, the bacterial cell of the class Clostridia is cultured under conditions which allow for expression of the selectable marker. Typically, the bacterial cell of the order Clostridia into which nucleic acid has been introduced at a site of a DNA molecule within the cell (ie mutated cell) is selected based on an altered phenotype conferred by the selectable marker.

Conveniently, the selectable marker is an antibiotic resistance marker and the mutated Clostridial cell is selected on the basis of its ability to grow in the presence of the relevant antibiotic.

Conveniently, the selected cell is cloned and a single clone of cells is obtained.

A further aspect of the invention provides a method of targeting a nucleic acid molecule to a selected site of a DNA molecule in a bacterial cell of the class Clostridia, the method comprising providing a bacterial cell of the class Clostridia with a DNA molecule of the invention in which the modified Group II intron comprises targeting portions and a DNA molecule capable of expressing a Group II intron-encoded reverse transcriptase; and culturing the bacterial cell under conditions which allow removal of the Group I intron from the RNA transcript of the modified Group II intron and the insertion of said RNA transcript (or DNA copy thereof) containing the selectable marker gene into said selected site.

It will be appreciated that in this way it is possible to make site directed mutations in DNA (such as the genome) of a bacterial cell of the class Clostridia, such as a *Clostridium* spp.

Mutant bacterial cells of the class Clostridia obtained by the methods of the invention are also part of the invention.

It will be appreciated that with respect to all aspects of the invention it is preferred that the bacterial cell of the class Clostridia is a *Clostridium* spp. It is particularly preferred if the Clostridial cell is *C. thermocellum* or *C. acetobutylicum* or *C. difficile* or *C. botulinum* or *C. perfringens* or *C. sporogenes* or *C. beijerinckii* or *C. tetani* or *C. cellulyticum* or *C. septicum*. The Clostridial cell may alternatively by *Thermoanaerobacteria saccharolyticum*, an important species for industrial ethanol production. By the term "Clostridia", we also include *Roseburia*, such as *Roseburia intestinalis*, which is a probiotic bacterium. Thus, preferably, the selectable marker gene in the DNA molecule of the invention is a gene which can be used for selection in these species (eg an erythromycin resistance gene or a chloramphenicol resistance gene or a tetracycline resistance gene or a spectinomycin resistance gene). Also preferably, the DNA molecules of the invention contain origins of replication and any necessary replication genes which allow for replication in these bacterial species.

A particular feature of the invention is that the modified selectable marker gene is one which contains a Group I intron which disrupts expression of the selectable marker. The selectable marker is one which may be expressed in and used for selection in a bacterial cell of the class Clostridia, particularly a *Clostridium* cell.

It is particularly preferred that the selectable marker is an antibiotic resistance gene which can be used for selection in a *Clostridium* spp.

A further aspect of the invention provides a DNA molecule comprising a modified erythromycin-resistance gene which contains a Group I intron.

A further aspect of the invention provides a DNA molecule comprising a modified chloramphenicol-resistance gene which contains a Group I intron.

A further aspect of the invention provides a DNA molecule comprising a modified tetracycline-resistance gene which contains a Group I intron.

A further aspect of the invention provides a DNA molecule comprising a modified spectinomycin resistance gene which contains a Group I intron.

The invention also includes these DNA molecules present in a host cell, for example an *E. coli* cell or a cell of the class Clostridia.

Preferably the Group I intron is present in the opposite orientation to the antibiotic resistance gene.

The Group I intron may be present anywhere within the antibiotic resistance gene, for example within the coding region thereby disrupting translation, or upstream of the coding region thereby disrupting transcription or translation.

The Group I intron is present within the antibiotic resistance gene in a form whereby when the intron is transcribed it is able to excise (splice) itself from the RNA transcript.

Any autocatalytic RNA which can self-splice out of a larger RNA in an orientation-dependent manner could substitute for a Group I intron in the present invention. Suitably, an "IStron" may be used, which is believed to be a fusion of a Group I intron and an IS element (Haselmayer et al (2004) *Anaerobe* 10: 85-92; Braun et al (2000) *Mol. Microbiol.* 36: 1447-1459).

For the avoidance of doubt, for the purposes of all aspects of the invention any autocatalytic RNA which can self-splice out of a larger RNA in an orientation-dependent manner is considered to be a Group I intron, whether or not it requires auxiliary factors. Preferably the Group I intron does not require auxiliary factors.

It is preferred that the Group I intron does not encode an intron-encoded protein such as an intron-encoded reverse transcriptase. This feature prevents the excised Group I intron RNA from re-inserting at another site within the bacterial genome.

It is noted that, typically, the splicing of Group I introns (such as the td intron of Phage T4) is reliant on exon sequences flanking the point of insertion. Thus, the modified selectable marker genes of the invention (and in particular the modified antibiotic resistance genes which encode erythromycin resistance and chloramphenicol resistance and tetracycline resistance and spectinomycin resistance of this aspect of the invention) contain the Group I intron inserted in a position whereby it is flanked by suitable exon sequences that allow the Group I intron to splice out of the RNA transcript and wherein the resulting spliced transcript (or DNA copy thereof) encodes a functional selectable marker (such as functional erythromycin resistance or functional chloramphenicol resistance). Suitable flanking sequences are known for Group I introns. For example, for the Phage T4 td Group I intron, the intron is typically preceded by a G residue (ie present 5' of the intron) and the intron is typically followed by the sequence 5'-ACCCAAGAGA-3' (SEQ ID No. 3) (ie present 3' of the intron). Alternatively, the intron may be followed by the sequence 5'-ACCCAAGAA-3' (SEQ ID No. 4).

In a preferred embodiment of the invention, the coding region of the selectable marker (such as the erythromycin or chloramphenicol or tetracycline or spectinomycin resistance genes) contains suitable sequences which flank the intron. In relation to the td intron, and the combined 5' and 3' flanking sequence 5'-GACCCAAGAGA-3' (SEQ ID No. 5) this is able to code for several amino acid sequences depending on the reading frame (as explained in more detail in the examples).

In Frame 1, it encodes the amino acid sequence DPRD/E (SEQ ID No. 6); in Frame 2 it encodes the amino acid sequence R/GPKR (SEQ ID No. 7) and in Frame 3 it encodes the amino acid sequence "X"TQE"Z" (SEQ ID No. 8) where X can be any of G, E, A, V, L, S, W, P, Q, R, M, T or K and "Z" can be any of K, S, R, I, M, T or N.

Thus, in a preferred embodiment, the coding region of the selectable marker gene encodes a portion of peptide with the above amino acid sequence.

In a further preferred embodiment, the exon sequence 3' of the intron is present in an appropriate reading frame at the 5' end of the coding sequence of the selectable marker so that, in the absence of the intron, the coding sequence encodes a functional selectable marker which contains a linker peptide at the N-terminus of the selectable marker polypeptide.

The linker peptide is typically a peptide of 4 to 20, preferably 4 to 15, typically 4, 5, 6, 7, 8, 9, 10, 11, 12, 13, 14 or 15 amino acid residues, a portion of which are encodable by the exon coding sequences flanking the intron. The presence of the linker peptide does not interfere substantially with antibiotic resistance activity. In other words, the polypeptide produced from expression of the nucleic acid molecule produced when the Group I intron has been excised has antibiotic resistance activity.

Alternatively, the Group I intron flanking sequence may be disposed so that the insertion of the Group I intron disrupts transcription of the selectable marker gene. For example, it may be located between the −35 and −10 elements of the promoter.

In a further alternative, the Group I intron flanking sequence may be disposed so that the insertion of the Group I intron disrupts translation of the selectable marker gene. For example, it may be located between the ribosome binding site and the start codon.

It will be appreciated that the DNA molecules of the invention may be made using standard molecular biological techniques as described in Sambrook et al, "Molecular cloning: A laboratory manual", 2001, 3$^{rd}$ edition, Cold Spring Harbor Laboratory Press, Cold Spring Harbor, N.Y.

The invention will now be described with reference to the following non-limiting Examples and Figures.

Figure 1B:
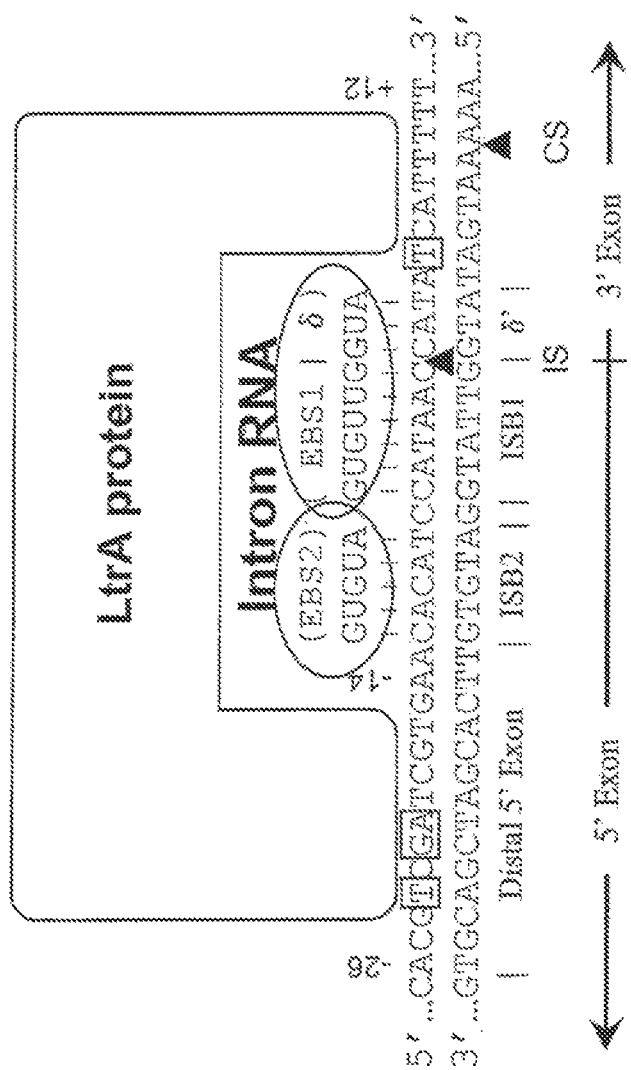

FIGS. 1A and 1B. FIG. 1A: Secondary structure model of L1.LtrB group II intron. The predicted secondary structure consists of six domains (I-VI). The EBS2/IBS2, EBS1/IBS1 and δ-δ' interactions between the intron and flanking exons in unspliced precursor RNA are indicated by broken lines. In the un-modified L1.LtrB intron, the open reading frame encoding the LtrA protein is present in the non-structural loop indicated as domain IV. FIG. 1B: Mechanism of DNA target site recognition by L1.LtrB group II intron. The LtrA protein binds to the L1.LtrB group II intron RNA forming a ribonucleoprotein complex. The intron splices out of the pre-mRNA, liberating the ribonucleoprotein as a particle. The ribonucleoprotein particle locates target DNA sequences within the cell. The target DNA sequence of the unmodified ribonucleoprotein is an intronless copy of the ltrB gene, the sequence of which is depicted (SEQ ID No. 9). The intron RNA is inserted into the insertion site within the top strand (IS). The bottom strand is then cleaved at the cleavage site (CS) and the LtrA primes from the cut DNA and reverse-transcribes the intron RNA. Host repair activities complete the integration process. Recognition of the target is mediated by a combination of interactions between LtrA and nucleotides in the target sequence, and between EBS2 and EBS1 in the intron RNA and complementary sequences IBS2 and IBS1 in the target sequence. The most important of the nucleotides recognised by the LtrA protein are indicated by grey shading.

Figure 2A:
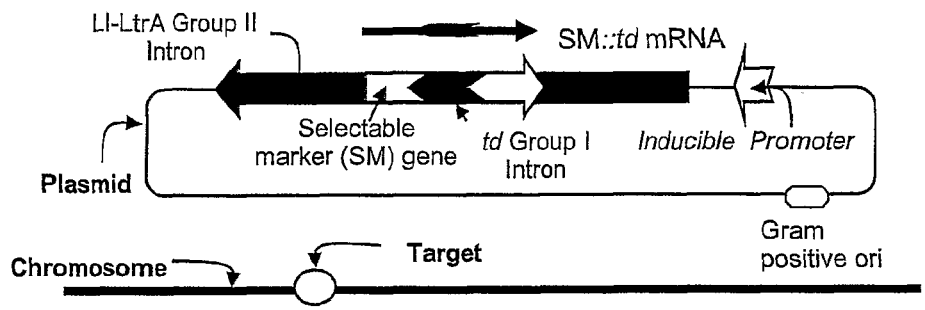
Figure 2B:
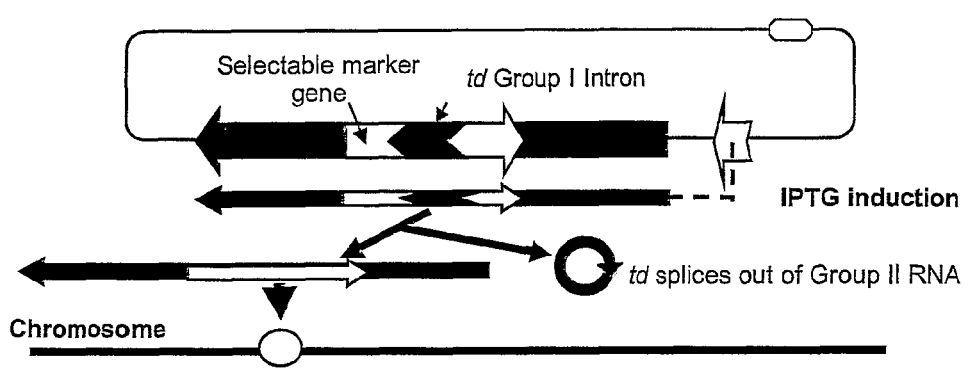
Figure 2C:
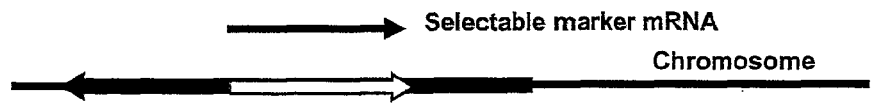

FIGS. 2A, 2B, and 2C. Positive Selection of retargeting nucleic acid-derived mutants. FIG. 2A. Transcription of the selectable marker gene from the plasmid-located retargeting nucleic acid does not result in resistance, because the mRNA produced retains the td group I intron insertion and the expression of the selectable marker gene is therefore disrupted. The td element cannot splice out of the mRNA because it has been transcribed in the wrong orientation. FIG. 2B. L1.LtrA group II intron RNA production is induced by addition of IPTG, causing transcription from Clostridial promoter fac. The td group I intron within the selectable marker gene is transcribed in the correct orientation and the td RNA splices out of the RNA produced. FIG. 2C. The L1.LtrA RNA and the selectable marker gene are inserted into the target site in the chromosome. The selectable marker gene does not contain the td group I intron and therefore the expression of the selectable marker gene is not disrupted. The cells therefore exhibit the phenotype associated with expression of the selectable marker, and may be selected accordingly.

FIGS. 3A and 3B. Inducible expression from pMTL5401Fcat in *C. sporogenes* and *C. acetobutylicum*.

FIG. 3A The *E. coli/Clostridium* shuttle plasmid pMTL5401Fcat. FIG. 3B A clone of *C. sporogenes* or (c) *C. acetobutylicum* containing pMTL5401Fcat was grown to early exponential growth phase and the CAT activity in cell lysates monitored after induction with 1 mM IPTG (■) or without induction (▲).

FIG. 4. Sequences suitable for a selectable marker gene for successful splicing of the td group I intron. The required amino acid sequences (SEQ ID Nos. 6-8, in any of the three translation reading frames, are shown above the nucleotide sequences (SEQ ID NO: 5). Amino acids at position 'X' could be either G, E, A, V, L, S, W, P, Q, R, M, T or K. At position 'Z' they could be K, S, R, I, M, T or N.

FIGS. 5A, 5B, and 5C. RAM functionality added to the ermB gene using a linker.

FIG. 5A A linker containing the td intron and its exons was inserted between the ermB ORF and its promoter (SEQ ID No. 10), preventing expression of erythromycin-resistance. Splicing of the td intron out of the reverse strand yields a modified ermB gene (SEQ ID No. 11) that encodes a functional protein with 12 additional amino acids at its N-terminus (SEQ ID No. 12). The ermB promoter of ErmB-tdRAM1 is replaced by the thl promoter in ErmBtdRAM2.

FIG. 5B PCR using various templates and primers ErmB-Pro-F3 and ErmB-R1, which flank the td intron in ErmBt-dRAM1. Lane 1: ErmBtdRAM1 DNA; Lane 2: ErmBt-dRAM1 SE DNA; Lane 3: cDNA synthesised from RNA isolated from cells containing pMTL20lacZTTErmBtdRAM1 after IPTG induction; Lane 4: the same RNA preparation before cDNA synthesis.

FIG. 5C PCR using various templates and primers Thio-F1 and ErmB-R1, which flank the td intron in ErmBt-dRAM2. Lane 1: *C. sporogenes* spo0A mutant genomic DNA; Lane 2: pMTL007::Csp-spo0A-249s plasmid DNA; Lane 3: *C. sporogenes* wild-type genomic DNA; Lane 4: water.

FIG. 6. Features and sequence of ErmBtdRAM1
ErmBtdRAM1 sequence (SEQ ID No. 13)

Figure 7:
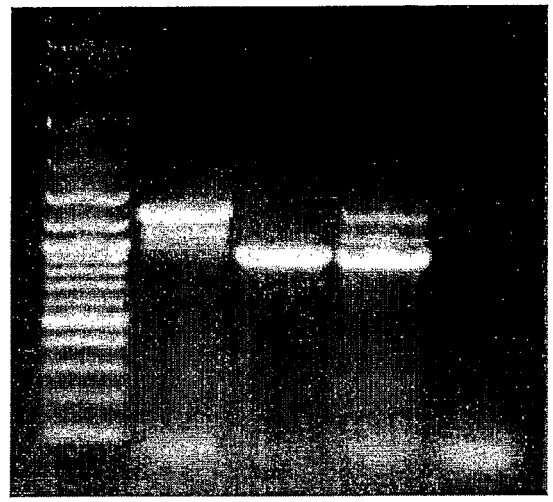

FIG. 7. Direct evidence that the ErmBtd RAM1 is spliced in *E. coli*.

To test that the td group I intron has been spliced from ErmBtdRAM1 following induction of the group II intron RNA expression, RNA was prepared from cells expressing pMTL20lacZTTErmBtdRAM1. RT-PCR was performed using primers that flank the td site of insertion. In control reactions, the same primers were used to amplify ErmBt-dRAM1 and Spliced Equivalent SE DNA by PCR. Lane 1: DNA markers; lane 2, PCR of ErmBtd RAM1; lane 3, PCR of ErmBtd RAM1 SE; lane 4, RT-PCR on total RNA from cells containing pMTL20lacZTTErmBtdRAM1, and; lane 5 RT-PCR negative control.

FIG. 8. Construction of a multicloning site in pBRR3

Sequences of the cloning sites of pBRR3-LtrB (SEQ ID No. 14) and pCR2.1-TOPO plasmids (SEQ ID No. 15). The multicloning site fragment depicted (SEQ ID No. 16, SEQ ID NO. 132) was inserted into a cleaved pBRR3-LtrB to make pBRR3-MCS1 depicted (SEQ ID No. 17), containing restriction sites found in the pCR2.1-TOPO plasmid.

FIG. 9. Sequences of the thl and thl2 promoters

Sequences of thl (SEQ ID No. 18) and thl2 promoters (SEQ ID No. 19) are shown in comparison to a consensus promoter (SEQ ID No. 20). "x" indicates a nucleotide substitution compared to the consensus sequence. The spacing between the −10 and the −35 elements is indicated for each sequence.

FIG. 10. Features and sequence of ErmBtdRAM2 ErmBtdRAM2 sequence (SEQ ID No. 21)

Figure 11:
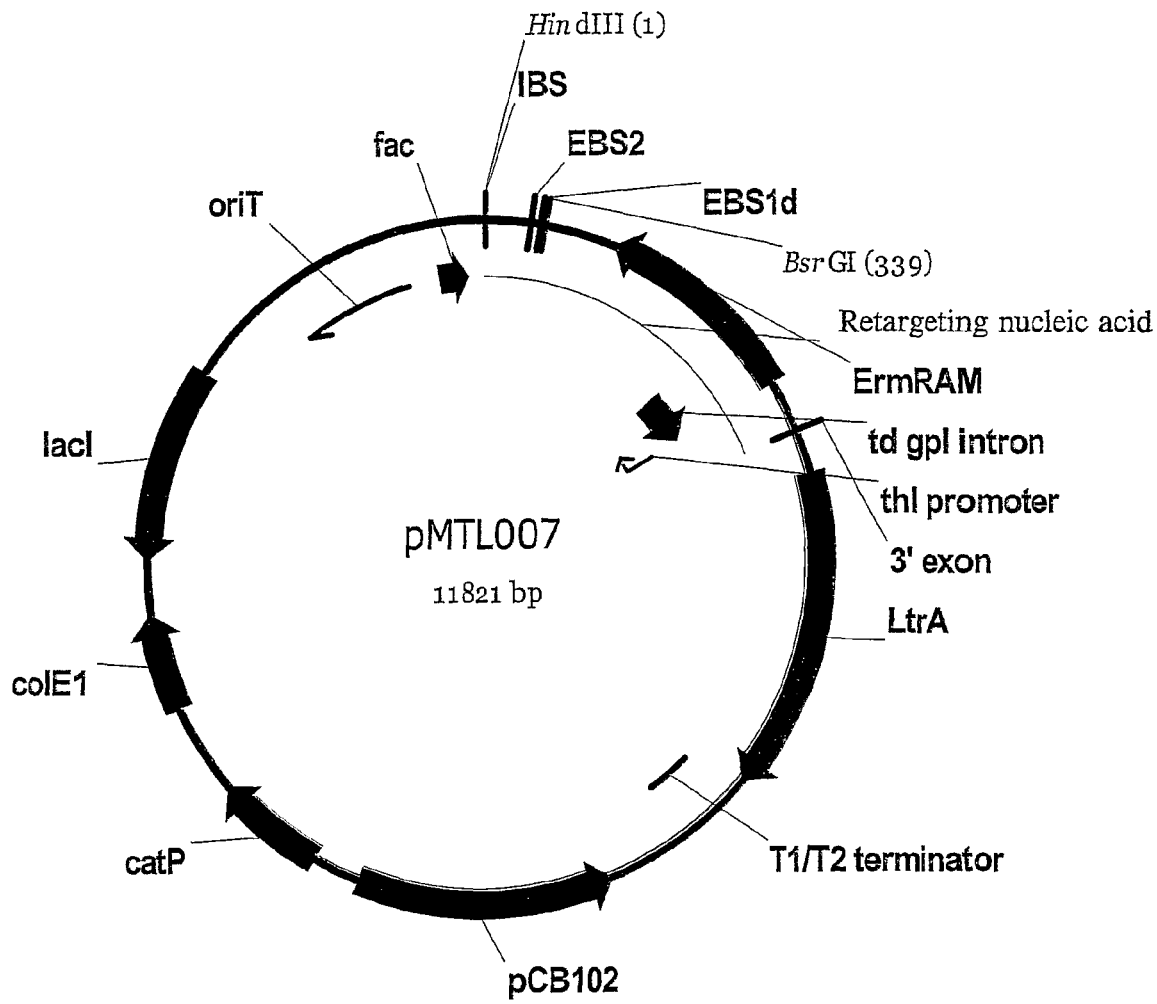

FIG. 11. Features and sequence of pMTL007

Plasmid map of the final clostridial retargeting system (the illustrated example is a derivative modified to re-target lacZ) and sequence (SEQ ID No. 22)

Figure 12:
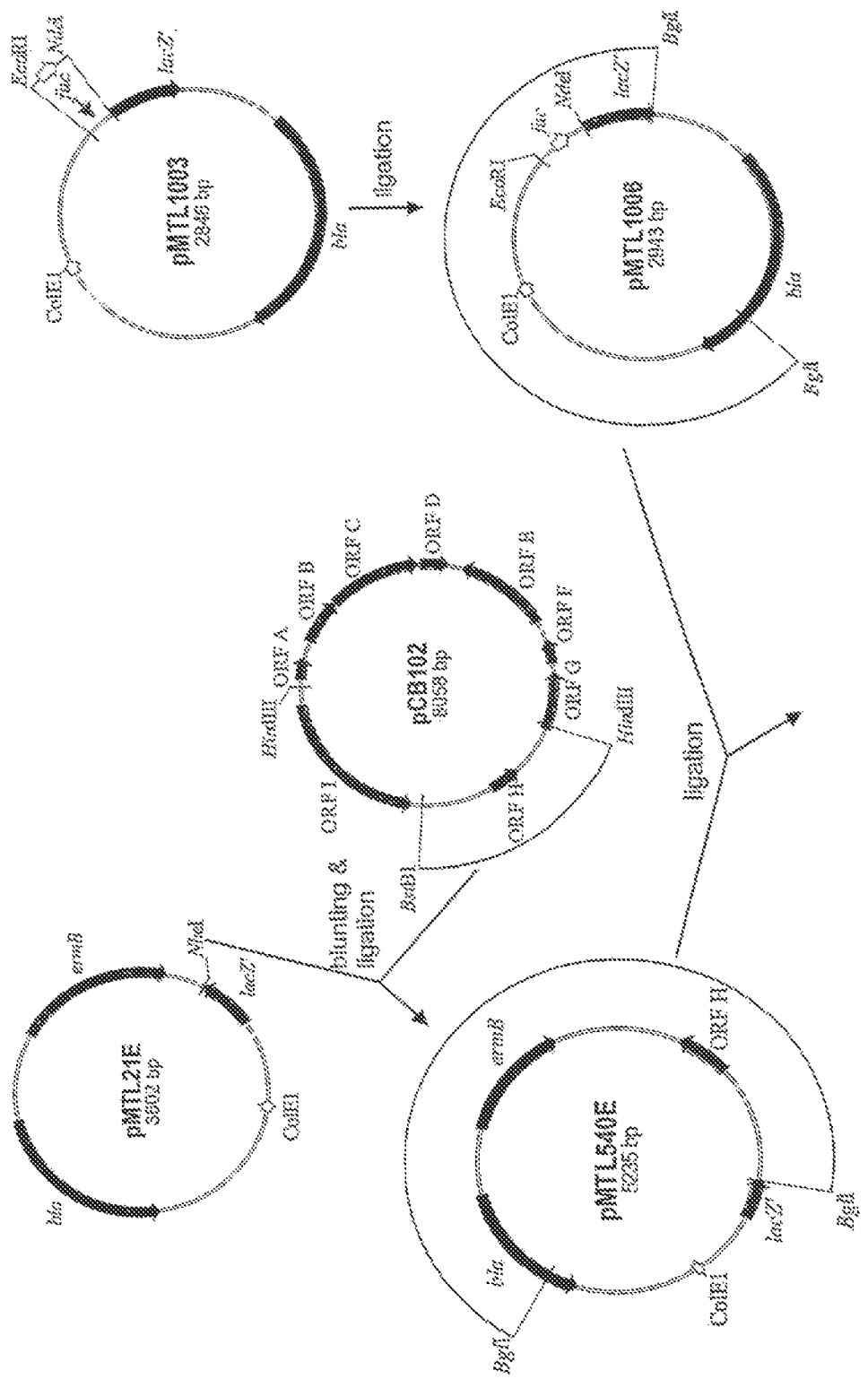

FIG. 12. Construction of pMTL5401F

Restriction sites used at each step are indicated. DNA end-blunting was performed using T4 DNA polymerase.

Figure 13:
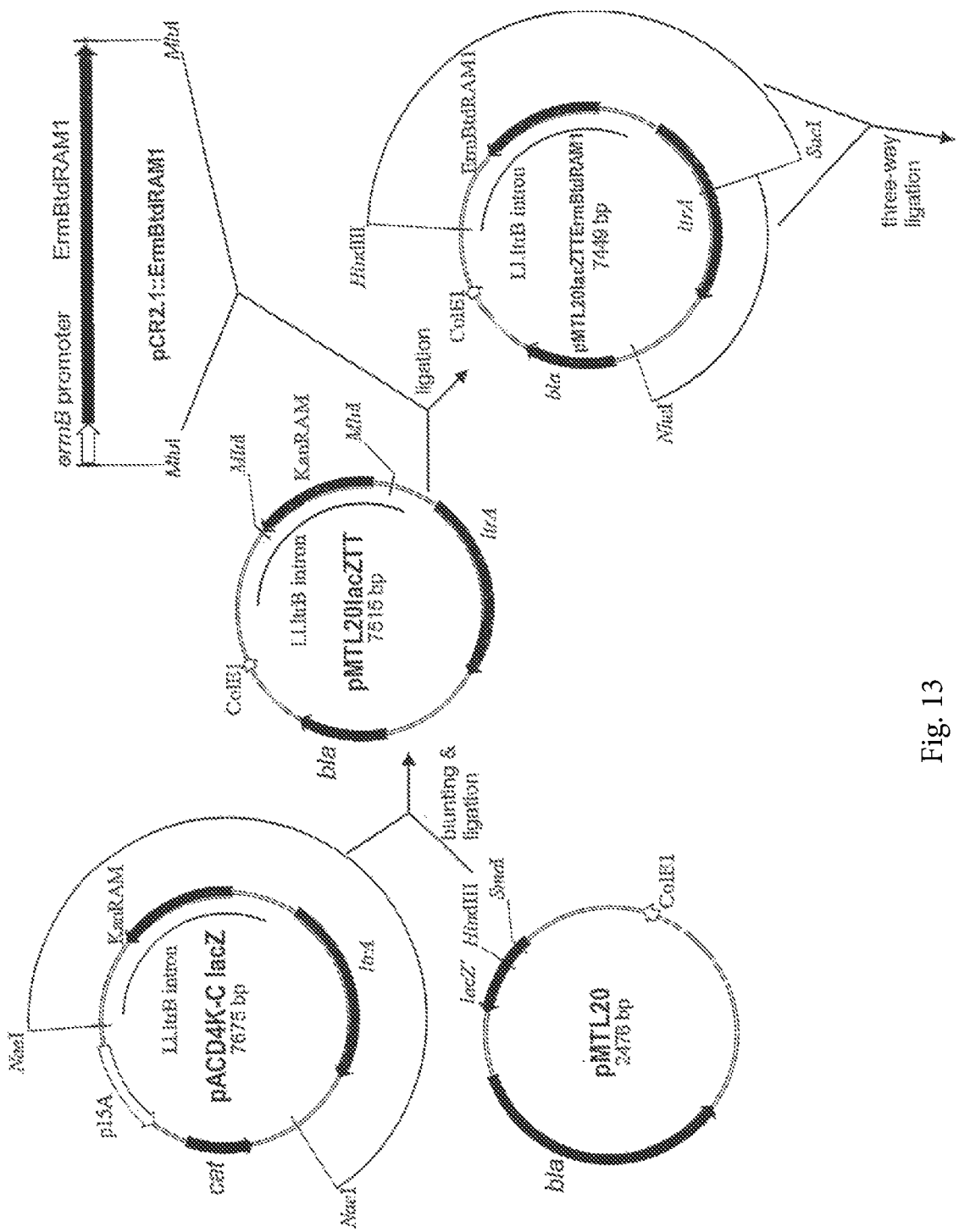
Figure 13:
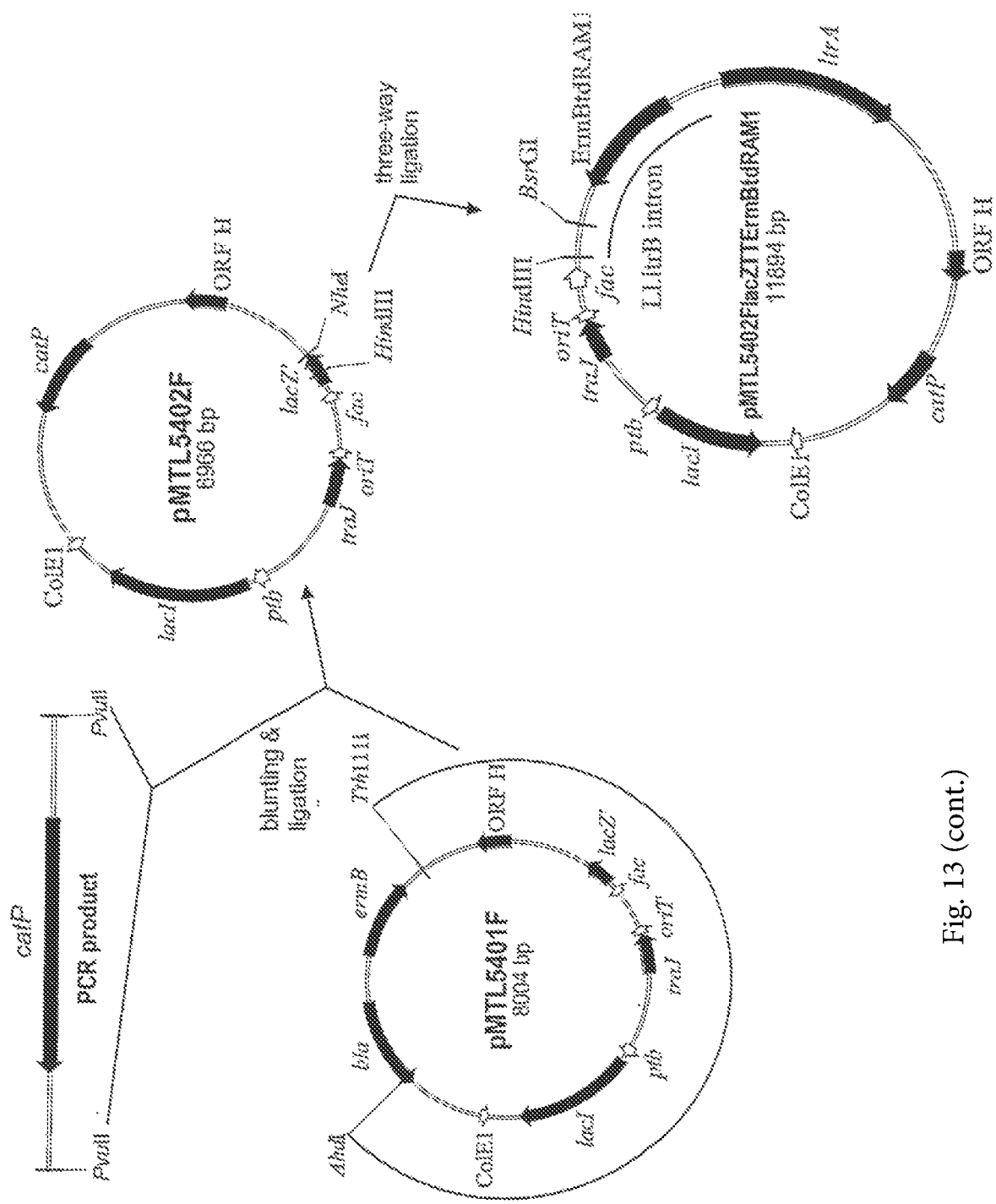

FIG. 13. Construction of pMTL5402F and pMTL5402F-lacZTTErmBtdRAM1

Restriction sites used at each step are indicated. DNA end-blunting was performed using T4 DNA polymerase.

Figure 14:
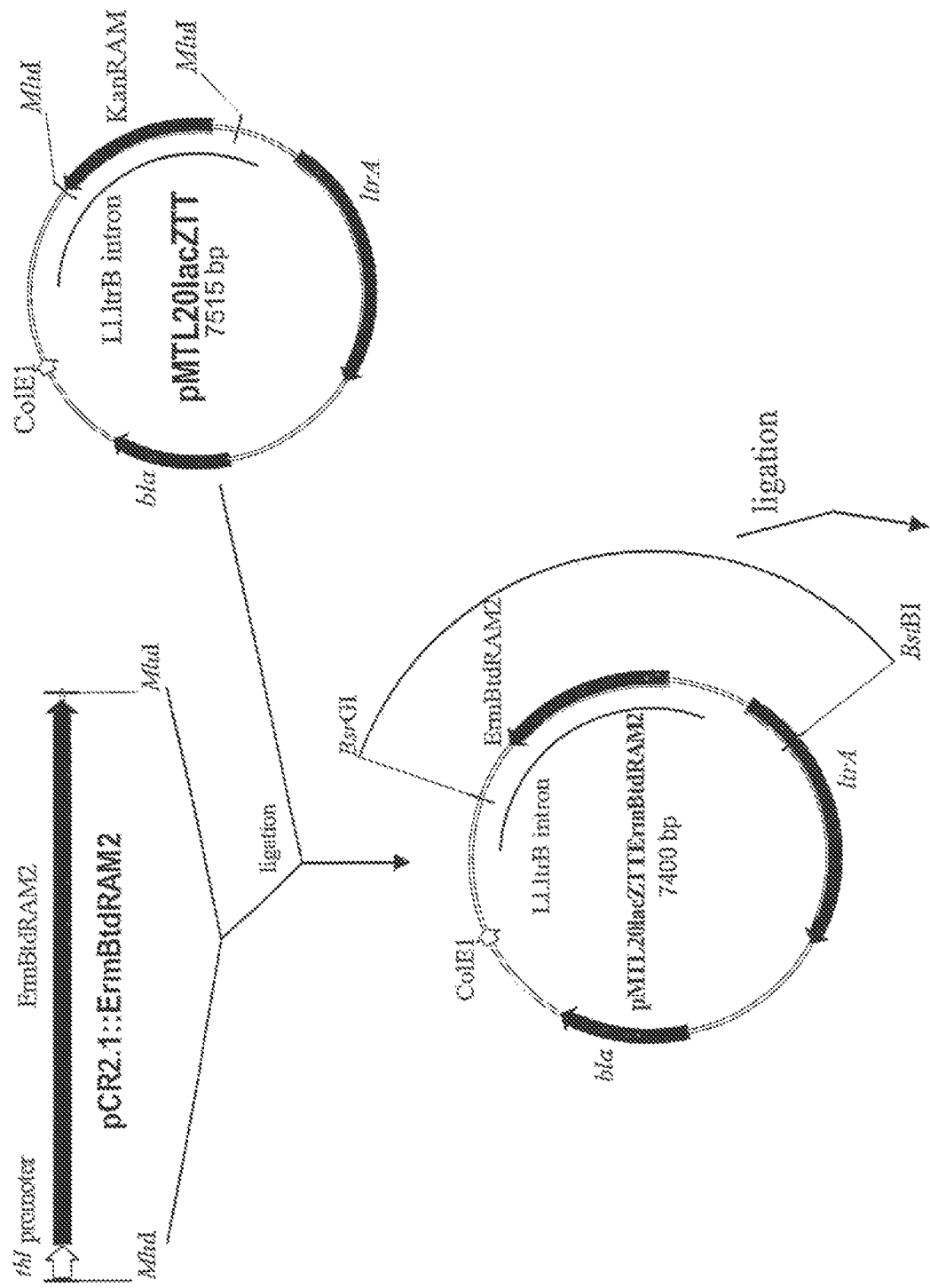

FIG. 14. Construction of pMTL007

Restriction sites used at each step are indicated.

FIGS. 15A, 15B, 15C, 15D, 15E, and 15F. Examples of mutant screening and characterisation.

FIG. 15A Plasmid pMTL007. FIGS. 15B and 15C PCR was used to initially screen for the presence of the intron insertion in the C. difficile spo0A gene using the intron-specific primer EBS Universal and gene-specific primer Cd-spo0A-R2 (small arrows). Lane 1: water; Lane 2: C. difficile parental strain genomic DNA; Lane 3: pMTL007::Cdi-spo0A-178a plasmid DNA; Lanes 4-6: DNA from three randomly-selected Em$^R$ C. difficile clones generated using pMTL007::Cdi-spo0A-178a. FIG. 15D Southern blots of the spo0A and pyrF mutants of C. difficile using a probe to ermB. Hybridisation of this probe to the pre-existing (non-functional) chromosomal ermB ORF causes a second band, also visible in the parental lanes. In the EcoRV digest of the spo0A mutant, both bands are a similar size. FIG. 15E Equivalent Southern blot for C. acetobutylicum and FIG. 15F C. sporogenes.

Figure 16:
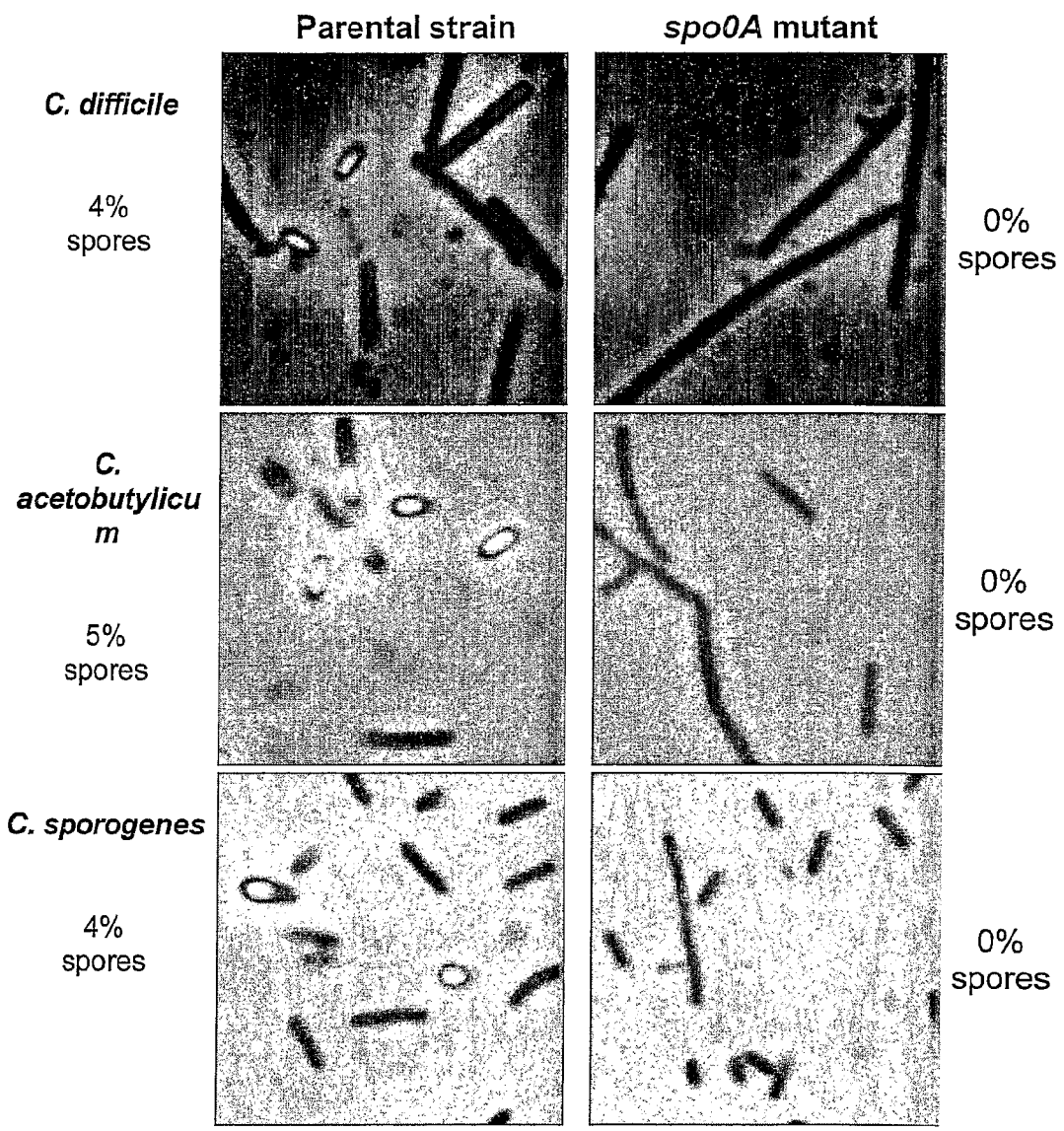

FIG. 16. The spo0A mutants do not form spores.

Phase-contrast micrographs of the spo0A mutants and parental strains of C. difficile, C. acetobutylicum and C. sporogenes grown on solid media for 14 days, 4 days or 3 days respectively. Mean sporulation frequencies of three separate experiments are shown as percentages.

EXAMPLE 1

Development of an IPTG-inducible 'fac' Promoter

The use of a E. coli/Clostridium shuttle vector (pMTL540F) carrying the artificial promoter 'fac' has previously been described. It was derived by inserting the operator of the E. coli lacZ operon immediately downstream of the promoter of the C. pastueurianum ferredoxin gene (Fox et al (1996) Gene Ther. 3: 173-178). Although this promoter element was used to direct the high level expression of heterologous genes in clostridia, regulated transcription has not been demonstrated. A new E. coli/Clostridium shuttle vector pMTL5401F was, therefore, constructed featuring the fac promoter, a lacI repressor gene under the transcriptional control of the promoter of the C. acetobutylicum phosphotransbutyrylase (ptb) gene and the oriT region of plasmid RK2 to facilitate conjugative transfer to C. sporogenes, C. botulinum and C. difficile. To test pMTL5401F, we inserted a promoterless copy of the pC194 cat gene, such that its transcription was under the control of the fac promoter in the resultant plasmid, pMTL5401Fcat (FIG. 3). We then assayed for the enzyme activity of the cat gene product in the lysates of C. sporogenes or C. acetobutylicum cells carrying pMTL5401Fcat, grown in the presence or absence of exogenous IPTG. Induction was observed in both organisms, but while strong repression of transcription was evident in C. sporogenes in the absence of IPTG (FIG. 3), a significant basal level of expression was observed in C. acetobutylicum (FIG. 3). Although pMTL5401F could be introduced into C. difficile, the pCB102 replicon functions relatively ineffectively in this clostridial host (Purdy et al (2002) Mol. Microbiol. 46: 439-452) and cannot support the growth of its transconjugants in antibiotic-supplemented liquid culture. Therefore, an equivalent induction experiment could not be performed.

EXAMPLE 2

Development of ErmBtd as a Selectable Marker for Clostridia

Splicing of the td group I intron is reliant on exon sequences flanking the point of insertion. The target site recognised by the Phage T4 td group I intron is 5'-GACCCAAGAA-3' (SEQ ID No. 23) and the intron inserts after the initial 'G'. However the td group I intron will also insert at the site 5'-GACCCAAGAGA-3' (SEQ ID No. 5) (Sigma Aldrich TargeTron™ Gene Knockout System). Sequences of antibiotic genes currently in use in Clostridia were evaluated for the presence of these sequences but no genes incorporating either of these sequences were identified. If the splice site 5'-GACCCAAGAGA-3' (SEQ ID No. 5) were present in a protein coding region, the amino acid sequence it would encode would depend on its reading frame. Amino acid sequences (corresponding to the three possible frames) that may be encoded by the splice site are shown in FIG. 4. Screening of the protein sequences of all proteins known to confer resistance on clostridia failed to identify a candidate protein containing any of the desired amino acid sequences.

Accordingly, a gene encoding a selectable marker was engineered such that it contained an insertion site for the td group I intron. This was to form the basis of a Clostridial RAM. The native ermB gene of the Enterococcus faecalis plasmid pAMB1, which confers resistance to erythromycin, was chosen as the selectable marker gene because this gene has been widely used in the construction of E. coli/Clostridium shuttle vectors (Dürre, P. Handbook on Clostridia. 2005. Taylor and Francis, CRC Press.)

A linker sequence was designed which contained the required splice site, and fused to the 5' end of the coding region of the ermB gene, in effect extending the N-terminus of the protein by 12 amino acids (FIG. 5). In the design of this sequence, the chosen reading frame was that which encoded amino acids that were as inert as possible, and soluble, to minimise risk of adversely affecting ErmB protein function. Frame 1 (DPRD; SEQ ID No. 6) was the best option as it includes three charged residues (Asp −ve, Arg +ve) which should favour solubility. It was hoped that the mixture of charges might help prevent a strong interaction with the rest of the protein. The rest of the linker was composed of the small, inert residues Gly and Ala, with a single Ser to avoid a long stretch of hydrophobic residues which might reduce the protein's solubility. In addition, the nucleotide sequence chosen incorporates clostridial codon usage, to minimise any potential expression problems.

Two constructs were assembled using SOEing PCR as described below, using oligonucleotide primers indicated in Table 1 below. The ErmBtd RAM1 (the modified ermB gene containing the td intron inserted at the indicated site in FIG. 6 (SEQ ID No. 13), and the spliced equivalent (SE), in which the td intron is absent. ErmBtdRAM1 and ErmBtdRAM1 SE were each cloned into the high copy plasmid pMTL5402F in the opposite orientation to the fac promoter (so that any resistance conferred is due to the RAM or SE's own promoter).

TABLE 1

Oligonucleotide primers

| Primer | Sequence (5'-3') | SEQ ID NO |
| --- | --- | --- |
| ErmB-Pro-F3 | CTACGCGTGGAAATAAGACTTAGAAGCAAA CTTAAGAGTGTG | 24 |
| ErmB-Pro-RA | CAGAAGCACCAGCATCTCTTGGGTCCATGT AATCACTCCTTCTTAATTACAAATTTTTAG CATC | 25 |
| linker1-ErmB-F1 | ACCCAAGAGATGCTGGTGCTTCTGGTGCTG GTATGAACAAAAATATAAAATATTCTCAAA ACTTTTTAACGAGTG | 26 |
| ErmB-R1 | GAACGCGTGCGACTCATAGAATTATTTCCT CCCG | 27 |
| ErmB-Pro-RB | GGGGTAAGATTAACGACCTTATCTGAACAT AATGCCATGTAATCACTCCTTCTTAATTAC AAATTTTTAGCATC | 28 |
| tdGpI-F1 | GCATTATGTTCAGATAAGGTCGTTAATCTT ACCCC | 29 |
| tdGpI-R1 | CCAGAAGCACCAGCATCTCTTGGGTTAATT GAGGCCTGAGTATAAG | 30 |
| Thio-F1 | CTACTAGTACGCGTTATATTGATAAAAATA ATAATAGTGGG | 31 |
| Thio-R-RAM | CCTTATCTGAACATAATGCCATATGAATCC CTCCTAATTTATACGTTTTCTC | 32 |

The ErmBtdRAM1 SE was made as follows. The ErmB promoter was PCR-amplified from pMTL5402F using primers ErmB-Pro-F3 and ErmB-Pro-RA. The ermB ORF was PCR-amplified from pMTL5402F using primers linker1-ErmB-F1 and ErmB-R1. The PCR products were gel-purified and used as templates in a SOEing PCR using the outer primers ErmB-Pro-F3 and ErmB-R1. The PCR product encoding ErmBtdRAM1 SE was cloned into pCR2.1-TOPO. ErmBtdRAM1 SE was excised from pCR2.1::ErmBtdRAM1SE as a HindIII/XhoI fragment and ligated into pMTL5402F linearised with the same enzymes. This placed ErmBtdRAM1 SE in the opposite orientation to the fac promoter on the resulting plasmid pMTL5402F::ErmBtdRAM1SE.

The ErmBtdRAM1 construct was made as follows. The ermB promoter was PCR-amplified from pMTL5402F using primers ErmB-Pro-F3 and ErmB-Pro-RB. The ermB ORF was PCR-amplified from pMTL5402F using primers linker1-ErmB-F1 and ErmB-R1. The attenuated td group I intron and its exons were PCR-amplified from pACD4K-C using primers tdGpI-F1 and tdGpI-R1. The PCR products were gel-purified and used as templates in a 3-way SOEing PCR using the outer primers ErmB-Pro-F3 and ErmB-R1. The PCR product encoding ErmBtdRAM1 was cloned into pCR2.1-TOPO. ErmBtdRAM1 was excised from pCR2.1::ErmBtdRAM1 as a HindIII/XhoI fragment and ligated into pMTL5402F linearised with the same enzymes.

*E. coli* carrying pMTL5402F::ErmBtdRAM1 was sensitive to erythromycin at 500 and 125 µg/ml (no growth overnight at 37° C.). *E. coli* carrying pMTL5402F::ErmBtdRAM1SE was resistant to erythromycin at 500 and 125 µg/ml (grew overnight at 37° C.). These experiments demonstrated that the modified ermB gene conferred resistance to erythromycin in *E. coli*, and equally important, that the insertion of td inactivates the gene.

EXAMPLE 3

Validation of the ErmBtd Selectable Marker in *E. Coli*

The retargeting nucleic acid component of pACD4K-C was sub-cloned as a NaeI (blunt) fragment into pMTL20 (Chambers et al (1988) *Gene* 68: 139-149) between HindIII and SmaI sites and the lacZ re-targeting region again shown to be able to knock-out the lacZ gene in the *E. coli* host HMS 174(DE3). Next the KanRAM in pMTL20lacZTT was replaced with ErmBtd RAM1 as MluI fragment. To test that the td group I intron was being spliced from ErmBtd RAM1 following induction of group II intron RNA expression, *E. coli* cells carrying pMTL20lacZTTErmBtdRAM1 were harvested and RNA prepared. RT-PCR reactions were then undertaken using primers that flank the td site of insertion. As a control, standard PCR was performed on ErmBtd RAM1 and ErmBtd RAM1 SE (the spliced equivalent of ErmBtd RAM1). As can be seen in FIG. 7, the predominant product obtained from the IPTG induced RNA samples was of the smaller size corresponding to the SE gene. This clearly demonstrates that td is being spliced from the RNA of the modified ermB gene in ErmBtd RAM1.

Despite the fact that demonstrable splicing of ErmBtd RAM1 had been shown to occur, no erythromycin resistant colonies were obtained following plating of the IPTG induced cells on agar media supplemented with 500, 250 or 125 µg/ml erythromycin. It was not possible to reduce the concentration of antibiotic any further, as *E. coli* is naturally resistant to lower levels of the antibiotic.

Failure to obtain erythromycin resistant colonies may have been due to a copy number effect. Thus, a single copy inserted in the genome may have been insufficient to raise resistance to the antibiotic above the usual low level of resistance inherent to wild type *E. coli*. To test this possibility, a DNA fragment fragment carrying ErmBtdRAM1 SE was ligated to cleaved pACYC184, and the ligation mixture transformed into *E. coli* and plated on 2YT containing either tetracycline or erythromycin at three different concentrations, 500, 250 and 125 µg/ml. Similar numbers of colonies grew on Erm125 and Tet, but several-fold less grew on Erm250, and only a few grew on Erm500. This control experiment set the practical limit for the screening of the inheritance of ErmBtdRAM1 SE when present on pACYC184 as being 125 µg/ml.

Having established the level of erythromycin needed to screen for ErmBtdRAM1 SE in *E. coli*, a region of lacZ encompassing the targeting region was PCR amplified with primers lacZ target-F (ACGAATTCCGGATAATGC-GAACAGC-GCACGG; SEQ ID No. 33) and lacZ target-R (TGCGATCGCACCGCCGA-CGGCACGCTGATTG; SEQ ID No. 34), cloned into pCR2.1TOPO, and then subcloned into pACYC184, which is present at several copies in the *E. coli* cell. The re-targeting experiment was then repeated by introducing pMTL20lacZTTErmBtdRAM1 into *E. coli* cells carrying pACYC184::lacZ. Following induction with IPTG, the cells were plated onto media containing erythromycin. In contrast to the previous experiment, appreciable numbers of resistant colonies were obtained. The use of appropriate primers in a diagnostic PCR confirmed that re-targeting of the group II intron to the lacZ gene on pACYC184 had taken place. Therefore, when ErmBtdRAM1 SE is present as a single copy, expression of ErmB is insufficient to confer resistance to erythromycin, but when present in multiple copies, ErmB is expressed at a sufficient amount to confer the resistant phenotype.

EXAMPLE 4

Construction of a Clostridial Retargeting System Using the ErmBtd Selectable Marker Having established that ErmBtdRAM1 could substitute for the KanRAM in the Sigma-Aldrich group II intron, the entire element, together with the re-targeting region for lacZ, was subcloned from pMTL20lacZTTErmBtdRAM1 (as HindIII/SacI and SacI/NheI fragments) into the clostridial expression vector pMTL5402F (cleaved with HindIII-NheI) to give pMTL5402FlacZTTErmBtdRAM1. As a consequence, expression of the group II intron was under the control of the fac promoter. Expression of the group II intron will be regulated by IPTG.

The ability of this vector to re-target the lacZ gene on pACYC184::lacZ in *E. coli* was tested. Following IPTG induction and plating on erythromycin, successful re-targeting was demonstrated.

EXAMPLE 5

Determination of the Efficiency of ErmBtdRAM1 in Group II Intron Retargeting

To assess whether ErmBtdRAM1 affects the frequency with which the group II intron can retarget, compared to KanRAM, we undertook some mobility assays using a two-plasmid system developed Karberg et al (2001, supra). Retargeting of the group II intron from pACD2, following IPTG-induction, to pBRR3-LtrB (which carries its natural target, LtrB) results in activation of the Tet gene on the latter plasmid. Thus, individual retargeting events can be detected on the basis of acquisition of resistance to Tetracycline.

Plasmid pACD2 was therefore modified by the insertion of either the ErmBtdRAM1 or the KanRAM, into the vector's unique MluI site. These two plasmids were then transformed into HMS174(DE3) cells containing pBRR3-LtrB—i.e. the recipient plasmid with the wild type target sequence. After selection for the donor plasmid, cells were induced with 500 μM IPTG for 1 hr, re-suspended in LB, allowed to recover for 1 hr, and then various dilutions were plated onto various selective plates. For those constructs containing a RAM, $Tet^R$ colonies were first re-streaked onto Tet plates and then again onto plates containing the appropriate antibiotic to test RAM splicing. Results are shown in Table 2.

This experiment demonstrated that the KanRAM and ErmBtdRAM1 have a similar effect on intron efficiency—presumably mainly due to the increased size of the intron. Importantly, the data indicate that both RAMs splice at similar efficiencies.

TABLE 2

Results of mobility assays

| Donor plasmid | Intron mobility efficiency* | RAM splicing efficiency† |
|---|---|---|
| pACD2 (none | ~10⁰ | n/a |
| pACD2::KanRAM) | ~10⁻³ | 18/20 |
| pACD2::ErmBtdRAM | ~10⁻³ | 18/20 |

*Intron mobility efficiency = $Tet^R$ colonies/$Amp^R$ $Cm^R$ colonies
†RAM splicing efficiency = $Kan^R$ or $Erm^R$ re-streaked $Tet^R$ colonies/all re-streaked $Tet^R$ colonies Splicing of neither RAM could be detected by antibiotic resistance initially, but only when re-streaked from $Tet^R$ colonies.

EXAMPLE 6

Identification of Effective Clostridial Re-targeting Sequences

To evaluate retargeting of the ErmBtdRAM1, eight different test genes were chosen from 3 different clostridial species. These were: *Clostridium sporogenes* pyrF, spo0A, codY, and SONO, *Clostridium difficile* pyrF (Genome Annotation No. CD3592) and spo0A (Genome Annotation No. CD1214), *Clostridium aceotbutylicum* pyrF (Genome Annotation No. CAC2652) and spo0A.

Each gene was analysed at http://www.sigma-genosys-.com/targetron/, and suitable changes to allow for re-targeting identified. Using appropriate primers, the generation of appropriately modified Group II introns was effected by performing a PCR as directed in the Sigma-Aldrich TargeTron™ Gene Knockout System User Guide. Each PCR required unique IBS, EBS2 and EBS1d primers designed to modify the targeting portions of the Group II intron or its 5' exon, and the EBS Universal primer. The sequences of the target insertion sites for each gene and primers are given in Tables 3 and 4 below.

TABLE 3

Predicted target insertion sites for retargeting nucleic acids

| Target*a* | Target insertion site sequence 5'-3' | SEQ ID No |
|---|---|---|
| *C. sporogenes* codY 417s | GCTAGATTTGATAAAGAATTTACTGAT GAA-intron-GATTTAGTGTTAGCA | 35 |
| *C. difficile* pyrF 97a | CAACGTATTGCTCTAGCCCTACCTTAA ATA-intron-TGTCTACACTATCTT | 36 |
| *C. difficile* spo0A 178a | ATCCATCTAGATGTGGCATTATTACAT CTA-intron-GTATTAATAAGTCCG | 37 |
| *C. sporogenes* spo0A 249s | AATAGTATAGATATTACTCCTATGCCA AGG-intron-GTAATTGTTTTGTCT | 38 |

TABLE 3-continued

Predicted target insertion sites for retargeting nucleic acids

| Target[a] | Target insertion site sequence 5'-3' | SEQ ID No |
|---|---|---|
| C. sporogenes pyrF 595s | GTAATTGTGGATATAGCTCTATAGGAG CAG-intron-TAGTTGGATGTACAG | 39 |
| C. acetobutylicum pyrF 345s | GAAATGTATGCTAAAGCTCACTTTGAA GGT-intron-GATTTTGAAGCGGAT | 40 |
| C. acetobutylicum spo0A 242a | CCAACAGCGGATAAAACTATTATTCTT GGA-intron-AGGTTTTCTGCATCT | 41 |
| C. sporogenes SONO 492s | ATCAAAGTAGATGAAATAGAAAGAAAA GAT-intron-GATTTTTAAAACTT | 42 |

[a]Target indicated as organism, ORF and insertion point. Target insertion sites were selected such that introns would be inserted after the indicated number of bases from the start of the ORF, in either the sense (s) or antisense (a) orientation.

TABLE 4

Oligonucleotide primers used to generate PCR products for retargeting

| Primer | Primer sequence 5'-3' | SEQ ID No. |
|---|---|---|
| EBS Universal | CGAAATTAGAAACTTGCGTTC AGTAAAC | 43 |
| Csp-codY-417s-IBS | AAAAAAGCTTATAATTATCCT TATTTACCGATGAAGTGCGCC CAGATAGGGTG | 44 |
| Csp-codY-417s-EBS1d | CAGATTGTACAAATGTGGTGA TAACAGATAAGTCGATGAAGA TAACTTACCTTTCTTTGT | 45 |
| Csp-codY-417s-EBS2 | TGAACGCAAGTTTCTAATTTC GGTTGTAAATCGATAGAGGAA AGTGTCT | 46 |
| Cdi-pyrF-97a-IBS | AAAAAAGCTTATAATTATCCT TACTACCCTAAATAGTGCGCC CAGATAGGGTG | 47 |
| Cdi-pyrF-97a-EBS1d | CAGATTGTACAAATGTGGTGA TAACAGATAAGTCTAAATATG TAACTTACCTTTCTTTGT | 48 |
| Cdi-pyrF-97a-EBS2 | TGAACGCAAGTTTCTAATTTC GGTTGGTAGTCGATAGAGGAA AGTGTCT | 49 |
| Cdi-spo0A-178a-IBS | AAAAAAGCTTATAATTATCCT TATTATTCCATCTAGTGCGCC CAGATAGGGTG | 50 |
| Cdi-spo0A-178a-EBS1d | CAGATTGTACAAATGTGGTGA TAACAGATAAGTCCATCTAGT TAACTTACCTTTCTTTGT | 51 |
| Cdi-spo0A-178a-EBS2 | TGAACGCAAGTTTCTAATTTC GGTTAATAATCGATAGAGGAA AGTGTCT | 52 |
| Csp-spo0A-249s-IBS | AAAAAAGCTTATAATTATCCT TACCTATCCCAAGGGTGCGCC CAGATAGGGTG | 53 |
| Csp-spo0A-249s-EBS1d | CAGATTGTACAAATGTGGTGA TAACAGATAAGTCCCAAGGGT TAACTTACCTTTCTTTGT | 54 |
| Csp-spo0A-249s-EBS2 | TGAACGCAAGTTTCTAATTTC GGTTATAGGTCGATAGAGGAA AGTGTCT | 55 |
| Csp-pyrF-595s-IBS | AAAAAAGCTTATAATTATCCT TACTATACGAGCAGGTGCGCC CAGATAGGGTG | 56 |
| Csp-pyrF-595s-EBS1d | CAGATTGTACAAATGTGGTGA TAACAGATAAGTCGAGCAGTA TAACTTACCTTTCTTTGT | 57 |
| Csp-pyrF-595s-EBS2 | TGAACGCAAGTTTCTAATTTC GGTTTATAGTCGATAGAGGAA AGTGTCT | 58 |
| Cac-pyrF-345s-IBS | AAAAAAGCTTATAATTATCCT TACACTTCGAAGGTGTGCGCC CAGATAGGGTG | 59 |
| Cac-pyrF-345s-EBS1d | CAGATTGTACAAATGTGGTGA TAACAGATAAGTCGAAGGTGA TAACTTACCTTTCTTTG | 60 |
| Cac-pyrF-345s-EBS2 | TGAACGCAAGTTTCTAATTTC GGTTAAGTGTCGATAGAGGAA AGTGTCT | 61 |
| Cac-spo0A-242a-IBS | AAAAAAGCTTATAATTATCCT TAATTATCCTTGGAGTGCGCC CAGATAGGGTG | 62 |
| Cac-spo0A-242a-EBS1d | CAGATTGTACAAATGTGGTGA TAACAGATAAGTCCTTGGAAG TAACTTACCTTTCTTTGT | 63 |
| Cac-spo0A-242a-EBS2 | TGAACGCAAGTTTCTAATTTC GGTTATAATCCGATAGAGGAA AGTGTCT | 64 |
| Csp-SONO-492s-IBS | AAAAAAGCTTATAATTATCCT TAGAAAGCAAAGATGTGCGCC CAGATAGGGTG | 65 |
| Csp-SONO-492s-EBS1d | CAGATTGTACAAATGTGGTGA TAACAGATAAGTCAAAGATGA TAACTTACCTTTCTTTGT | 66 |
| Csp-SONO-492s-EBS2 | TGAACGCAAGTTTCTAATTTC GATTCTTTCTCGATAGAGGAA AGTGTCT | 67 |

To ensure that the modified group II introns were capable of retargeting to the selected clostridial genes, experiments were first undertaken in E. coli using plasmid systems that were known to function effectively. The system utilised is a two-plasmid system developed by Karberg et al (2001) as described in Example 5. Using this system, the engineered group II intron is placed on one plasmid (pACD2) and its target (in this case the cloned clostridial gene) is placed on a second plasmid (pBRR3). Retargeting of the group II intron from pACD2 to pBRR3 results in activation of the Tet gene on the latter plasmid. Thus, individual retargeting events can be detected on the basis of acquisition of resistance to Tetracycline. A portion of the bacteria are plated on non-selective agar plates to give an indication of total viable bacteria and a portion are plated on tetracycline-containing agar plates (Tet plates). The efficiency of retargeting is estimated based on the proportion of total viable bacteria that are resistant to tetracycline.

To facilitate subcloning of the target genes from pCR2.1/ pCRII TOPO plasmids into pBRR3, a multiple cloning site was introduced into pBRR3-LtrB to make pBRR3-MCS1. This was done by insertion of a multicloning site fragment between the AatII and EcoRI sites of pBRR3-LtrB, containing restriction sites found in the pCR2.1-TOPO plasmid. Sequences of the cloning sites are given in FIG. 8. The multicloning site fragment depicted in FIG. 8 was made from MCS1a oligonucleotide CTCGAGGTACCATG-CATAGGCCTGAGCTCA-CTAGTGCGGCCGCG (SEQ ID No. 68) and MCS1b oligonucleotide AATTC-GCGGC-CGCACTAGTGAGCTCAGGCCTATGCATGGTACCTC-GAGACGT (SEQ ID No. 69).

Four retargeting nucleic acids (each intended for insertion in one of *C. sporogenes* genes pyrF, spo0A, codY, and SONO) were evaluated using the two-plasmid intron mobility assay. All four permitted far more efficient retargeting than anticipated. Consequently the dilutions chosen for plating on Tet plates were not ideal and were only just in range for colony counts and therefore the efficiencies given may be less accurate than if fewer bacteria had been plated. The next four retargeting nucleic acids (each intended for insertion in one of *C. difficile* pyrF and spo0A genes or *C. acetobutylicum* pyrF and spo0A genes) were evaluated for retargeting. Retargeting events were estimated by plating bacteria on Tet plates. In this initial experiment, SONO gave no $Em^R$ colonies. Results are shown in Table 5.

TABLE 5

Results of intron mobility assay

| Donor plasmid | Recipient plasmid | Intron mobility efficiency* |
|---|---|---|
| pACD2::Cs-spo0A-249s TR | pBRR3::Cs-spo0A AS2 frag | ~15% |
| pACD2::Cs-codY-417s TR | pBRR3::Cs-codY AS2 frag | ~20% |
| pACD2::Cd-pyrF-97a TR | pBRR3::Cd-pyrF-97 target | ~100% |
| pACD2::Cd-spo0A-178a TR | pBRR3::Cd-spo0A-178 target | ~20% |
| pACD2::Cs-pyrF-595s TR | pBRR3::Cs-pyrF | ~2% |
| pACD2::Ca-pyrF-345s TR | pBRR3::Ca-pyrF | ~0.2% |
| pACD2::Ca-spo0A-242a TR | pBRR3::Cs-spo0A | ~20% |
| pACD2::Cs-SONO-492s TR | pBRR3::Cs-SONO" | ND |

*Intron mobility efficiency = $Tet^R$ colonies/$Amp^R$ $Cm^R$ colonies, Cs – *C. sporogenes*, Ca – *C. acetobutylicum*, Cd – *C. difficile*. Numbers refer to the site of intron insertion relative to the start of the gene, in either the sense (s) or antisense (a) orientation. TR = retargeting nucleic acid

EXAMPLE 7

Evaluation of Retargeting Nucleic Acids in Clostridia

The first four new retargeting nucleic acids (each intended for insertion in one of *C. sporogenes* genes pyrF, spo0A, codY, and SONO) were sub-cloned into the prototype vector pMTL5402FTTErmBtdRAM1, and the resultant recombinant plasmids introduced into the *E. coli* donor CA434, and thence used in conjugation experiments with either *C. sporogenes* or *C. difficile* as the recipient. In the case of the latter, no transconjugants were obtained. Transconjugants were obtained with both plasmids in the case of *C. sporogenes*. Single transconjugants were inoculated into 1.5 ml of an appropriate growth medium supplemented with 250 µg/ml cycloserine and 7.5 µg/ml thiamphenicol (the latter of which ensures plasmid maintenance) and the culture was allowed to grow to stationary phase by anaerobic incubation at 37° C. overnight. 150 µl of this culture was used to inoculate 1.5 ml of fresh broth of the same type and containing the same supplements, which was then incubated anaerobically at 37° C. As soon as growth was visible in the culture, typically after 1 hr, the culture was induced with IPTG and incubated for 1 hr.

2 ml of the induced cells were harvested by centrifugation for 1 minute at 7000 rpm, washed by re-suspension in PBS and harvested as before. The pellet was re-suspended in an equal volume (2 ml) of an appropriate growth medium without supplements, and incubated anaerobically at 37° C. for 1 hour. Serial dilutions of the culture were then plated onto an appropriate solid growth media supplemented with 1-10 µg/ml erythromycin, after 1 hr, 24 and 48 hr and incubated anaerobically at 37° C.

No erythromycin colonies were obtained after two independent attempts.

EXAMPLE 8

Evidence that the Natural ermB Promoter is too Weak to Drive Expression of ErmB Sufficient for it to Act as a Selectable Marker One explanation for the inability to detect retargeting of the retargeting nucleic acids as described in Example 7 is that the ermB promoter is too weak to allow a single copy of the gene in a cell's chromosome to confer resistance to erythromycin. Analysis of the ermB promoter sequence of *Enterococcus faecalis* plasmid pAMβ1 showed that the spacing between the promoter's –35 and –10 regions is 21 bp. The optimum for Gram-positive promoters is 17±1 bp.

The ErmBtdRAM1 SE was cloned in two different orientations in pMT5402F relative to fac. Only when the gene was under the control of fac was the plasmid carrying ErmBtdRAM1 SE capable of endowing the *C. sporogenes* host with resistance to erythromycin. In the opposite orientation, transcription of the ermB coding region is reliant on its own promoter and expression was insufficient for resistance, despite ermB being present on a multi-copy plasmid.

EXAMPLE 9

Development of a Clostridial ErmBtdRAM with a Strong Promoter

The promoter of the thl gene of *C. acetobutylicum* is recognised as a strong and constitutive promoter. Primers were designed to replace the ErmBtdRAM1 promoter with the thl promoter. These delete unnecessary sequences between the transcriptional start site and ribosome binding site, and insert an NdeI site at the start codon to allow the promoter to be easily changed again if necessary. To guard against the possibility that the thl promoter might be too strong, a mutant thl promoter 'thl2' was also designed, by changing the spacing between the −35 and −10 to 16 nt, and making minor changes to the −35 and −10 elements. Sequences of the thl and thl2 promoters spanning the −35 and −10 elements compared to a consensus Gram positive vegetative promoter are shown in FIG. 9. The sequence of the complete thl promoter is given at positions 15-84 of the ErmBtdRAM2 sequence in FIG. 10. The sequence of the complete thl2 promoter differs from the thl promoter only in the region depicted in FIG. 9.

The thl and thl2 promoters were fused to the ErmBtdRAM1 and ErmBtdRAM1 SE start codons using SOEing PCR and cloning steps, producing ErmBtdRAM2 and ErmBtdRAM2 SE, each containing the thl promoter, and ErmBtdRAM3 and ErmBtdRAM3 SE each containing the thl2 promoter. Sequence-correct clones were obtained of both RAM2 and RAM3, and were sub-cloned into pACD2 and pMTL20lacZTT for evaluation. The features and sequence of ErmBtdRAM2 is depicted in FIG. 10.

The ability of the RAM2 and RAM3 portions to confer resistance to erythromycin on *E. coli* TOP10 cells was determined for plasmids containing these portions as indicated in Table 6 below.

TABLE 6

Erythromycin sensitivity of TOP10 clones bearing new constructs

| RAM | TOPO | SE TOPO | pACD2:: RAM | pMTL20-lacZTTRAM | pMTL5402F-TTRAM |
|---|---|---|---|---|---|
| ErmBtdRAM2 | R | R | S | S | S |
| ErmBtdRAM3 | S | R | S | S | S |

In all but the SE TOPO plasmid, the ermB gene is disrupted by the group I intron, and therefore resistance was not expected. In the SE TOPO plasmid, the ermB gene is not disrupted, and so if the promoter of ermB is sufficiently strong, a resistance phenotype should be obtained. Unexpectedly, RAM2 TOPO clone conferred resistance to erythromycin in *E. coli*. It would appear that the very strong thl promoter and very high copy number seems to overcome the presence of the group I intron in this context, presumably by rare translation initiation at the native ATG. This effect is only seen when the gene is present in TOPO. When inserted in a plasmid relevant for retargeting, such as pACD2 and pMTL20lacZTTRAM, *E. coli* cells are not resistant to erythromycin. The RAM3 resistance profile was as expected. Therefore, either promoter appeared to be useful to drive expression of the selectable marker in the Clostridial retargeting nucleic acid.

EXAMPLE 10

Evaluation of ErmBtdRAM2 and 3 in pACD2/pBRR3 System

The retargeting efficiency of the ErmBtdRAM2 and 3 were evaluated using the retargeting assay described in Example 5. Results are indicated in Table 7 below.

TABLE 7

Results of intron mobility assay

| Donor plasmid | Intron mobility efficiency* | RAM splicing efficiency† |
|---|---|---|
| Shown previously: | | |
| pACD2 | ~10⁰ | n/a |
| pACD2KanRAM | ~10⁻³ | 18/20 |
| pACD2ErmBtdRAM1 | ~10⁻³ | 18/20 |
| This experiment: | | |
| pACD2ErmBtdRAM2 | ~5 × 10⁻³ | 9/10 |
| pACD2ErmBtdRAM3 | ~7 × 10⁻² | 9/10 |

*Intron mobility efficiency = $Tet^R$ colonies/$Amp^R$ $Cm^R$ colonies
†RAM splicing efficiency = $Kan^R$ or $Erm^R$ re-streaked $Tet^R$ colonies/all re-streaked $Tet^R$ colonies Splicing of RAM2 and RAM3 was efficient (90%), and equivalent to the original RAM (RAM1).

EXAMPLE 11

Evaluation of ErmBtdRAM2 and 3 in pMTL20lacZTT System in *E. coli*

As previously, neither RAM could be used to detect retargeting of the Group II intron into lacZ in the *E. coli* HMS174(DE3) chromosome using either $Ery_{500}$ or $Ery_{125}$. RAM2 but not RAM3 gave numerous $Ery^R$ colonies, but they were shown by PCR not to contain a Group II intron retargeted to the lacZ gene. Presumably these colonies arose due to weak resistance conferred by the plasmid.

EXAMPLE 12

FIG. 11 illustrates the essential components of the vector pMTL007, also referred to as pMTL5402FlacZTTErmBtdRAM2. This Group II intron is modified to retarget the lacZ gene. It may be modified to retarget a gene of a bacterial cell of the class Clostridia.

The essential elements of the plasmid are:

A clostridial promoter to bring about expression of the retargeting nucleic acid element, which in the illustrated example is the inducible few promoter. Other promoters may be similarly employed which have been made inducible by provision of a lac operator, eg., fac2. To mediate induction the plasmid also carries the *E. coli* lacI gene under the control of a clostridial promoter, in this instance the promoter of the ptb gene (encoding phosphotransbutyrylase) of *Clostridium acetobutylicum*. A constitutive promoter may be used instead of an inducible promoter. The plasmid also carries the ColE1 replicon of plasmid pMTL20E, to allow maintenance of the plasmid in *E. coli* and the replication region of the *Clostridium butyricum* plasmid pCB 102, to allow maintenance in *Clostridium* species. Maintenance of the plasmid is also provided by the inclusion of the catP gene to enable selection of the plasmid in *E. coli* (through supplementation of the media with chloramphenicol) and Clostridia (through supplementation of the media with thiamphenicol). To provide the facility to conjugate the plasmid into clostridial recipients in addition to transformation, the vector also carries the oriT region of plasmid RP4.

All of these elements are interchangeable with other equivalent factors from other sources. Thus, ColE1 maybe exchanged with other replicons capable of replication in *E. coli*, such as p15a, pVW01 or phage origins such as M13. The catP gene may be substituted with other appropriate antibiotic resistance genes, such as tetM or aad. Similarly, any replicon capable of replicating in the targeted clostridial or Gram-positive bacterial host may be employed, such as pIM13, pIP404, pAMβ1, pCD6, pC194, pE194, pT181, pCB101, pBP1. Replicons which are defective for replication may also be employed, including replicons that may be conditional for replication, eg., temperature sensitive or reliant on an exogenous factor for replication. Plasmids may also be employed which lack any provision for replication in a Gram-positive plasmid, ie., a suicide vector carrying only a ColE1 replicon Other combinations of operator and repressor gene may be employed. A promoter identified on the conjugative transposon Tn5397 which is regulated by tetracycline (Tet), represents another candidate (Roberts, PhD thesis, UCL). Alternatively, a xylose-inducible promoter, derived from *S. xylosus*, has recently been shown to function in *C. acetobutylicum* (Girbal et al (2003) *Appl Environ Microbiol.* 69: 4985-8). Another candidate is a tet-regulated promoter developed in *B. subtilis* (Geissendorfer and Hillen (1990)

*Appl. Microbiol. Biotechnol.* 33: 657-63). It was constructed by adding a tet operator (tetO) sequence between the −35 and −10 of a strong xyl promoter (Geissendorfer and Hillen, 1990, supra). In the presence of a tetR gene (encoding the repressor), the derivatised promoter was 100-fold inducible by sub-lethal concentrations of Tet. The basal levels of expression obtained could be completely abolished by the addition of a second tet operator, although this addition caused an overall reduction in expression levels. Subsequently, this promoter has found wide application in *S. aureus* (Bateman et al (2001) *Infect Inzmun.* 69: 7851-7; Ji et al (2001) *Science* 293: 2266-2269), where only a single operator proved necessary.

A tet-regulated promoter makes an ideal alternative to our developed fac/lacI system. Thus, we will be able to express tetR using the same promoter used to express lacI (the *C. acetobutylicum* ptb promoter). In *B. subtilis*, the degree of induction was dose-dependent over the range tested. However, as *B. subtilis* was sensitive to the antibiotic, high concentrations of Tet could not be added. A similar constraint will not apply to clostridia such as *C. difficile*, winch are resistant to this antibiotic. To test the feasibility of the system, we will re-synthesise fac, replacing the region between the −35 and −10 with the tetO. Should high basal levels be observed in the absence of Tet, then a second operator can be added. Addition of further synthetic lacO sequences can also be used to enhance repression of promoters by LacI (Muller et al (1996) *J Mol Biol.* 257: 21-9).

Construction of pMTL007

Oligonucleotide primers used in the construction are indicated in Table 8 below.

TABLE 8

Oligonucleotide primers

| Primer | Sequence (5'-3') | SEQ ID No. |
|---|---|---|
| lacI-P1 | GTGGTGCATATGAAACCAGTAACG | 70 |
| lacI-P2 | GAATTCCTAACTCACATTAATTGCGTTGCG | 71 |
| ptb-P1 | GAATTCAGGGAATTAAAAGAATGTTTACCTG | 72 |
| ptb-P2 | ACTCATATGTTGCACCTCTACTTTAATAATTTTTAAC | 73 |
| tdGpI-F1 | GCATTATGTTCAGATAAGGTCGTTAATCTTACCCC | 29 |
| CatPFwd | CAGCTGACCGGTCTAAAGAGGTCCCTAGCGCC | 74 |
| CatPSOER | CGGTCATGCTGTAGGTACAAGGTAC | 75 |
| CatPRev | CAGCTGACCGGTCTCTGAAAATATAAAAACCACAGATTGATAC | 76 |
| CatPSOEF | GTACCTTGTACCTACAGCATGACCG | 77 |
| Thio-F1 | CTACTAGTACGCGTTATATTGATAAAAATAATAATAGTGGG | 78 |

TABLE 8-continued

Oligonucleotide primers

| Primer | Sequence (5'-3') | SEQ ID No. |
|---|---|---|
| Thio-R-RAM | CCTTATCTGAACATAATGCCATATGAATCCCTCCTAATTTATACGTTTTCTC | 79 |

A 1.627 kb LspI-HindIII fragment was isolated from the *Clostridium butyricum* plasmid pCB102 (Minton and Morris (1981) *J Gen Microbiol* 127: 325-33) and blunt- SmaI, and sub-cloned into the EcoRV restriction site of pMTL540F, generating pMTL5400F (see FIG. 12).

To bring about the production of LacI repressor protein, a promoter-less copy of the *E. coli* lacI gene was amplified from pNM52 (Gilbert et al (1986) *J. Gen. Microbiol.* 132: 151-160) as an approx 1.0 kb NdeI-EcoRI fragment using the PCR primers lacI-P1 and lacI-P2 In parallel, the promoter region of the *Clostridium acetobutylicum* ptb (phosphotransbutyrylase) gene was PCR amplified using the primers ptb-P1 and ptb-P2. This localised the gene to a 578 bp EcoRI-NdeI fragment. The two fragments were isolated and ligated with EcoRI-cleaved pMTL20E, thereby placing the lacI gene under the transcriptional control of the ptb promoter, and localizing the modified gene to a portable EcoRI fragment. This fragment was excised from the plasmid generated, blunt-ended with Klenow polymerase, and ligated with EcoRV-cleaved pMTL5400F. The plasmid obtained was designated pMTL5401F, as shown in FIG. 12.

Plasmid pMTL5401F carries an erm gene as the selectable marker. It is, therefore, not compatible with the ErmRAM. The erm gene was therefore replaced with the catP gene of pJIR418 (Sloan et al (1992) *Plasmid* 27: 207-219). This was achieved by cleaving pMTL5401F with AhdI/TthIII1, blunt-ending the DNA with Klenow polymerase, and then ligating to a 1.1 kb PvuII fragment carrying the pJIR418 catP gene to the larger of the two pMTL5401F fragments generated by cleavage with AhdI and TthIII1. This manipulation resulted in the complete deletion of ermB and removal of the majority of the bla gene. The plasmid obtained was designated pMTL5402F, as shown in FIG. 13.

Prior to this substitution, a BsrG1 site within the catP fragment was removed by mutating a sequence to destroy the BsrG1 palindrome without changing the catP coding sequence. This was undertaking using Sewing Overlap Extension (SOE) PCR (Horton et al., 1990), using the primers CatPSOEF and CatPSOER. In addition, the flanking primers CatPFwd and CatPRev used were designed to encompass both a PvuII site and internal AgeI sites. The former were incorporated for the subsequent insertion of the plasmid into pMTL5401F, whereas the latter were introduced to facilitate the subsequent substitution of catP in the final plasmid, pMTL007, with alternative markers at a future date.

pMLT007 was constructed as follows:

The Targetron™ plasmid pACD4K-C was purchased from Sigma, and re-targeted to the *E. coli* lacZ gene using the control primers provided in the kit according to the provided protocol, except that the PCR product was first cloned and its sequence verified before sub-cloning the HindIII/BsrGI fragment into pACD4K-C.

The lacZ-retargeting nucleic acid region was excised as a 5099 bp NaeI fragment and ligated into a 2412 bp fragment of pMTL20 which had previously been generated by digestion with HindIII and SmaI, with T4 polymerase blunting of the HindIII end, as shown in FIG. 13. A construct was chosen in the orientation in which the HindIII and NheI sites flanked the retargeting nucleic acid region.

The KanRAM was excised using MluI, and replaced with a 1259 bp MluI fragment containing ErmBtdRAM2, as shown in FIG. 13.

The entire lacZ-retargeting nucleic acid region including the ErmRAM was then excised as a ~3.3 kbp HindIII/SacI fragment and a ~1.8 kbp SacI/NheI fragment, which were ligated together into pMTL5402F digested with HindIII and NheI. The resulting plasmid was designated pMTL5402FLacZTTErmBtdRAM1.

The thl promoter of *C. acetobutylicum* ATCC 824 was PCR-amplified from pSOS95 (Tummala et al (2003) *J. Bacteriol.* 185: 1923-1934) using primers Thio-F1 and Thio-R-RAM. The PCR product was gel-purified and used, along with the td group I intron PCR product from the construction of ErmBtdRAM1, as template in a SOEing PCR using the outer primers Thio-F1 and tdGpI-R1. The thl promoter and part of the td intron were excised from this PCR product as a 143 bp SpeI/NspI fragment. The remainder of the td intron, and the ermB ORF from pCR2.1::ErmBtdRAM1 were excised together as a NspI/NotI fragment. These fragments were ligated in a three-way ligation into pCR2.1::ErmBtdRAM1SE linearised with SpeI and NotI, yielding plasmid pCR2.1::ErmBtdRAM2.

The Mlu1/Mlu1 fragment of pCR2.1::ErmBtdRAM2 containing the RAM was ligated with the larger Mlu1/Mlu1 fragment of pMTL20lacZTT to form pMTL20lacZTTErmBtdRAM2 as shown in FIG. 14.

A BsrGI/BstBI fragment of pMTL20lacZTTErmBtdRAM2 containing the RAM was subcloned into BsrGI/BstBI cleaved pMTL5402FlacZTTErmBtdRAM1 to generate pMTL007 as shown in FIG. 14.

pMTL007 was initially designated pMTL5402FlacZTTErmBtdRAM2, and sometimes referred to as pMTL5402FlacZTTErmRAM2 or pMTL5402FlacZTTRAM2 or pMTL5402FlacZTTR2.

Once re-targeted, the plasmid was designated pMTL007 (or pMTL5402FTTErmBtdRAM2 or pMTL5402FTTErmBRAM2 or pMTL5402FTTRAM2 or pMTL5402FTTR2) suffixed by an identifier for the 'Targeting Region' (TR). The TR is the entire region between the HindIII and BsrGI sites of the sequence generated by the re-targeting PCR. For example, once the plasmid was re-targeted to the *C. difficile* 630 gene spo0A, at position 178 of the spo0A ORF, by cloning the appropriate TR fragment in as a HindIII/BsrGI fragment, the plasmid was designated pMTL5402FTTErmBtdRAM2::Cd-spo0A-178aTR.

EXAMPLE 13

Evaluation of ErmBtdRAM2 and 3 in pMTL5402FlacZTT System in *C. sporogenes* Against codY Having generated new RAMs that were capable of giving erythromycin resistance in Clostridia, Clostridial retargeting nucleic acids comprising a modified Group II intron having targeting portions designed to target the intron to *C. sporogenes* against codY were constructed. Two plasmids were constructed bearing either the RAM2 or the RAM3 and named pMTL5402FCs-codY-417sTT::RAM2 and RAM3 respectively. The RAM2 version is identical to that depicted in FIG. 10, except the retargeting portions of the Group II intron and the IBS sequence are designed to allow retargeting of *C. sporogenes* against codY instead of *E. coli* lacZ. Either plasmid was conjugated into *Clostridium sporogenes*. Transconjugants were verified by PCR and shown to be completely sensitive to $Ery_{1.25}$. A selected transconjugant of each RAM was then induced with IPTG, and after removal of inducer by centrifugation and washing, allowed 3 hours recovery before plating out on agar plates containing a range of concentrations of erythromycin.

The number of colonies obtained is shown in Table 9 below.

TABLE 9

Results of retargeting assay

| | | Conditions | | Colonies per 100 μl 10⁰ plate | | | | | | | |
|---|---|---|---|---|---|---|---|---|---|---|---|
| | | Induction | Recovery | Ery10 | | Ery5 | | Ery2.5 | | Ery1.25 | |
| Expt | RAM | (1 mM IPTG) | (after PBS wash) | 24 h | 48 h | 24 h | 48 h | 24 h | 48 h | 24 h | 48 h |
| A | RAM2 | 1 h | 3 h | 0 | 0 | 0 | 1 | 0 | 0 | 0 | 1 |
| B | RAM2 | 3 h | 3 h | 0.2 | 1 | 1 | ~10 | 2 | ~20 | 3 | ~40 |
| C | RAM3 | 3 h | 3 h | 0 | 0.2 | 0 | 0.2 | 0 | 0.6 | 0 | 0.6 |

These data demonstrate the importance of a sufficient induction period, and the superior efficiencies achieved using RAM2 compared to RAM3.

EXAMPLE 14

Further Mutant Generation

Figure 15:
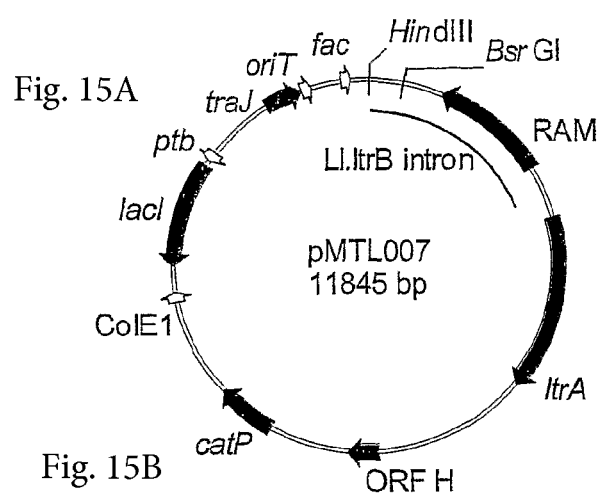

We elected to target two genes whose inactivation would lead to easily detectable phenotypes. These were pyrF and spo0A. Inactivation of the former should lead to uracil auxotrophy, while disruption of the latter should lead to asporogeny.

pMTL007 was re-targeted to the *C. sporogenes* spo0A gene and hundreds of $Em^R$ colonies of *C. sporogenes* were readily obtained after IPTG induction. DNA was extracted from four random colonies, and used as a template in PCR. In all cases, primers specific to the RAM generated a DNA fragment of a size consistent with loss of the td intron (FIG. 15).

Having demonstrated apparent functionality of the RAM with pMTL007::Csp-spo0A-249s, we proceeded to generate mutants in the two genes (pyrF and spo0A) in all three clostridial species using the protocols outlined in the methods section. PCR screening of $Em^R$ clones (FIG. 15b, c) revealed very high frequencies of insertion into the intended chromosomal site (Table 10), demonstrating how easily integrants can be obtained using this method. After isolation, single colonies of integrants were screened for plasmid loss by thiamphenicol-sensitive phenotype, and colonies cured of the plasmid were found to predominate in all these organisms without additional passaging. Insertion sites were verified by sequencing across the intron-exon junctions (Table 10) and Southern blotting with a probe for the RAM confirmed the presence of a single copy of the insertion element (FIG. 15d, e and f).

IPTG induction of intron expression from pMTL007::Csp-spo0A-249s in *C. sporogenes* increased the insertion frequency by over 100-fold (Table 10), in keeping with the reporter data from pMTL5401Fcat.

TABLE 10

Effect of regulated intron expression on insertion frequencies in *C. sporogenes*.

| Plasmid | IPTG[a] | Insertion frequency[b] | Relative insertion frequency[c] |
|---|---|---|---|
| pMTL007::Csp-spo0A-249s | − | <1.31 ± 0.34 × 10⁻⁹ | 1 |
| pMTL007::Csp-spo0A-249s | + | 1.63 ± 0.72 × 10⁻⁷ | 124 |

TABLE 10-continued

Effect of regulated intron expression on insertion frequencies in *C. sporogenes*.

| Plasmid | IPTG[a] | Insertion frequency[b] | Relative insertion frequency[c] |
|---|---|---|---|
| pMTL007::Csp-spo0A-249sΔlacI | − | 1.95 ± 0.54 × 10⁻⁶ | 1489 |

[a]Intron expression was induced with 1 mM IPTG (+) or with water in place of IPTG (−).
[b]After the recovery period, cells were spread onto TYG cycloserine plates with or without erythromycin supplementation. Insertion frequencies are expressed as $Em^R$ c.f.u./ml/total c.f.u./ml.
[c]Relative insertion frequencies are normalised to the experiment with pMTL007::Csp-spo0A-249s and water in place of IPTG.

To establish whether regulated expression of the intron conferred any advantage over constitutive expression, we de-repressed the fac promoter by introducing a frameshift mutation into the lacI gene of pMTL007::Csp-spo0A-249s. A further insertion frequency increase of over 10-fold was observed (Table 10), indicating that regulated expression of the intron confers no advantage over constitutive expression. We performed an equivalent experiment in *C. acetobutylicum* with pMTL007::Cac-spo0A-242a and observed no change in integration frequencies with the addition of IPTG (data not shown). Consistent with the pMTL5401Fcat reporter data, basal intron expression from the fac promoter in this organism is apparently sufficient to achieve easily-detectable integration frequencies. Like pMTL5401F, pMTL007 is too unstable in *C. difficile* to support the growth of its transconjugants in antibiotic-supplemented liquid culture (Purdy et al (2002) Mol. Microbiol. 46: 439-452). Therefore no comparable IPTG-induction experiments to those undertaken in *C. sporogenes* could be performed. However, in both *C. difficile* and *C. acetobutylicum*, $Em^R$ integrants could be easily obtained by simply re-streaking transconjugant colonies onto growth media containing erythromycin with no addition of IPTG.

As anticipated, all the spo0A mutants were unable to form endospores (FIG. 16). All of the pyrE mutants were shown to be unable to grow on minimal media unless supplemented with 50 μg/L uracil. We attempted to select revertants to uracil prototrophy by growing all three clostridial mutants in rich liquid media lacking erythromycin selection and then plating them onto minimal agar medium with or without uracil. Revertants were never detected on media lacking uracil in at least three experiments. By comparison to the cell counts on media supplemented with uracil, reversion frequencies per cell were estimated to be less than 9.36×10⁻⁹ in *C. difficile*, less than 9.60×10⁻⁷ in *C. acetobutylicum* and less than 5.50×10⁻⁹ in *C. sporogenes*. These findings are consistent with data in the literature (Frazier et al (2003)

*Appl. Environ. Microbiol.* 69: 1121-1128) showing that intron integrants are extremely stable—a highly desirable mutant characteristic.

EXAMPLE 15

Evaluation of ErmBtdRAM2 System Against Other Targets

A standard protocol has been developed for retargeting in Clostridia, as follows.

1. Intron Re-Targeting Sequences to the Gene of Interest are Generated Essentially to the Method Provided by Sigma with the Targetron™ kit:

The computer algorithm provided at the Sigma website [http://www.sigma-genosys.com/targetron/] is used to identify possible intron targets within the sequence of the gene of interest, and to design PCR primers. These primers are then used according to the Sigma Targetron™ protocol, and using PCR reagents provided in the Sigma Targetron™ kit, to generate a 353 bp PCR product which corresponds to part of the intron and includes modified IBS, EBS1d and EBS2 sequences such that the intron can be re-targeted to the gene of interest. This PCR product is cloned into an appropriate cloning vector such as pCR2.1 and its sequence verified. Alternatively, it may be subcloned directly into pMTL007.

2. The Prototype Clostridial Retargeting Plasmid pMTL5402FlacZTTR2 is Re-Targeted Essentially According to the Method Provided by Sigma with the Targetron™ kit:

If the PCR product of step 1 was cloned into a cloning vector, the desired re-targeting sequence is excised from its plasmid by digestion with the restriction enzymes HindIII and BsrGI, and cloned into pMTL5402FlacZTTR2 digested with the same enzymes. In either case, the resultant constructs are verified by restriction analysis and/or sequencing.

3. The Successfully Re-Targeted Clostridial Retargeting Plasmid is Transferred into the Target Organism:

Recombinant plasmids may be introduced into the clostridial hosts by standard DNA transfer methods based either on electrotransformation or conjugation. Methods for either are given in Davis I, Carter G, Young M and Minton N P (2005) "Gene Cloning in Clostridia", In: Handbook on Clostridia (Durre P, ed) pp. 37-52, CRC Press, Boca Raton, USA. In our experiments, plasmids were introduced into *Clostridium difficile* and *Clostridium sporogenes* by conjugation from *E. coli* donors. In contrast, plasmids were introduced into *Clostridium acetobutylicum* by transformation.

4. Retargeting Nucleic Acid Expression and Subsequent Integration is Achieved by Induction of the transformant with IPTG:

An individual transformant colony is used to inoculate 1.5 ml of an appropriate growth medium supplemented with 250 µg/ml cycloserine and 7.5 µg/ml thiamphenicol (the latter of which ensures plasmid maintenance) and the culture is allowed to grow to stationary phase by anaerobic incubation at 37° C. overnight. 150 µl of this culture is used to inoculate 1.5 ml of fresh broth of the same type and containing the same supplements, which is then incubated anaerobically at 37° C. As soon as growth is visible in the culture, typically after 1 hr, the culture is induced with 1 mM IPTG and incubated for 3 hrs.

5. Retargeting Nucleic Acid Integrants are Detected and Isolated Using a Recovery Step Followed by Plating of Cells onto Selective Solid Media and Incubation:

2 ml of the induced cells are harvested by centrifugation for 1 minute at 7000 rpm, washed by re-suspension in PBS and harvested as before. The pellet is re-suspended in an equal volume (2 ml) of an appropriate growth medium without supplements, and incubated anaerobically at 37° C. for 3 hrs. Serial dilutions of the culture are then plated onto an appropriate solid growth media supplemented with 1-10 µg/ml erythromycin, and incubated anaerobically at 37° C. Erythromycin resistant colonies corresponding to retargeting nucleic acid integrant clones can be picked from these plates after 18-48 hrs, depending upon the organism and erythromycin concentration used.

Optionally, serial dilutions of the culture can additionally be plated onto unsupplemented solid growth media or solid growth media supplemented with 15 µg/ml thiamphenicol in place of erythromycin in order to determine the frequency of the integration event.

The standard protocol was used to make Clostridial mutants as indicated in Table 11.

TABLE 11

Clostridial mutants

| Organism | Target | Re-Targeted[a] | Percentage In Target Gene[b] |
|---|---|---|---|
| C. sporogenes | codY | YES | Not yet determined |
| C. sporogenes | spo0A | YES | 100% (3 of 3) |
| C. sporogenes | pyrF | YES | 100% (2 of 2) |
| C. acetobutlyicum | pyrF | YES | Not yet determined |
| C. difficile | spo0A | YES | 100% (3 of 3) |

Diagnostic PCR primers give a product of the expected size if the retargeting, nucleic acid has inserted in the targeted gene.
[a]Presence of desired mutant demonstrated in a pool of several clones
[b]Several individual clones screened for desired mutation Sometimes, retargeting is inefficient. Therefore, it is recommended to try more than one targeting portion to disrupt any given gene. Furthermore, colonies may be pooled before PCR screening of combined batches. If, say portions of 10 or 100 colonies were combined and a PCR product of the size expected for a retargeted mutant was generated, colonies could then be individually screened.

EXAMPLE 16

Further Mutant Generation

To further establish the utility of the method, we selected several other genes from each of the three species, and repeated the mutagenesis procedure. The genes targeted are listed in Table 12 and the oligonucleotide primers used to generate PCR products according to the standard protocol for modification of the Group II intron of pMTL007 are shown in Table 4 or Table 13. In every case the desired integrant was obtained. Each insertion was confirmed by PCR screening and the insertion point verified by nucleotide sequencing.

TABLE 12

Intron insertion frequencies with erythromycin selection

| Target (Organism, ORF and insertion point[a]) | Em[R] clones screened[b] | Desired mutants obtained[b] | Frequency of desired mutant among Em[R] clones[b] | Insertion site verified by sequencing[b] | SEQ ID No |
|---|---|---|---|---|---|
| C. sporogenes spo0A 249s | 4 | 4 | 100% | TATGCCAAGG-intron-GTAATTGTTT | 80 |
| C. difficile spo0A 178a | 3 | 3 | 100% | ATTACATCTA-intron-GTATTAATAA | 81 |
| C. acetobutylicum spo0A 242a | 8 | 4 | 50% | TATTCTTGGA-intron-AGGTTTTCTG | 82 |
| C. sporogenes pyrF 595s | 2 | 2 | 100% | ATAGGAGCAG-intron-TAGTTGGATG | 83 |
| C. difficile pyrF 97a | 96[c] | 7-19[c] | 7-20%[c] | ACCTTAAATA-intron-TGTCTACACT | 84 |
| C. acetobutylicum pyrF 345s | 8 | 2 | 25% | CTTTGAAGGT-intron-GATTTTGAAG | 85 |
| C. acetobutylicum CAC0081 141a | 6 | 6 | 100% | TTTTAATGAC-intron-ATAGTTTATA | 86 |
| C. acetobutylicum CAC0080 121s | 6 | 6 | 100% | CTGAAATTAT-intron-TTCGTTAATA | 87 |
| C. acetobutylicum CAC0078 385a | 3 | 3 | 100% | GTATCTCCAG-intron-GCGCATATCT | 88 |
| C. acetobutylicum CAC2208 201s | 4 | 3 | 75% | TGTGGAGTAT-intron-TCGGTACACA | 89 |
| C. difficile CD0153 784a | 5 | 5 | 100% | CCAATAAGCC-intron-CATCTCCAGA | 90 |
| C. difficile CD0552 75a | 10 | 9 | 90% | CTCTACAATA-intron-TCTATCTTTA | 91 |
| C. difficile CD3563 226s | 8 | 8 | 100% | GAGGGACAGG-intron-TTGCTGTAGC | 92 |
| C. botulinum CBO0780 671a | 4 | 4 | 100% | TTTATTATTT-intron-TCTTTTTTAA[d] | 93 |
| C. botulinum CBO1120 670s | 4 | 4 | 100% | GAATTTTATG-intron-CTAATATATC[d] | 94 |
| C. botulinum CBO2762 1014s | 4 | 4 | 100% | TTTAACATAT-intron-AGATTAGTTA[d] | 95 |
| C. botulinum spo0A 249s | 4 | 4 | 100% | TATGCCAAGG-intron-GTAATTGTTT[d] | 96 |

[a]Introns were inserted after the indicated number of bases from the start of the ORF, in either the sense (s) or antisense (a) orientation.
[b]Genomic DNA was extracted from Em[R] clones picked at random and used as template in PCR using primers which amplify across an intron-exon junction. One clone of each desired mutant was selected and the intron insertion site verified by sequencing.
[c]Ninety-six Em[R] C. difficile pyrF mutant candidate clones were screened in pools. Exhaustive screening was not required to isolate the mutant, so a range of possible frequencies is given.
[d]Predicted site of insertion, not verified by nucleotide sequencing.

TABLE 13

Oligonucleotide primers

| Oligonucleotide | Sequence (5'-3') | SEQ ID No |
|---|---|---|
| Cdi-CD0552-75a-IBS | AAAAAAGCTTATAATTATCCTTATTCTCCACAATAGTGCGCCCAGATAGGGTG | 97 |
| Cdi-CD0552-75a-EBS1d | CAGATTGTACAAATGTGGTGATAACAGATAAGTCACAATATCTAACTTACCTTTCTTTGT | 98 |
| Cdi-CD0552-75a-EBS2 | TGAACGCAAGTTTCTAATTTCGGTTGAGAATCGATAGAGGAAAGTGTCT | 99 |
| Cdi-CD3563-226s-IBS | AAAAAAGCTTATAATTATCCTTAATGAGCGACAGGGTGCGCCCAGATAGGGTG | 100 |
| Cdi-CD3563-226s-EBS1d | CAGATTGTACAAATGTGGTGATAACAGATAAGTCGACAGGTTTAACTTACCTTTCTTTGT | 101 |
| Cdi-CD3563-226s-EBS2 | TGAACGCAAGTTTCTAATTTCGGTTCTCATCCGATAGAGGAAAGTGTCT | 102 |
| Cac-CAC0081-141a-IBS | AAAAAAGCTTATAATTATCCTTAATTTTCAATGACGTGCGCCCAGATAGGGTG | 103 |
| Cac-CAC0081-141a-EBS1d | CAGATTGTACAAATGTGGTGATAACAGATAAGTCAATGACATTAACTTACCTTTCTTTGT | 104 |
| Cac-CAC0081-141a-EBS2 | TGAACGCAAGTTTCTAATTTCGGTTAAAATCCGATAGAGGAAAGTGTCT | 105 |

TABLE 13-continued

Oligonucleotide primers

| Oligonucleotide | Sequence (5'-3') | SEQ ID No |
|---|---|---|
| Cac-CAC0078-385a-IBS | AAAAAAGCTTATAATT ATCCTTACTGTACCTC CAGGTGCGCCCAGATA GGGTG | 106 |
| Cac-CAC0078-385a-EBS1d | CAGATTGTACAAATGT GGTGATAACAGATAAG TCCTCCAGGCTAACTT ACCTTTCTTTGT | 107 |
| Cac-CAC0078-385a-EBS2 | TGAACGCAAGTTTCTA ATTTCGATTTACAGTC GATAGAGGAAAGTGTC T | 108 |
| Cac-CAC0080-121s-IBS | AAAAAAGCTTATAATT ATCCTTAAACTGCAAT TATGTGCGCCCAGATA GGGTG | 109 |
| Cac-CAC0080-121s-EBS1d | CAGATTGTACAAATGT GGTGATAACAGATAAG TCAATTATTTTAACTT ACCTTTCTTTGT | 110 |
| Cac-CAC0080-121s-EBS2 | TGAACGCAAGTTTCTA ATTTCGGTTCAGTTCC GATAGAGGAAAGTGTC T | 111 |
| Cac-CAC2208-201s-IBS | AAAAAAGCTTATAATT ATCCTTACATGTCGAG TATGTGCGCCCAGATA GGGTG | 112 |
| Cac-CAC2208-201s-EBS1d | CAGATTGTACAAATGT GGTGATAACAGATAAG TCGAGTATTCTAACTT ACCTTTCTTTGT | 113 |
| Cac-CAC2208-201s-EBS2 | TGAACGCAAGTTTCTA ATTTCGGTTACATGTC GATAGAGGAAAGTGTC T | 114 |
| Cdi-CD0153-784a-IBS | AAAAAAGCTTATAATT ATCCTTATACCACTAA GCCGTGCGCCCAGATA GGGTG | 115 |
| Cdi-CD0153-784a-EBS1d | CAGATTGTACAAATGT GGTGATAACAGATAAG TCTAAGCCCATAACTT ACCTTTCTTTGT | 116 |
| Cdi-CD0153-784a-EBS2 | TGAACGCAAGTTTCTA ATTTCGGTTTGGTATC GATAGAGGAAAGTGTC T | 117 |
| Cbo-CB00780-671a-IBS1 | AAAAAAGCTTATAATT ATCCTTAGCTTTCTTA TTTGTGCGCCCAGATA GGGTG | 118 |
| Cbo-CB00780-671a-EBS1d | CAGATTGTACAAATGT GGTGATAACAGATAAG TCTTATTTTCTAACTT ACCTTTCTTTGT | 119 |
| Cbo-CB00780-671a-EBS2 | TGAACGCAAGTTTCTA ATTTCGATTAAAGCTC GATAGAGGAAAGTGTC T | 120 |
| Cbo-CB01120-670s-IBS1 | AAAAAAGCTTATAATT ATCCTTACTGAACTTT ATGGTGCGCCCAGATA GGGTG | 121 |
| Cbo-CB01120-670s-EBS1d | CAGATTGTACAAATGT GGTGATAACAGATAAG TCTTTATGCTTAACTT ACCTTTCTTTGT | 122 |
| Cbo-CB01120-670s-EBS2 | TGAACGCAAGTTTCTA ATTTCGGTTTTCAGTC GATAGAGGAAAGTGTC T | 123 |
| Cbo-CB02762-1014s-IBS1 | AAAAAAGCTTATAATT ATCCTTAGATTTCACA TATGTGCGCCCAGATA GGGTG | 124 |
| Cbo-CB02762-1014s-EBS1d | CAGATTGTACAAATGT GGTGATAACAGATAAG TCACATATAGTAACTT ACCTTTCTTTGT | 125 |
| Cbo-CB02762-1014s-EBS2 | TGAACGCAAGTTTCTA ATTTCGATTAAATCTC GATAGAGGAAAGTGTC T | 126 |
| Cbo-spo0A-249s-IBS1 | AAAAAAGCTTATAATT ATCCTTACCTATCCCA AGGGTGCGCCCAGATA GGGTG | 127 |
| Cbo-spo0A-249s-EBS1d | CAGATTGTACAAATGT GGTGATAACAGATAAG TCCCAAGGGTTAACTT ACCTTTCTTTGT | 128 |
| Cbo-spo0A-249s-EBS2 | TGAACGCAAGTTTCTA ATTTCGGTTATAGGTC GATAGAGGAAAGTGTC T | 129 |

EXAMPLE 17

Construction of a catP-based RAM

A RAM containing an alternative modified selectable marker gene, namely catP, which confers resistance to chloramphenicol or thiamphenicol, was constructed.

The catP ORF was PCR-amplified from pMTL5402F plasmid DNA template using primers linker-catP-F 5'-ATACTCAGGCCTCAATTAAC-CCAAGAGA-TGCTGGTGCTTCTGGTGCTGGTATGGTATTT-GAAAAAATTGATAAAAATAGTTGGAACAG-3' (SEQ ID No. 130) and catP-MluI-R1 5'-ATACGC-GTTTAACT-ATTTATCAATTCCTGCAATTCGTTTACAAAACGGC-3' (SEQ ID No. 131), which added a small part of the td intron and linker to the 5' of the catP ORF using a primer extension.

The PCR product was digested with StuI and MluI. A portion of ErmBtdRAM2 containing the thl promoter, linker and most of the td group I intron was excised as a SpeI/StuI fragment from pCR2.1::ErmBtdRAM2. These two restriction fragments were ligated together into pCR2.1::ErmBtdRAM2 linearised with SpeI and MluI, yielding the plasmid pCR2.1::RAM-C1, which contains the new RAM element RAM-C1.

The sequence immediately preceding the catP ORF in RAM-C1 is identical to the sequence immediately preceding the ermB ORF in ErmBtdRAM2, containing the thl promoter, linker and td group I intron. The entire RAM-C1 element is flanked by MluI sites to facilitate its sub-cloning into the MluI site of the L1.LtrB intron for use as a RAM.

The RAM-C1 or a derivative thereof may be used as the RAM element in a plasmid analogous to pMTL007 to select for retargeting events in Clostridia on the basis of acquisition of thiamphenicol or chloramphenicol resistance. It will be appreciated that the selectable marker that is required to maintain the plasmid in the host must confer resistance to a different agent from the resistance conferred by the RAM. Therefore, pMTL007 will be modified by replacement of its catP selectable marker with a different selectable marker, such as ermB, which is effective in Clostridia. A plasmid modified in this way may be used for retargeting Clostridia.

As described herein, the promoter operatively linked to the region encoding the selectable marker must be capable of causing expression of the selectable marker encoded by a single copy of the selectable marker gene in an amount sufficient for the selectable marker to alter the phenotype of the Clostridial cell such that it can be distinguished from the Clostridial cell lacking the selectable marker gene. If the thl promoter in the RAM-C1 element fails to fulfil this criterion, it may be replaced or modified using methods disclosed herein. Similarly, if the positioning of the td group I intron is inappropriate either to prevent expression of the selectable marker when it is present in the RAM, or to permit expression of the selectable marker when it has spliced out of the RAM, its position may be modified. The function of the elements of the RAM may be tested using the two-plasmid system developed Karberg et al (2001) (see Example 5). Ultimately, RAM-C1, or a derivative thereof, will be used to generate retargeting mutants in Clostridia.

The invention claimed is:

1. A DNA molecule comprising:
   a modified Group II intron which does not express the intron-encoded reverse transcriptase but which contains a modified selectable marker gene in the reverse orientation relative to the modified Group II intron, wherein the modified selectable marker gene comprises a region encoding a selectable marker and a promoter operably linked to said region, wherein the promoter causes expression of the selectable marker encoded by a single copy of the modified selectable marker gene in an amount sufficient for the selectable marker to alter the phenotype of a bacterial cell of the class Clostridia such that it can be distinguished from the bacterial cell of the class Clostridia lacking the modified selectable marker gene; and a promoter for transcription of the modified Group II intron, said promoter being operably linked to said modified Group II intron; and wherein the modified selectable marker gene contains a Group I intron positioned in the forward orientation relative to the modified Group II intron so as to disrupt expression of the selectable marker;

wherein the DNA molecule allows for removal of the Group I intron from the RNA transcript of the modified Group II intron to leave a region encoding the selectable marker and allows for the insertion of said RNA transcript, or a DNA copy thereof, at a site in a DNA molecule in a bacterial cell of the class Clostridia; and wherein the selectable marker confers erythromycin resistance to the bacterial cell of the class Clostridia and wherein the promoter operably linked to the region encoding the selectable marker is the promoter of the thl gene of *C. acetobutylicum*.

2. The DNA molecule of claim 1, further comprising exons flanking the modified Group II intron, wherein the exons allow splicing of an RNA transcript of the modified Group II intron.

3. The DNA molecule of claim 2, wherein the modified Group II intron further comprises targeting portions.

4. The DNA molecule of claim 3, wherein the targeting portions guide insertion of the RNA transcript of the modified Group II intron into a site within a DNA molecule in the bacterial cell of the class Clostridia.

5. The DNA molecule of claim 4, wherein the site is a selected site.

6. The DNA molecule of claim 5, wherein the DNA molecule is a plasmid.

7. The DNA molecule of claim 6, wherein the plasmid is an *Escherichia coli*—Clostridia shuttle vector.

8. The DNA molecule of claim 7, further comprising a region permitting conjugative transfer from *Escherichia coli* to a bacterial cell of the class Clostridia.

9. The DNA molecule of claim 1, wherein the promoter operably linked to the modified Group II intron is an inducible promoter.

10. The DNA molecule of claim 9, wherein the inducible promoter is inducible by isopropyl β-D-1-thiogalactopyranoside ("IPTG") or xylose.

11. The DNA molecule of claim 9, further comprising an open reading frame encoding a Group II intron-encoded reverse transcriptase operably linked to a promoter but not contained in the modified Group II intron.

12. The DNA molecule of claim 1, wherein the bacterial cell of the class Clostridia is of the genus *Clostridium*.

13. The DNA molecule of claim 12, wherein the bacterial cell of the genus *Clostridium* is *C. thermocellum, C. acetobutylicum, C. difficile, C. botulinum, C. perfringens, C. beijerinckii, C. tetani, C. cellulyticum*, or *C. septicum*.

14. The DNA molecule of claim 5, wherein the selected site in the DNA molecule in the bacterial cell of the class Clostridia is located within a gene or within a portion of DNA which affects the expression of a gene.

15. The DNA molecule of claim 14, wherein the site is located within the chromosomal DNA of the bacterial cell of the class Clostridia.

16. A kit comprising (i) the DNA molecule of claim 1 and (ii) a DNA molecule encoding a Group II intron-encoded reverse transcriptase.

\* \* \* \* \*

SEQUENCE LISTING

```
<160> NUMBER OF SEQ ID NOS: 132

<210> SEQ ID NO 1
<211> LENGTH: 7
<212> TYPE: RNA
<213> ORGANISM: Lactococcus lactis

<400> SEQUENCE: 1 guugugg                                                             7

<210> SEQ ID NO 2
<211> LENGTH: 6
<212> TYPE: RNA
<213> ORGANISM: Lactococcus lactis

<400> SEQUENCE: 2 augugu                                                              6

<210> SEQ ID NO 3
<211> LENGTH: 10
<212> TYPE: DNA
<213> ORGANISM: Artificial Sequence
<220> FEATURE:
<223> OTHER INFORMATION: Synthetic Construct
<220> FEATURE:
<223> OTHER INFORMATION: Phage T4 td Group I intron downstream flanking
      sequence 1

<400> SEQUENCE: 3
acccaagaga                                                         10

<210> SEQ ID NO 4
<211> LENGTH: 9
<212> TYPE: DNA
<213> ORGANISM: Artificial Sequence
<220> FEATURE:
<223> OTHER INFORMATION: Synthetic Construct
<220> FEATURE:
<223> OTHER INFORMATION: Phage T4 td Group I intron downstream flanking
      sequence 2

<400> SEQUENCE: 4 acccaagaa                                                           9

<210> SEQ ID NO 5
<211> LENGTH: 11
<212> TYPE: DNA
```

```
<213> ORGANISM: Artificial Sequence
<220> FEATURE:
<223> OTHER INFORMATION: Synthetic Construct
<220> FEATURE:
<223> OTHER INFORMATION: Phage T4 td Group I intron 5' and 3' flanking
      sequence

<400> SEQUENCE: 5
gacccaagag a                                                           11

<210> SEQ ID NO 6
<211> LENGTH: 4
<212> TYPE: PRT
<213> ORGANISM: Artificial Sequence
<220> FEATURE:
<223> OTHER INFORMATION: Synthetic Construct
<220> FEATURE:
<223> OTHER INFORMATION: Phage T4 td
<220> FEATURE:
<221> NAME/KEY: MISC_FEATURE
<222> LOCATION: (4)...(4)
<223> OTHER INFORMATION: Xaa = Asp or Glu

<400> SEQUENCE: 6

Asp Pro Arg Xaa
1

<210> SEQ ID NO 7
<211> LENGTH: 4
<212> TYPE: PRT
<213> ORGANISM: Artificial Sequence
<220> FEATURE:
<223> OTHER INFORMATION: Synthetic Construct
<220> FEATURE:
<223> OTHER INFORMATION: Phage T4 td
<220> FEATURE:
<221> NAME/KEY: MISC_FEATURE
<222> LOCATION: (1)...(1)
<223> OTHER INFORMATION: Xaa = Arg or Gly

<400> SEQUENCE: 7

Xaa Pro Lys Arg
1

<210> SEQ ID NO 8
<211> LENGTH: 5
<212> TYPE: PRT
<213> ORGANISM: Artificial Sequence
<220> FEATURE:
<223> OTHER INFORMATION: Synthetic Construct
<220> FEATURE:
<223> OTHER INFORMATION: Phage T4 td
<220> FEATURE:
<221> NAME/KEY: MISC_FEATURE
<222> LOCATION: (1)...(1)
<223> OTHER INFORMATION: Xaa = Gly, Glu, Ala, Val, Leu, Ser, Trp, Pro,
      Gln, Arg, Met, Thr or Lys
<220> FEATURE:
<221> NAME/KEY: MISC_FEATURE
<222> LOCATION: (5)...(5)
<223> OTHER INFORMATION: Xaa = Lys, Ser, Arg, Ile, Met, Thr or Asn

<400> SEQUENCE: 8

Xaa Thr Gln Glu Xaa
1               5

<210> SEQ ID NO 9
<211> LENGTH: 39
<212> TYPE: DNA
<213> ORGANISM: Artificial Sequence
<220> FEATURE:
```

```
<223> OTHER INFORMATION: Synthetic Construct
<220> FEATURE:
<223> OTHER INFORMATION: Intronless copy of the ltrB gene, 5' to 3'

<400> SEQUENCE: 9
cacgtcgatc gtgaacacat ccataaccat atcattttt                              39

<210> SEQ ID NO 10
<211> LENGTH: 39
<212> TYPE: DNA
<213> ORGANISM: Artificial Sequence
<220> FEATURE:
<223> OTHER INFORMATION: Synthetic Construct
<220> FEATURE:
<223> OTHER INFORMATION: td intron/exon linker sequence
<220> FEATURE:
<221> NAME/KEY: MISC_FEATURE
<222> LOCATION: (4)...(5)
<223> OTHER INFORMATION: td intron inserted between nucleotides 4 and 5

<400> SEQUENCE: 10
atggacccaa gagatgctgg tgcttctggt gctggtatg                              39

<210> SEQ ID NO 11
<211> LENGTH: 39
<212> TYPE: DNA
<213> ORGANISM: Artificial Sequence
<220> FEATURE:
<223> OTHER INFORMATION: Synthetic Construct
<220> FEATURE:
<223> OTHER INFORMATION: Modified ermB gene

<400> SEQUENCE: 11
atggacccaa gagatgctgg tgcttctggt gctggtatg                              39

<210> SEQ ID NO 12
<211> LENGTH: 13
<212> TYPE: PRT
<213> ORGANISM: Enterococcus faecalis
<220> FEATURE:
<223> OTHER INFORMATION: ErmB

<400> SEQUENCE: 12

Met Asp Pro Arg Asp Ala Gly Ala Ser Gly Ala Gly Met
1               5                   10

<210> SEQ ID NO 13
<211> LENGTH: 1318
<212> TYPE: DNA
<213> ORGANISM: Artificial Sequence
<220> FEATURE:
<223> OTHER INFORMATION: Synthetic Construct
<220> FEATURE:
<223> OTHER INFORMATION: ErmBtdRAM1 sequence

<400> SEQUENCE: 13
ctacgcgtgg aaataagact tagaagcaaa cttaagagtg tgttgatagt gcagtatctt      60 aaaatttgt ataataggaa ttgaagttaa attagatgct aaaaatttgt aattaagaag      120
gagtgattac atggcattat gttcagataa ggtcgttaat cttacccegg aattatatcc      180 agctgcatgt caccatgcag agcagactat atctccaact tgttaaagca agttgtctat      240
cgtttcgagt cacttgaccc tactccccaa agggatagtc gttaggcatt tatgtagaac      300
caattccatt tatcagattt tacacgataa gtaactaatc cagacgaaat ttctctctaga     360 gaaagtattt ttaatctgat aaattccgct tttcataaat acctctttaa atatagaagt     420
```

```
atttattaaa gggcagtcct acaatttagc acgggattgt ctactagaga ggttccccgt    480
ttagatagat tacaagtata agtcaccttagtactcaggcc tcaattaacc caagagatgc    540
```
(corrections made where visible)

```
atttattaaa gggcagtcct acaatttagc acgggattgt ctactagaga ggttccccgt    480
ttagatagat tacaagtata agtcaccttatactcaggcc  tcaattaacc caagagatgc    540
tggtgcttct ggtgctggta tgaacaaaaa tataaaatat tctcaaaact ttttaacgag    600
tgaaaaagta ctcaaccaaa taataaaaca attgaattta aaagaaaccg ataccgttta    660
cgaaattgga acaggtaaag ggcatttaac gacgaaactg gctaaaataa gtaaacaggt    720
aacgtctatt gaattagaca gtcatctatt caacttatcg tcagaaaaat taaaactgaa    780
tactcgtgtc actttaattc accaagatat tctacagttt caattccctacaaacagag     840 gtataaaatt gttgggagta ttccttacca tttaagcaca caaattatta aaaaagtggt    900
ttttgaaagc catgcgtctg acatctatct gattgttgaa gaaggattct acaagcgtac    960
cttggatatt caccgaacac tagggttgct cttgcacact caagtctcga ttcagcaatt   1020
gcttaagctg ccagcggaat gctttcatcc taaaccaaaa gtaaacagtg tcttaataaa   1080
acttacccgc cataccacag atgttccaga taaatattgg aagctatata cgtactttgt   1140
ttcaaaatgg gtcaatcgag aatatcgtca actgttttact aaaaatcagt ttcatcaagc  1200
aatgaaacac gccaaagtaa acaatttaag taccgttact tatgagcaag tattgtctat   1260
ttttaatagt tatctattat ttaacgggag gaaataattc tatgagtcgc acgcgttc    1318
```

<210> SEQ ID NO 14
<211> LENGTH: 62
<212> TYPE: DNA
<213> ORGANISM: Artificial Sequence
<220> FEATURE:
<223> OTHER INFORMATION: Synthetic Construct
<220> FEATURE:
<223> OTHER INFORMATION: pBRR3-LtrB cloning site

<400> SEQUENCE: 14

```
ccgacgtcac ccacgtcgat cgtgaacaca tccataacca tatcattttt aatgaattct    60
aa                                                                   62
```

<210> SEQ ID NO 15
<211> LENGTH: 111
<212> TYPE: DNA
<213> ORGANISM: Artificial Sequence
<220> FEATURE:
<223> OTHER INFORMATION: Synthetic Construct
<220> FEATURE:
<223> OTHER INFORMATION: pCR2.1-TOPO cloning site

<400> SEQUENCE: 15

```
ttggtaccga gctcggatcc actagtaacg gccgccagtg tgctggaatt cgcccttaag    60
ggcgaattct gcagatatcc atcacactgg cggccgctcg agcatgcatc t            111
```

<210> SEQ ID NO 16
<211> LENGTH: 52
<212> TYPE: DNA
<213> ORGANISM: Artificial Sequence
<220> FEATURE:
<223> OTHER INFORMATION: Synthetic Construct
<220> FEATURE:
<223> OTHER INFORMATION: Multicloning site fragment

<400> SEQUENCE: 16

```
acgtctcgag gtaccatgca taggcctgag ctcactagtg cggccgcgaa tt             52
```

<210> SEQ ID NO 17
<211> LENGTH: 57

```
<212> TYPE: DNA
<213> ORGANISM: Artificial Sequence
<220> FEATURE:
<223> OTHER INFORMATION: Synthetic Construct
<220> FEATURE:
<223> OTHER INFORMATION: pBRR3-MCS1 cloning site

<400> SEQUENCE: 17
ccgacgtctc gaggtaccat gcataggcct gagctcacta gtgcggccgc gaattct      57

<210> SEQ ID NO 18
<211> LENGTH: 29
<212> TYPE: DNA
<213> ORGANISM: Clostridium acetobutylicum

<400> SEQUENCE: 18
ttgataaaaa taataatagt gggtataat                                     29

<210> SEQ ID NO 19
<211> LENGTH: 28
<212> TYPE: DNA
<213> ORGANISM: Artificial Sequence
<220> FEATURE:
<223> OTHER INFORMATION: Synthetic Construct
<220> FEATURE:
<223> OTHER INFORMATION: thl2 promoter sequence

<400> SEQUENCE: 19
ttcctaaaat aataatagtg ggtaaaat                                      28

<210> SEQ ID NO 20
<211> LENGTH: 29
<212> TYPE: DNA
<213> ORGANISM: Artificial Sequence
<220> FEATURE:
<223> OTHER INFORMATION: Synthetic Construct
<220> FEATURE:
<223> OTHER INFORMATION: Consensus promoter sequence
<220> FEATURE:
<221> NAME/KEY: MISC_FEATURE
<222> LOCATION: (7)...(7)
<223> OTHER INFORMATION: n = a, g, t or c
<220> FEATURE:
<221> NAME/KEY: MISC_FEATURE
<222> LOCATION: (8)...(8)
<223> OTHER INFORMATION: n = a, g, t or c
<220> FEATURE:
<221> NAME/KEY: MISC_FEATURE
<222> LOCATION: (9)...(9)
<223> OTHER INFORMATION: n = a, g, t or c
<220> FEATURE:
<221> NAME/KEY: MISC_FEATURE
<222> LOCATION: (10)...(10)
<223> OTHER INFORMATION: n = a, g, t or c
<220> FEATURE:
<221> NAME/KEY: MISC_FEATURE
<222> LOCATION: (11)...(11)
<223> OTHER INFORMATION: n = a, g, t or c
<220> FEATURE:
<221> NAME/KEY: MISC_FEATURE
<222> LOCATION: (12)...(12)
<223> OTHER INFORMATION: n = a, g, t or c
<220> FEATURE:
<221> NAME/KEY: MISC_FEATURE
<222> LOCATION: (13)...(13)
<223> OTHER INFORMATION: n = a, g, t or c
<220> FEATURE:
<221> NAME/KEY: MISC_FEATURE
<222> LOCATION: (14)...(14)
<223> OTHER INFORMATION: n = a, g, t or c
<220> FEATURE:
<221> NAME/KEY: MISC_FEATURE
<222> LOCATION: (15)...(15)
```

```
<223> OTHER INFORMATION: n = a, g, t or c
<220> FEATURE:
<221> NAME/KEY: MISC_FEATURE
<222> LOCATION: (16)...(16)
<223> OTHER INFORMATION: n = a, g, t or c
<220> FEATURE:
<221> NAME/KEY: MISC_FEATURE
<222> LOCATION: (17)...(17)
<223> OTHER INFORMATION: n = a, g, t or c
<220> FEATURE:
<221> NAME/KEY: MISC_FEATURE
<222> LOCATION: (18)...(18)
<223> OTHER INFORMATION: n = a, g, t or c
<220> FEATURE:
<221> NAME/KEY: MISC_FEATURE
<222> LOCATION: (19)...(19)
<223> OTHER INFORMATION: n = a, g, t or c
<220> FEATURE:
<221> NAME/KEY: MISC_FEATURE
<222> LOCATION: (20)...(20)
<223> OTHER INFORMATION: n = a, g, t or c
<220> FEATURE:
<221> NAME/KEY: MISC_FEATURE
<222> LOCATION: (21)...(21)
<223> OTHER INFORMATION: n = a, g, t or c
<220> FEATURE:
<221> NAME/KEY: MISC_FEATURE
<222> LOCATION: (22)...(22)
<223> OTHER INFORMATION: n = a, g, t or c
<220> FEATURE:
<221> NAME/KEY: MISC_FEATURE
<222> LOCATION: (23)...(23)
<223> OTHER INFORMATION: n = a, g, t or c

<400> SEQUENCE: 20
ttgacannnn nnnnnnnnnn nnntataat                                  29

<210> SEQ ID NO 21
<211> LENGTH: 1275
<212> TYPE: DNA
<213> ORGANISM: Artificial Sequence
<220> FEATURE:
<223> OTHER INFORMATION: Synthetic Construct
<220> FEATURE:
<223> OTHER INFORMATION: ErmBtdRAM2 sequence

<400> SEQUENCE: 21
ctactagtac gcgttatatt gataaaaata ataatagtgg gtataattaa gttgttagag    60
aaaacgtata aattaggagg gattcatatg gcattatgtt cagataaggt cgttaatctt   120
accccggaat tatatccagc tgcatgtcac catgcagagc agactatatc tccaacttgt   180
taaagcaagt tgtctatcgt ttcgagtcac ttgaccctac tccccaaagg gatagtcgtt   240
aggcatttat gtagaaccaa ttccatttat cagattttac acgataagta actaatccag   300
acgaaatttt ctctagagaa agtattttta atctgataaa ttccgctttt cataaatacc   360
tctttaaata tagaagtatt tattaaaggg cagtcctaca atttagcacg ggattgtcta   420
ctagagaggt tccccgttta gatagattac aagtataagt caccttatac tcaggcctca   480
attaacccaa gagatgctgg tgcttctggt gctggtatga acaaaaatat aaaatattct   540
caaaactttt taacgagtga aaaagtactc aaccaaataa taaaacaatt gaatttaaaa   600
gaaaccgata ccgtttacga aattggaaca ggtaaagggc atttaacgac gaaactggct   660
aaaataagta acaggtaac gtctattgaa ttagacagtc atcattcaa cttatcgtca   720 gaaaaattaa aactgaatac tcgtgtcact ttaattcacc agatattct acagtttcaa   780 ttccctaaca aacagaggta taaaattgtt gggagtattc cttaccattt aagcacacaa   840
attattaaaa aagtggtttt tgaaagccat gcgtctgaca tctatctgat tgttgaagaa   900
```

```
ggattctaca agcgtacctt ggatattcac cgaacactag ggttgctctt gcacactcaa    960
gtctcgattc agcaattgct taagctgcca gcggaatgct ttcatcctaa accaaaagta   1020
aacagtgtct taataaaact tacccgccat accacagatg ttccagataa atattggaag   1080
ctatatacgt actttgtttc aaaatgggtc aatcgagaat atcgtcaact gtttactaaa   1140
aatcagtttc atcaagcaat gaaacacgcc aaagtaaaca atttaagtac cgttacttat   1200
gagcaagtat tgtctatttt taatagttat ctattattta acgggaggaa ataattctat   1260
gagtcgcacg cgttc                                                   1275

<210> SEQ ID NO 22
<211> LENGTH: 11821
<212> TYPE: DNA
<213> ORGANISM: Artificial Sequence
<220> FEATURE:
<223> OTHER INFORMATION: Synthetic Construct
<220> FEATURE:
<223> OTHER INFORMATION: pMTL5402FlacZTTErmBtdRAM2 (aka pMTL007)

<400> SEQUENCE: 22
agcttataat tatccttacg tgacggttaa gtgcgcccag ataggggtgtt aagtcaagta     60 gtttaaggta ctactctgta agataacaca gaaaacagcc aacctaaccg aaaagcgaaa    120
gctgatacgg gaacagagca cggttggaaa gcgatgagtt acctaaagac aatcgggtac    180
gactgagtcg caatgttaat cagatataag gtataagttg tgtttactga acgcaagttt    240
ctaatttcgg tttcacgtcg atagaggaaa gtgtctgaaa cctctagtac aaagaaaggt    300
aagttacgtt aaccgactta tctgttatca ccacatttgt acaatctgta ggagaaccta    360
tgggaacgaa acgaaagcga tgccgagaat ctgaatttac caagacttaa cactaactgg    420 ggataccta  aacaagaatg cctaatagaa aggaggaaaa aggctatagc actagagctt    480
gaaaatcttg caagggtacg gagtactcgt agtagtctga aagggtaac  gcccctttaca   540 tggcaaaggg gtacagttat tgtgtactaa aattaaaaat tgattaggga ggaaaacctc    600
aaaatgaaac caacaatggc aattttagaa agaatcagta aaaattcaca agaaaatata    660
gacgaagttt ttacaagact ttatcgttat cttttacgtc cagatattta ttacgtggcg    720
acgcgtgcga ctcatagaat tatttcctcc cgttaaataa tagataacta ttaaaaatag    780
acaatacttg ctcataagta acggtactta aattgtttac tttggcgtgt ttcattgctt    840
gatgaaactg attttagta aacagttgac gatattctcg attgacccat tttgaaacaa    900
agtacgtata tagcttccaa tatttatctg gaacatctgt ggtatggcgg gtaagtttta    960
ttaagacact gtttactttt ggtttaggat gaaagcattc cgctggcagc ttaagcaatt   1020
gctgaatcga gacttgagtg tgcaagagca accctagtgt tcggtgaata tccaaggtac   1080
gcttgtagaa tccttcttca acaatcagat agatgtcaga cgcatggctt tcaaaaacca   1140 ctttttttaat aatttgtgtg cttaaatggt aaggaatact cccaacaatt ttatacctct   1200
gtttgttagg gaattgaaac tgtagaatat cttggtgaat taaagtgaca cgagtattca   1260 gttttaatttt ttctgacgat aagttgaata gatgactgtc taattcaata gacgttacct   1320
gtttacttat tttagccagt ttcgtcgtta aatgcccttt acctgttcca atttcgtaaa   1380
cggtatcggt ttctttttaaa ttcaattgtt ttattatttg gttgagtact ttttcactcg   1440
ttaaaaagtt ttgagaatat tttatatttt tgttcatacc agcaccagaa gcaccagcat   1500
ctcttgggtt aattgaggcc tgagtataag gtgacttata cttgtaatct atctaaacgg   1560
```

```
ggaacctctc tagtagacaa tcccgtgcta aattgtagga ctgcccttta ataaatactt    1620
ctatatttaa agaggtattt atgaaaagcg gaatttatca gattaaaaat actttctcta    1680
gagaaatttt cgtctggatt agttacttat cgtgtaaaat ctgataaatg gaattggttc    1740
tacataaatg cctaacgact atcccttttgg ggagtagggt caagtgactc gaaacgatag   1800
acaacttgct ttaacaagtt ggagatatag tctgctctgc atggtgacat gcagctggat    1860
ataattccgg ggtaagatta acgaccttat ctgaacataa tgccatatga atccctccta    1920
atttatacgt tttctctaac aacttaatta tacccactat tattattttt atcaatataa    1980
cgcgttggga aatggcaatg atagcgaaac aacgtaaaac tcttgttgta tgctttcatt    2040
gtcatcgtca cgtgattcat aaacacaagt gaatgtcgac agtgaatttt tacgaacgaa    2100
caataacaga gccgtatact ccgagagggg tacgtacggt tcccgaagag ggtggtgcaa    2160
accagtcaca gtaatgtgaa caaggcggta cctccctact tcaccatatc attttctgca    2220 gcccccctaga aataattttg tttaacttta agaaggagat atacatatat ggctagatcg    2280
tccattccga cagcatcgcc agtcactatg gcgtgctgct agcgctatat gcgttgatgc    2340
aatttctatg cactcgtagt agtctgagaa gggtaacgcc ctttacatgg caaaggggta    2400
cagttattgt gtactaaaat taaaaattga ttagggagga aaacctcaaa atgaaaccaa    2460
caatggcaat tttagaaaga atcagtaaaa attcacaaga aaatatagac gaagttttta    2520
caagacttta tcgttatctt ttacgtccag atatttatta cgtggcgtat caaaattttat   2580 attccaataa aggagcttcc acaaaaggaa tattagatga tacagcggat ggctttagtg    2640
aagaaaaaat aaaaaagatt attcaatctt taaaagacgg aacttactat cctcaacctg    2700
tacgaagaat gtatattgca aaaaagaatt ctaaaaagat gagacccttta ggaattccaa   2760 cttttcacaga taaattgatc caagaagctg tgagaataat tcttgaatct atctatgaac    2820
cggtattcga agatgtgtct cacggttttta gacctcaacg aagctgtcac acagctttga    2880
aaacaatcaa aagagagttt ggcggcgcaa gatggtttgt ggagggagat ataaaaggct    2940
gcttcgataa tatagaccac gttacactca ttggactcat caatcttaaa atcaaagata    3000
tgaaaatgag ccaattgatt tataaatttc taaaagcagg ttatctggaa aactggcagt    3060
atcacaaaac ttacagcgga acacctcaag gtggaattct atctcctctt ttggccaaca    3120
tctatcttca tgaattggat aagtttgttt tacaactcaa aatgaagttt gaccgagaaa    3180
gtccagaaag aataacacct gaatatcggg agctccacaa tgagataaaa agaatttctc    3240
accgtctcaa gaagttggag ggtgaagaaa aagctaaagt tctttttagaa tatcaagaaa    3300 aacgtaaaag attacccaca ctcccctgta cctcacagac aaataaagta ttgaaatacg    3360
tccggtatgc ggacgacttc attatctctg ttaaaggaag caaagaggac tgtcaatgga    3420
taaaagaaca attaaaactt tttattcata acaagctaaa aatggaattg agtgaagaaa    3480
aaacactcat cacacatagc agtcaacccg ctcgttttct gggatatgat atacgagtaa    3540
ggagatctgg aacgataaaa cgatctggta aagtcaaaaa gagaacactc aatgggagtg    3600
tagaactcct tattcctctt caagacaaaa ttcgtcaatt tatttttgac aagaaaatag    3660
ctatccaaaa gaaagatagc tcatggtttc cagttcacag gaaatatctt attcgttcaa    3720
cagacttaga aatcatcaca atttataatt ctgaactccg cgggatttgt aattactacg    3780
gtctagcaag taattttaac cagctcaatt attttgctta tcttatggaa tacagctgtc    3840
taaaaacgat agcctccaaa cataagggaa cactttcaaa aaccatttcc atgtttaaag    3900
atggaagtgg ttcgtggggg atcccgtatg agataaagca aggtaagcag cgccgttatt    3960
```

```
ttgcaaattt tagtgaatgt aaatcccctt atcaatttac ggatgagata agtcaagctc    4020
ctgtattgta tggctatgcc cggaatactc ttgaaaacag gttaaaagct aaatgttgtg    4080
aattatgtgg gacgtctgat gaaaatactt cctatgaaat tcaccatgtc aataaggtca    4140
aaaatcttaa aggcaaagaa aaatgggaaa tggcaatgat agcgaaacaa cgtaaaactc    4200
ttgttgtatg ctttcattgt catcgtcacg tgattcataa acacaagtga atgtcgagca    4260
cccgttctcg gagcactgtc cgaccgcttt ggccgccgcc cagtcctgct cgcttcgcta    4320
cttggagcca ctatcgacta cgcgatcatg gcgaccacac ccgtcctgtg gatcgccaag    4380
ctcgccgatg gtagtgtggg gtctccccat gcgagagtag ggaactgcca ggcatcaaat    4440
aaaacgaaag gctcagtcga aagactgggc ctttcgtttt atctgttgtt tgtcggtgaa    4500
cgctctcctg agtaggacaa atccgccggg agcggatttg aacgttgcga agcaacggcc    4560
cggagggtgg cgggcaggac gcccgccata aactgccagg catcaaatta gcagaaggc     4620 catcctgacg gatggccttt ttgcgtttct acaaactctt cctgtcgtca tatctacaag    4680 ccatccccccc acagatacgg taaactagcc tcgttttgc atcaggaaag cagaacgcca    4740
tgagcggcct catttcttat tctgagttac aacagtccgc accgctgtcc ggtagctcct    4800
tccggtgggc gcggggcatg actatcgtcg ccgcacttat gactgtcttc tttatcatgc    4860
aactcgtagg acaggtgcca gcttggcact ggccgtcgtt ttacaacgtc gtgactggga    4920
aaaccctggc gttacccaac ttaatcgcct tgcagcacat ccccctttcg ccagctggcg    4980
taatagcgaa gaggcccgca ccgatcgccc ttcccaacag ttgcgcagcc tgaatggcga    5040
atggcgctag cgaagagatg cagcagccat tattttttg aacaattgac aattcatttc     5100
ttatttttta ttaagtgata gtcaaaaggc ataacagtgc tgaatagaaa gaaatttaca    5160
gaaaagaaaa ttatagaatt tagtatgatt aattatactc atttatgaat gtttaattga    5220
atacaaaaaa aaatacttgt tatgtattca attacgggtt aaaatataga caagttgaaa    5280
aatttaataa aaaaataagt cctcagctct tatatattaa gctaccaact tagtatataa    5340
gccaaaactt aaatgtgcta ccaacacatc aagccgttag agaactctat ctatagcaat    5400
atttcaaatg taccgacata caagagaaac attaactata tatattcaat ttatgagatt    5460
atcttaacag atataaatgt aaattgcaat aagtaagatt tagaagttta tagcctttgt    5520
gtattggaag cagtacgcaa aggcttttt atttgataaa aattagaagt atatttattt     5580
tttcataatt aatttatgaa atgaaaggg ggtgagcaaa gtgacagagg aaagcagtat     5640
cttatcaaat aacaaggtat tagcaatatc attattgact ttagcagtaa acattatgac    5700
ttttatagtg cttgtagcta agtagtacga aggggagc tttaaaaagc tccttggaat      5760
acatagaatt cataaattaa tttatgaaaa gaagggcgta tatgaaaact tgtaaaaatt    5820
gcaaagagtt tattaaagat actgaaatat gcaaaataca ttcgttgatg attcatgata    5880
aaacagtagc aacctattgc agtaaataca atgagtcaag atgtttacat aaagggaaag    5940
tccaatgtat taattgttca agatgaacc gatatggatg gtgtgccata aaaatgagat     6000 gtttacaga ggaagaacag aaaaaagaac gtacatgcat taaatattat gcaaggagct    6060 ttaaaaagc tcatgtaaag aagagtaaaa agaaaaaata atttattat taatttaata     6120 ttgagagtgc cgacacagta tgcactaaaa aatatatctg tggtgtagtg agccgataca    6180
aaaggatagt cactcgcatt ttcataatac atcttatgtt atgattatgt gtcggtggga    6240
cttcacgacg aaaacccaca ataaaaaaag agttcggggt agggttaagc atagttgagg    6300
```

```
caactaaaca atcaagctag gatatgcagt agcagaccgt aaggtcgttg tttaggtgtg    6360
ttgtaataca tacgctatta agatgtaaaa atacggatac caatgaaggg aaaagtataa    6420
tttttggatg tagtttgttt gttcatctat gggcaaacta cgtccaaagc cgtttccaaa    6480
tctgctaaaa agtatatcct ttctaaaatc aaagtcaagt atgaaatcat aaataaagtt    6540
taattttgaa gttattatga tattatgttt ttctattaaa ataaattaag tatatagaat    6600
agtttaataa tagtatatac ttaatgtgat aagtgtctga cagctgaccg gtctaaagag    6660
gtccctagcg cctacgggga atttgtatcg ataaggggta caaattccca ctaagcgctc    6720
ggcggggatc gatcccgggt acgtacccgg cagtttttct ttttcggcaa gtgttcaaga    6780
agttattaag tcgggagtgc agtcgaagtg ggcaagttga aaaattcaca aaaatgtggt    6840
ataatatctt tgttcattag agcgataaac ttgaatttga gagggaactt agatggtatt    6900
tgaaaaaatt gataaaaata gttggaacag aaaagagtat tttgaccact actttgcaag    6960
tgtaccttgt acctacagca tgaccgttaa agtggatatc acacaaataa aggaaaaggg    7020
aatgaaacta tatcctgcaa tgctttatta tattgcaatg attgtaaacc gccattcaga    7080
gtttaggacg gcaatcaatc aagatggtga attggggata tatgatgaga tgataccaag    7140
ctatacaata tttcacaatg atactgaaac attttccagc ctttggactg agtgtaagtc    7200
tgactttaaa tcatttttag cagattatga aagtgatacg caacggtatg gaaacaatca    7260
tagaatggaa ggaaagccaa atgctccgga aaacattttt aatgtatcta tgataccgtg    7320
gtcaaccttc gatggcttta atctgaattt gcagaaagga tatgattatt tgattcctat    7380
ttttactatg gggaaatatt ataaagaaga taacaaaatt atacttcctt tggcaattca    7440
agttcatcac gcagtatgtg acggatttca catttgccgt tttgtaaacg aattgcagga    7500
attgataaat agttaacttc aggtttgtct gtaactaaaa acaagtattt aagcaaaaac    7560
atcgtagaaa tacggtgttt tttgttaccc taaaatctac aattttatac ataaccacag    7620
gttagtacaa agaccttgtg tttcttttg aaaggcttaa acaaggatt tttccttgat      7680
ttaagccccg aaaagcaaca caaccaaggt tttagtatca atctgtggtt tttatatttt    7740
cagagaccgg tcaggagtca ggcaactatg gatgaacgaa atagacagat cgctgagata    7800
ggtgcctcac tgattaagca ttggtaactg tcagaccaag tttactcata tatactttag    7860
attgatttaa aacttcattt ttaatttaaa aggatctagg tgaagatcct ttttgataat    7920
ctcatgacca aaatccctta acgtgagttt tcgttccact gagcgtcaga ccccgtagaa    7980
aagatcaaag gatcttcttg agatcctttt tttctgcgcg taatctgctg cttgcaaaca    8040
aaaaaaccac cgctaccagc ggtggtttgt ttgccggatc aagagctacc aactcttttt    8100
ccgaaggtaa ctggcttcag cagagcgcag ataccaaata ctgtccttct agtgtagccg    8160
tagttaggcc accacttcaa gaactctgta gcaccgccta catacctcgc tctgctaatc    8220
ctgttaccag tggctgctgc cagtggcgat aagtcgtgtc ttaccgggtt ggactcaaga    8280
cgatagttac cggataaggc gcagcggtcg ggctgaacgg ggggttcgtg cacacagccc    8340
agcttggagc gaacgaccta caccgaactg agatacctac agcgtgagca ttgagaaagc    8400
gccacgcttc ccgaagggag aaaggcggac aggtatccgg taagcggcag gtcggaaca     8460
ggagagcgca cgagggagct ccaggggga aacgcctggt atctttatag tcctgtcggg     8520
tttcgccacc tctgacttga gcgtcgattt tgtgatgct cgtcaggggg gcggagccta     8580
tggaaaaacg ccagcaacgc ggcctttta cggttcctgg ccttttgctg ccttttgct      8640
cacatgttct ttcctgcgtt atcccctgat tctgtggata accgtattac cgcctttgag    8700
```

```
tgagctgata ccgctcgccg cagccgaacg accgagcgca gcgagtcagt gagcgaggaa    8760
gcggaagcag taagacgggt aagcctgttg atgataccgc tgccttactg ggtgcattag    8820
ccagtctgaa tgacctgtca cgggataatt cctaactcac attaattgcg ttgcgctcac    8880
tgcccgcttt ccagtcggga aacctgtcgt gccagctgca ttaatgaatc ggccaacgcg    8940
cggggagagg cggtttgcgt attgggcgcc agggtggttt ttcttttcac cagtgagacg    9000
ggcaacagct gattgccctt caccgcctgg ccctgagaga gttgcagcaa gcggtccacg    9060
ctggtttgcc ccagcaggcg aaaatcctgt ttgatggtgg ttgacggcgg atataacat    9120 gagctgtctt cggtatcgtc gtatcccact accgagatat ccgcaccaac gcgcagcccg    9180
gactcggtaa tggcgcgcat tgcgcccagc gccatctgat cgttggcaac cagcatcgca    9240
gtgggaacga tgccctcatt cagcatttgc atggtttgtt gaaaaccgga catggcactc    9300
cagtcgcctt cccgttccgc tatcggctga atttgattgc gagtgagata tttatgccag    9360
ccagccagac gcagacgcgc cgagacagaa cttaatgggc ccgctaacag cgcgatttgc    9420
tggtgaccca atgcgaccag atgctccacg cccagtcgcg taccgtcttc atgggagaaa    9480
ataatactgt tgatgggtgt ctggtcagag acatcaagaa ataacgccgg aacattagtg    9540
caggcagctt ccacagcaat ggcatcctgg tcatccagcg gatagttaat gatcagccca    9600
ctgacgcgtt gcgcgagaag attgtgcacc gccgctttac aggcttcgac gccgcttcgt    9660
tctaccatcg acaccaccac gctggcaccc agttgatcgg cgcgagattt aatcgccgcg    9720
acaatttgcg acggcgcgtg cagggccaga ctggaggtgg caacgccaat cagcaacgac    9780
tgtttgcccg ccagttgttg tgccacgcgg ttgggaatgt aattcagctc cgccatcgcc    9840
gcttccactt tttcccgcgt tttcgcagaa acgtggctgg cctggttcac cacgcgggaa    9900
acggtctgat aagagacacc ggcatactct gcgacatcgt ataacgttac tggtttcata    9960
tgttgcacct ctactttaat aattttttaac ttttatatat gattaattta attgtttgtt    10020
aaatttatat caatcaatgc tatgaatatt tctttatacc ttattgtaac aaaaaaatat    10080
tggaaatgtt gaattttcag atatattatt ttattatatt attaattta tatattcatt     10140 tttataagat ttcacaacac gaacgtaata taatatatct tcctcatctt ctgaaaagat    10200
tatactaatt ctattcatgt tacttataat cttattttgg taaatcgaat ttttcaatta    10260
tatgttcggc aacctttatc ccatcaacag ccgctgatat tataccacct gcaaatcctg    10320 cccccttctcc agttggataa agtccgcata catttatact ttcaagtgaa gcatttctat    10380
tcaatctaac tggtgctgat gttcttgtct caattcccgt taaaattgca tcttctcttg    10440
catacccttt tatcttttta tcaaaattta taattccttc tttaagagcc tctacaacat    10500
aatcaggtaa acattctttt aattccctga attatctgca gaattcgccc ttcctgcttc    10560
ggggtcatta tagcgatttt ttcggtatat ccatcctttt tcgcacgata tacaggattt    10620
tgccaaaggg ttcgtgtaga ctttccttgg tgtatccaac ggcgtcagcc gggcaggata    10680
ggtgaagtag gcccacccgc gagcgggtgt tccttcttca ctgtccctta ttcgcacctg    10740
gcggtgctca acgggaatcc tgctctgcga ggctggccgg ctaccgccgg cgtaacagat    10800
gagggcaagc ggatggctga tgaaaccaag ccaaccagga agggcagccc acctatcaag    10860
gtgtactgcc ttccagacga acgaagagcg attgaggaaa aggcggcggc ggccggcatg    10920
agcctgtcgg cctacctgct ggccgtcggc cagggctaca aaatcacggg cgtcgtggac    10980
tatgagcacg tccgcgagct ggcccgcatc aatggcgacc tgggccgcct gggcggcctg    11040
```

```
ctgaaactct ggctcaccga cgacccgcgc acggcgcggt tcggtgatgc cacgatcctc    11100
gccctgctgg cgaagatcga agagaagcag gacgagcttg gcaaggtcat gatgggcgtg    11160
gtccgcccga gggcagagcc atgactttt tagccgctaa aacggccggg gggtgcgcgt     11220
gattgccaag cacgtcccca tgcgctccat caagaagagc gacttcgcgg agctggtgaa    11280
gtacatcacc gacgagcaag gcaagaccga tccccatccc gaagtggtca gactggaaaa    11340
tcagagggca ggaactgcga acagcaaaaa gtcagatagc accacatagc agacccgcca    11400
taaaacgccc tgagagcccg tgacgggctt ttcttgtatt atgggtagtt tccttgcatg    11460
aatccataaa aggcgcccaa tacgcaaacc gcctctcccc gcgcgttggc cgattcatta    11520
atgcagaatt ccccggatcg agatagtata tgatgcatat tctttaaata tagataaagt    11580
tatagaagca atagaagatt taggatttac tgtaatataa attacacttt taaaaagttt    11640
aaaaacatga tacaataagt tatggttgga attgttatcc gctcacaatt ccaacttatg    11700
attaaaattt taaggaggtg tatttcatat gaccatgatt acgaattcga gctcggtacc    11760
cggggatcct ctagagtcga cgtcacgcgt ccatggagat ctcgaggcct gcaggcatgc    11820
a                                                                    11821
```

<210> SEQ ID NO 23
<211> LENGTH: 10
<212> TYPE: DNA
<213> ORGANISM: Artificial Sequence
<220> FEATURE:
<223> OTHER INFORMATION: Synthetic Construct
<220> FEATURE:
<223> OTHER INFORMATION: Based on phage T4 td group I intron target site

<400> SEQUENCE: 23

```
gacccaagaa                                                           10
```

<210> SEQ ID NO 24
<211> LENGTH: 42
<212> TYPE: DNA
<213> ORGANISM: Artificial Sequence
<220> FEATURE:
<223> OTHER INFORMATION: Synthetic Construct
<220> FEATURE:
<223> OTHER INFORMATION: PCR primer ErmB-Pro-F3

<400> SEQUENCE: 24

```
ctacgcgtgg aaataagact tagaagcaaa cttaagagtg tg                       42
```

<210> SEQ ID NO 25
<211> LENGTH: 64
<212> TYPE: DNA
<213> ORGANISM: Artificial Sequence
<220> FEATURE:
<223> OTHER INFORMATION: Synthetic Construct
<220> FEATURE:
<223> OTHER INFORMATION: PCR primer ErmB-Pro-RA

<400> SEQUENCE: 25

```
cagaagcacc agcatctctt gggtccatgt aatcactcct tcttaattac aaattttag     60 catc                                                                 64
```

<210> SEQ ID NO 26
<211> LENGTH: 75
<212> TYPE: DNA
<213> ORGANISM: Artificial Sequence
<220> FEATURE:
<223> OTHER INFORMATION: Synthetic Construct

```
<220> FEATURE:
<223> OTHER INFORMATION: PCR primer linker1-ErmB-F1

<400> SEQUENCE: 26
acccaagaga tgctggtgct tctggtgctg gtatgaacaa aaatataaaa tattctcaaa        60 acttttttaac gagtg                                                        75

<210> SEQ ID NO 27
<211> LENGTH: 34
<212> TYPE: DNA
<213> ORGANISM: Artificial Sequence
<220> FEATURE:
<223> OTHER INFORMATION: Synthetic Construct
<220> FEATURE:
<223> OTHER INFORMATION: PCR primer ErmB-R1

<400> SEQUENCE: 27
gaacgcgtgc gactcataga attatttcct cccg                                    34

<210> SEQ ID NO 28
<211> LENGTH: 74
<212> TYPE: DNA
<213> ORGANISM: Artificial Sequence
<220> FEATURE:
<223> OTHER INFORMATION: Synthetic Construct
<220> FEATURE:
<223> OTHER INFORMATION: PCR primer ErmB-Pro-RB

<400> SEQUENCE: 28
ggggtaagat taacgacctt atctgaacat aatgccatgt aatcactcct tcttaattac        60 aaattttttag catc                                                         74

<210> SEQ ID NO 29
<211> LENGTH: 35
<212> TYPE: DNA
<213> ORGANISM: Artificial Sequence
<220> FEATURE:
<223> OTHER INFORMATION: Synthetic Construct
<220> FEATURE:
<223> OTHER INFORMATION: PCR primer tdGpI-F1

<400> SEQUENCE: 29
gcattatgtt cagataaggt cgttaatctt acccc                                   35

<210> SEQ ID NO 30
<211> LENGTH: 46
<212> TYPE: DNA
<213> ORGANISM: Artificial Sequence
<220> FEATURE:
<223> OTHER INFORMATION: Synthetic Construct
<220> FEATURE:
<223> OTHER INFORMATION: PCR primer tdGpI-R1

<400> SEQUENCE: 30
ccagaagcac cagcatctct tgggttaatt gaggcctgag tataag                       46

<210> SEQ ID NO 31
<211> LENGTH: 41
<212> TYPE: DNA
<213> ORGANISM: Artificial Sequence
<220> FEATURE:
<223> OTHER INFORMATION: Synthetic Construct
<220> FEATURE:
<223> OTHER INFORMATION: PCR primer Thio-F1

<400> SEQUENCE: 31
```

```
ctactagtac gcgttatatt gataaaaata ataatagtgg g                    41
```

<210> SEQ ID NO 32
<211> LENGTH: 52
<212> TYPE: DNA
<213> ORGANISM: Artificial Sequence
<220> FEATURE:
<223> OTHER INFORMATION: Synthetic Construct
<220> FEATURE:
<223> OTHER INFORMATION: PCR primer Thio-R-RAM

<400> SEQUENCE: 32

```
ccttatctga acataatgcc atatgaatcc ctcctaattt atacgttttc tc         52
```

<210> SEQ ID NO 33
<211> LENGTH: 31
<212> TYPE: DNA
<213> ORGANISM: Artificial Sequence
<220> FEATURE:
<223> OTHER INFORMATION: Synthetic Construct
<220> FEATURE:
<223> OTHER INFORMATION: PCR primer lacZ target-F

<400> SEQUENCE: 33

```
acgaattccg gataatgcga acagcgcacg g                               31
```

<210> SEQ ID NO 34
<211> LENGTH: 31
<212> TYPE: DNA
<213> ORGANISM: Artificial Sequence
<220> FEATURE:
<223> OTHER INFORMATION: Synthetic Construct
<220> FEATURE:
<223> OTHER INFORMATION: PCR primer lacZ target-R

<400> SEQUENCE: 34

```
tgcgatcgca ccgccgacgg cacgctgatt g                               31
```

<210> SEQ ID NO 35
<211> LENGTH: 45
<212> TYPE: DNA
<213> ORGANISM: Clostridium sporogenes

<400> SEQUENCE: 35

```
gctagatttg ataaagaatt tactgatgaa gatttagtgt tagca                45
```

<210> SEQ ID NO 36
<211> LENGTH: 45
<212> TYPE: DNA
<213> ORGANISM: Clostridium difficile

<400> SEQUENCE: 36

```
caacgtattg ctctagccct accttaaata tgtctacact atctt                45
```

<210> SEQ ID NO 37
<211> LENGTH: 45
<212> TYPE: DNA
<213> ORGANISM: Clostridium difficile

<400> SEQUENCE: 37

```
atccatctag atgtggcatt attacatcta gtattaataa gtccg                45
```

<210> SEQ ID NO 38
<211> LENGTH: 45
<212> TYPE: DNA
<213> ORGANISM: Clostridium sporogenes

```
<400> SEQUENCE: 38
aatagtatag atattactcc tatgccaagg gtaattgttt tgtct              45

<210> SEQ ID NO 39
<211> LENGTH: 45
<212> TYPE: DNA
<213> ORGANISM: Clostridium sporogenes

<400> SEQUENCE: 39 gtaatt

<223> OTHER INFORMATION: Synthetic Construct
<220> FEATURE:
<223> OTHER INFORMATION: PCR primer Csp-codY-417s-EBS1d

<400> SEQUENCE: 45
cagattgtac aaatgtggtg ataacagata agtcgatgaa gataacttac ctttctttgt    60

<210> SEQ ID NO 46
<211> LENGTH: 49
<212> TYPE: DNA
<213> ORGANISM: Artificial Sequence
<220> FEATURE:
<223> OTHER INFORMATION: Synthetic Construct
<220> FEATURE:
<223> OTHER INFORMATION: PCR primer Csp-codY-417s-EBS2

<400> SEQUENCE: 46
tgaacgcaag tttctaattt cggttgtaaa tcgatagagg aaagtgtct                49

<210> SEQ ID NO 47
<211> LENGTH: 53
<212> TYPE: DNA
<213> ORGANISM: Artificial Sequence
<220> FEATURE:
<223> OTHER INFORMATION: Synthetic Construct
<220> FEATURE:
<223> OTHER INFORMATION: PCR primer Cdi-pyrF-97a-IBS

<400> SEQUENCE: 47
aaaaaagctt ataattatcc ttactaccct aaatagtgcg cccagatagg gtg           53

<210> SEQ ID NO 48
<211> LENGTH: 60
<212> TYPE: DNA
<213> ORGANISM: Artificial Sequence
<220> FEATURE:
<223> OTHER INFORMATION: Synthetic Construct
<220> FEATURE:
<223> OTHER INFORMATION: PCR primer Cdi-pyrF-97a-EBS1d

<400> SEQUENCE: 48
cagattgtac aaatgtggtg ataacagata agtctaaata tgtaacttac ctttctttgt    60

<210> SEQ ID NO 49
<211> LENGTH: 49
<212> TYPE: DNA
<213> ORGANISM: Artificial Sequence
<220> FEATURE:
<223> OTHER INFORMATION: Synthetic Construct
<220> FEATURE:
<223> OTHER INFORMATION: PCR primer Cdi-pyrF-97a-EBS2

<400> SEQUENCE: 49
tgaacgcaag tttctaattt cggttggtag tcgatagagg aaagtgtct                49

<210> SEQ ID NO 50
<211> LENGTH: 53
<212> TYPE: DNA
<213> ORGANISM: Artificial Sequence
<220> FEATURE:
<223> OTHER INFORMATION: Synthetic Construct
<220> FEATURE:
<223> OTHER INFORMATION: PCR primer Cdi-spo0A-178a-IBS

<400> SEQUENCE: 50
aaaaaagctt ataattatcc ttattattcc atctagtgcg cccagatagg gtg           53

<210> SEQ ID NO 51
<211> LENGTH: 60
<212> TYPE: DNA
<213> ORGANISM: Artificial Sequence
<220> FEATURE:
<223> OTHER INFORMATION: Synthetic Construct
<220> FEATURE:
<223> OTHER INFORMATION: PCR primer Cdi-spo0A-178a-EBS1d

<400> SEQUENCE: 51
cagattgtac aaatgtggtg ataacagata agtccatcta gttaacttac ctttctttgt    60

<210> SEQ ID NO 52
<211> LENGTH: 49
<212> TYPE: DNA
<213> ORGANISM: Artificial Sequence
<220> FEATURE:
<223> OTHER INFORMATION: Synthetic Construct
<220> FEATURE:
<223> OTHER INFORMATION: PCR primer Cdi-spo0A-178a-EBS2

<400> SEQUENCE: 52
tgaacgcaag tttctaattt cggttaataa tcgatagagg aaagtgtct    49

<210> SEQ ID NO 53
<211> LENGTH: 53
<212> TYPE: DNA
<213> ORGANISM: Artificial Sequence
<220> FEATURE:
<223> OTHER INFORMATION: Synthetic Construct
<220> FEATURE:
<223> OTHER INFORMATION: PCR primer Csp-spo0A-249s-IBS

<400> SEQUENCE: 53
aaaaaagctt ataattatcc ttacctatcc caagggtgcg cccagatagg gtg    53

<210> SEQ ID NO 54
<211> LENGTH: 60
<212> TYPE: DNA
<213> ORGANISM: Artificial Sequence
<220> FEATURE:
<223> OTHER INFORMATION: Synthetic Construct
<220> FEATURE:
<223> OTHER INFORMATION: PCR primer Csp-spo0A-249s-EBS1d

<400> SEQUENCE: 54
cagattgtac aaatgtggtg ataacagata agtcccaagg gttaacttac ctttctttgt    60

<210> SEQ ID NO 55
<211> LENGTH: 49
<212> TYPE: DNA
<213> ORGANISM: Artificial Sequence
<220> FEATURE:
<223> OTHER INFORMATION: Synthetic Construct
<220> FEATURE:
<223> OTHER INFORMATION: PCR primer Csp-spo0A-249s-EBS2

<400> SEQUENCE: 55
tgaacgcaag tttctaattt cggttatagg tcgatagagg aaagtgtct    49

<210> SEQ ID NO 56
<211> LENGTH: 53
<212> TYPE: DNA
<213> ORGANISM: Artificial Sequence
<220> FEATURE:
<223> OTHER INFORMATION: PCR primer Csp-pyrF-595s-IBS

<400> SEQUENCE: 56

```
aaaaaagctt ataattatcc ttactatacg agcaggtgcg cccagatagg gtg          53
```

<210> SEQ ID NO 57
<211> LENGTH: 60
<212> TYPE: DNA
<213> ORGANISM: Artificial Sequence
<220> FEATURE:
<223> OTHER INFORMATION: Synthetic Construct
<220> FEATURE:
<223> OTHER INFORMATION: PCR primer Csp-pyrF-595s-EBS1d

<400> SEQUENCE: 57

```
cagattgtac aaatgtggtg ataacagata agtcgagcag tataacttac ctttctttgt    60
```

<210> SEQ ID NO 58
<211> LENGTH: 49
<212> TYPE: DNA
<213> ORGANISM: Artificial Sequence
<220> FEATURE:
<223> OTHER INFORMATION: Synthetic Construct
<220> FEATURE:
<223> OTHER INFORMATION: PCR primer Csp-pyrF-595s-EBS2

<400> SEQUENCE: 58

```
tgaacgcaag tttctaattt cggtttatag tcgatagagg aaagtgtct               49
```

<210> SEQ ID NO 59
<211> LENGTH: 53
<212> TYPE: DNA
<213> ORGANISM: Artificial Sequence
<220> FEATURE:
<223> OTHER INFORMATION: Synthetic Construct
<220> FEATURE:
<223> OTHER INFORMATION: PCR primer Cac-pyrF-345s-IBS

<400> SEQUENCE: 59

```
aaaaaagctt ataattatcc ttacacttcg aaggtgtgcg cccagatagg gtg          53
```

<210> SEQ ID NO 60
<211> LENGTH: 59
<212> TYPE: DNA
<213> ORGANISM: Artificial Sequence
<220> FEATURE:
<223> OTHER INFORMATION: Synthetic Construct
<220> FEATURE:
<223> OTHER INFORMATION: PCR primer Cac-pyrF-345s-EBS1d

<400> SEQUENCE: 60

```
cagattgtac aaatgtggtg ataacagata agtcgaaggt gataacttac ctttctttg    59
```

<210> SEQ ID NO 61
<211> LENGTH: 49
<212> TYPE: DNA
<213> ORGANISM: Artificial Sequence
<220> FEATURE:
<223> OTHER INFORMATION: Synthetic Construct
<220> FEATURE:
<223> OTHER INFORMATION: PCR primer Cac-pyrF-345s-EBS2

<400> SEQUENCE: 61

```
tgaacgcaag tttctaattt cggttaagtg tcgatagagg aaagtgtct               49
```

<210> SEQ ID NO 62
<211> LENGTH: 53
<212> TYPE: DNA
<213> ORGANISM: Artificial Sequence
<220> FEATURE:
<223> OTHER INFORMATION: Synthetic Construct
<220> FEATURE:
<223> OTHER INFORMATION: PCR primer Cac-spo0A-242a-IBS

<400> SEQUENCE: 62
aaaaaagctt ataattatcc ttaattatcc ttggagtgcg cccagatagg gtg        53

<210> SEQ ID NO 63
<211> LENGTH: 60
<212> TYPE: DNA
<213> ORGANISM: Artificial Sequence
<220> FEATURE:
<223> OTHER INFORMATION: Synthetic Construct
<220> FEATURE:
<223> OTHER INFORMATION: PCR primer Cac-spo0A-242a-EBS1d

<400> SEQUENCE: 63
cagattgtac aaatgtggtg ataacagata agtccttgga agtaacttac ctttctttgt   60

<210> SEQ ID NO 64
<211> LENGTH: 49
<212> TYPE: DNA
<213> ORGANISM: Artificial Sequence
<220> FEATURE:
<223> OTHER INFORMATION: Synthetic Construct
<220> FEATURE:
<223> OTHER INFORMATION: PCR primer Cac-spo0A-242a-EBS2

<400> SEQUENCE: 64
tgaacgcaag tttctaattt cggttataat ccgatagagg aaagtgtct        49

<210> SEQ ID NO 65
<211> LENGTH: 53
<212> TYPE: DNA
<213> ORGANISM: Artificial Sequence
<220> FEATURE:
<223> OTHER INFORMATION: Synthetic Construct
<220> FEATURE:
<223> OTHER INFORMATION: PCR primer Csp-SONO-492s-IBS

<400> SEQUENCE: 65
aaaaaagctt ataattatcc ttagaaagca aagatgtgcg cccagatagg gtg        53

<210> SEQ ID NO 66
<211> LENGTH: 60
<212> TYPE: DNA
<213> ORGANISM: Artificial Sequence
<220> FEATURE:
<223> OTHER INFORMATION: Synthetic Construct
<220> FEATURE:
<223> OTHER INFORMATION: PCR primer Csp-SONO-492s-EBS1d

<400> SEQUENCE: 66
cagattgtac aaatgtggtg ataacagata agtcaaagat gataacttac ctttctttgt   60

<210> SEQ ID NO 67
<211> LENGTH: 49
<212> TYPE: DNA
<213> ORGANISM: Artificial Sequence
<220> FEATURE:
<223> OTHER INFORMATION: Synthetic Construct
<220> FEATURE:
<223> OTHER INFORMATION: PCR primer Csp-SONO-492s-EBS2

<400> SEQUENCE: 67
tgaacgcaag tttctaattt cgattctttc tcgatagagg aaagtgtct        49

<210> SEQ ID NO 68

<210> SEQ ID NO 68
<211> LENGTH: 44
<212> TYPE: DNA
<213> ORGANISM: Artificial Sequence
<220> FEATURE:
<223> OTHER INFORMATION: Synthetic Construct
<220> FEATURE:
<223> OTHER INFORMATION: MCS1a oligonucleotide

<400> SEQUENCE: 68
ctcgaggtac catgcatagg cctgagctca ctagtgcggc cgcg                44

<210> SEQ ID NO 69
<211> LENGTH: 52
<212> TYPE: DNA
<213> ORGANISM: Artificial Sequence
<220> FEATURE:
<223> OTHER INFORMATION: Synthetic Construct
<220> FEATURE:
<223> OTHER INFORMATION: MCS1b oligonucleotide

<400> SEQUENCE: 69
aattcgcggc cgcactagtg agctcaggcc tatgcatggt acctcgagac gt        52

<210> SEQ ID NO 70
<211> LENGTH: 24
<212> TYPE: DNA
<213> ORGANISM: Artificial Sequence
<220> FEATURE:
<223> OTHER INFORMATION: Synthetic Construct
<220> FEATURE:
<223> OTHER INFORMATION: PCR primer lacI-P1

<400> SEQUENCE: 70
gtggtgcata tgaaaccagt aacg                                      24

<210> SEQ ID NO 71
<211> LENGTH: 30
<212> TYPE: DNA
<213> ORGANISM: Artificial Sequence
<220> FEATURE:
<223> OTHER INFORMATION: Synthetic Construct
<220> FEATURE:
<223> OTHER INFORMATION: PCR primer lacI-P2

<400> SEQUENCE: 71
gaattcctaa ctcacattaa ttgcgttgcg                                30

<210> SEQ ID NO 72
<211> LENGTH: 31
<212> TYPE: DNA
<213> ORGANISM: Artificial Sequence
<220> FEATURE:
<223> OTHER INFORMATION: Synthetic Construct
<220> FEATURE:
<223> OTHER INFORMATION: PCR primer ptb-P1

<400> SEQUENCE: 72
gaattcaggg aattaaaaga atgtttacct g                              31

<210> SEQ ID NO 73
<211> LENGTH: 37
<212> TYPE: DNA
<213> ORGANISM: Artificial Sequence
<220> FEATURE:
<223> OTHER INFORMATION: Synthetic Construct
<220> FEATURE:
<223> OTHER INFORMATION: PCR primer ptb-P2

<400> SEQUENCE: 73
actcatatgt tgcacctcta ctttaataat ttttaac 37

<210> SEQ ID NO 74
<211> LENGTH: 32
<212> TYPE: DNA
<213> ORGANISM: Artificial Sequence
<220> FEATURE:
<223> OTHER INFORMATION: Synthetic Construct
<220> FEATURE:
<223> OTHER INFORMATION: PCR primer CatPFwd

<400> SEQUENCE: 74
cagctgaccg gtctaaagag gtccctagcg cc 32

<210> SEQ ID NO 75
<211> LENGTH: 25
<212> TYPE: DNA
<213> ORGANISM: Artificial Sequence
<220> FEATURE:
<223> OTHER INFORMATION: Synthetic Construct
<220> FEATURE:
<223> OTHER INFORMATION: PCR primer CatPSOER

<400> SEQUENCE: 75
cggtcatgct gtaggtacaa ggtac 25

<210> SEQ ID NO 76
<211> LENGTH: 43
<212> TYPE: DNA
<213> ORGANISM: Artificial Sequence
<220> FEATURE:
<223> OTHER INFORMATION: Synthetic Construct
<220> FEATURE:
<223> OTHER INFORMATION: PCR primer CatPRev

<400> SEQUENCE: 76
cagctgaccg gtctctgaaa atataaaaac cacagattga tac 43

<210> SEQ ID NO 77
<211> LENGTH: 25
<212> TYPE: DNA
<213> ORGANISM: Artificial Sequence
<220> FEATURE:
<223> OTHER INFORMATION: Synthetic Construct
<220> FEATURE:
<223> OTHER INFORMATION: PCR primer CatPSOEF

<400> SEQUENCE: 77
gtaccttgta cctacagcat gaccg 25

<210> SEQ ID NO 78
<211> LENGTH: 41
<212> TYPE: DNA
<213> ORGANISM: Artificial Sequence
<220> FEATURE:
<223> OTHER INFORMATION: Synthetic Construct
<220> FEATURE:
<223> OTHER INFORMATION: PCR primer Thio-F1

<400> SEQUENCE: 78
ctactagtac gcgttatatt gataaaaata ataatagtgg g 41

<210> SEQ ID NO 79
<211> LENGTH: 52
<212> TYPE: DNA
<213> ORGANISM: Artificial Sequence
<220> FEATURE:

```
<223> OTHER INFORMATION: Synthetic Construct
<220> FEATURE:
<223> OTHER INFORMATION: PCR primer Thio-R-RAM

<400> SEQUENCE: 79
ccttatctga acataatgcc atatgaatcc ctcctaattt atacgttttc tc          52

<210> SEQ ID NO 80
<211> LENGTH: 20
<212> TYPE: DNA
<213> ORGANISM: Clostridium sporogenes

<400> SEQUENCE: 80
tatgccaagg gtaattgttt                                             20

<210> SEQ ID NO 81
<211> LENGTH: 20
<212> TYPE: DNA
<213> ORGANISM: Clostridium difficile

<400> SEQUENCE: 81
attacatcta gtattaataa                                             20

<210> SEQ ID NO 82
<211> LENGTH: 20
<212> TYPE: DNA
<213> ORGANISM: Clostridium acetobutylicum

<400> SEQUENCE: 82
tattcttgga aggttttctg                                             20

<210> SEQ ID NO 83
<211> LENGTH: 20
<212> TYPE: DNA
<213> ORGANISM: Clostridium sporogenes

<400> SEQUENCE: 83
ataggagcag tagttggatg                                             20

<210> SEQ ID NO 84
<211> LENGTH: 20
<212> TYPE: DNA
<213> ORGANISM: Clostridium difficile

<400> SEQUENCE: 84
accttaaata tgtctacact                                             20

<210> SEQ ID NO 85
<211> LENGTH: 20
<212> TYPE: DNA
<213> ORGANISM: Clostridium acetobutylicum

<400> SEQUENCE: 85
ctttgaaggt gattttgaag                                             20

<210> SEQ ID NO 86
<211> LENGTH: 20
<212> TYPE: DNA
<213> ORGANISM: Clostridium acetobutylicum

<400> SEQUENCE: 86
ttttaatgac atagtttata                                             20
```

```
<210> SEQ ID NO 87
<211> LENGTH: 20
<212> TYPE: DNA
<213> ORGANISM: Clostridium acetobutylicum

<400> SEQUENCE: 87
ctgaaattat ttcgttaata                                               20

<210> SEQ ID NO 88
<211> LENGTH: 20
<212> TYPE: DNA
<213> ORGANISM: Clostridium acetobutylicum

<400> SEQUENCE: 88
gtatctccag gcgcatatct                                               20

<210> SEQ ID NO 89
<211> LENGTH: 20
<212> TYPE: DNA
<213> ORGANISM: Clostridium acetobutylicum

<400> SEQUENCE: 89
tgtggagtat tcggtacaca                                               20

<210> SEQ ID NO 90
<211> LENGTH: 20
<212> TYPE: DNA
<213> ORGANISM: Clostridium difficile

<400> SEQUENCE: 90
ccaataagcc catctccaga                                               20

<210> SEQ ID NO 91
<211> LENGTH: 20
<212> TYPE: DNA
<213> ORGANISM: Clostridium difficile

<400> SEQUENCE: 91
ctctacaata tctatcttta                                               20

<210> SEQ ID NO 92
<211> LENGTH: 20
<212> TYPE: DNA
<213> ORGANISM: Clostridium difficile

<400> SEQUENCE: 92
gagggacagg ttgctgtagc                                               20

<210> SEQ ID NO 93
<211> LENGTH: 20
<212> TYPE: DNA
<213> ORGANISM: Clostridium botulinum

<400> SEQUENCE: 93
tttattattt tcttttttaa                                               20

<210> SEQ ID NO 94
<211> LENGTH: 20
<212> TYPE: DNA
<213> ORGANISM: Clostridium botulinum

<400> SEQUENCE: 94
gaattttatg ctaatatatc                                               20
```

<210> SEQ ID NO 95
<211> LENGTH: 20
<212> TYPE: DNA
<213> ORGANISM: Clostridium botulinum

<400> SEQUENCE: 95
tttaacatat agattagtta                                             20

<210> SEQ ID NO 96
<211> LENGTH: 20
<212> TYPE: DNA
<213> ORGANISM: Clostridium botulinum

<400> SEQUENCE: 96
tatgccaagg gtaattgttt                                             20

<210> SEQ ID NO 97
<211> LENGTH: 53
<212> TYPE: DNA
<213> ORGANISM: Artificial Sequence
<220> FEATURE:
<223> OTHER INFORMATION: Synthetic Construct
<220> FEATURE:
<223> OTHER INFORMATION: PCR primer Cdi-CD0552-75a-IBS

<400> SEQUENCE: 97
aaaaaagctt ataattatcc ttattctcca caatagtgcg cccagatagg gtg        53

<210> SEQ ID NO 98
<211> LENGTH: 60
<212> TYPE: DNA
<213> ORGANISM: Artificial Sequence
<220> FEATURE:
<223> OTHER INFORMATION: Synthetic Construct
<220> FEATURE:
<223> OTHER INFORMATION: PCR primer Cdi-CD0552-75a-EBS1d

<400> SEQUENCE: 98
cagattgtac aaatgtggtg ataacagata agtcacaata tctaacttac ctttctttgt 60

<210> SEQ ID NO 99
<211> LENGTH: 49
<212> TYPE: DNA
<213> ORGANISM: Artificial Sequence
<220> FEATURE:
<223> OTHER INFORMATION: Synthetic Construct
<220> FEATURE:
<223> OTHER INFORMATION: PCR primer Cdi-CD0552-75a-EBS2

<400> SEQUENCE: 99
tgaacgcaag tttctaattt cggttgagaa tcgatagagg aaagtgtct             49

<210> SEQ ID NO 100
<211> LENGTH: 53
<212> TYPE: DNA
<213> ORGANISM: Artificial Sequence
<220> FEATURE:
<223> OTHER INFORMATION: Synthetic Construct
<220> FEATURE:
<223> OTHER INFORMATION: PCR primer Cdi-CD3563-226s-IBS

<400> SEQUENCE: 100
aaaaaagctt ataattatcc ttaatgagcg acagggtgcg cccagatagg gtg        53

<210> SEQ ID NO 101
<211> LENGTH: 60

```
<212> TYPE: DNA
<213> ORGANISM: Artificial Sequence
<220> FEATURE:
<223> OTHER INFORMATION: Synthetic Construct
<220> FEATURE:
<223> OTHER INFORMATION: PCR primer Cdi-CD3563-226s-EBS1d

<400> SEQUENCE: 101
cagattgtac aaatgtggtg ataacagata agtcgacagg tttaacttac ctttctttgt    60

<210> SEQ ID NO 102
<211> LENGTH: 49
<212> TYPE: DNA
<213> ORGANISM: Artificial Sequence
<220> FEATURE:
<223> OTHER INFORMATION: Synthetic Construct
<220> FEATURE:
<223> OTHER INFORMATION: PCR primer Cdi-CD3563-226s-EBS2

<400> SEQUENCE: 102
tgaacgcaag tttctaattt cggttctcat ccgatagagg aaagtgtct                49

<210> SEQ ID NO 103
<211> LENGTH: 53
<212> TYPE: DNA
<213> ORGANISM: Artificial Sequence
<220> FEATURE:
<223> OTHER INFORMATION: Synthetic Construct
<220> FEATURE:
<223> OTHER INFORMATION: PCR primer Cac-CAC0081-141a-IBS

<400> SEQUENCE: 103
aaaaaagctt ataattatcc ttaattttca atgacgtgcg cccagatagg gtg           53

<210> SEQ ID NO 104
<211> LENGTH: 60
<212> TYPE: DNA
<213> ORGANISM: Artificial Sequence
<220> FEATURE:
<223> OTHER INFORMATION: Synthetic Construct
<220> FEATURE:
<223> OTHER INFORMATION: PCR primer Cac-CAC0081-141a-EBS1d

<400> SEQUENCE: 104
cagattgtac aaatgtggtg ataacagata agtcaatgac attaacttac ctttctttgt    60

<210> SEQ ID NO 105
<211> LENGTH: 49
<212> TYPE: DNA
<213> ORGANISM: Artificial Sequence
<220> FEATURE:
<223> OTHER INFORMATION: Synthetic Construct
<220> FEATURE:
<223> OTHER INFORMATION: PCR primer Cac-CAC0081-141a-EBS2

<400> SEQUENCE: 105
tgaacgcaag tttctaattt cggttaaaat ccgatagagg aaagtgtct                49

<210> SEQ ID NO 106
<211> LENGTH: 53
<212> TYPE: DNA
<213> ORGANISM: Artificial Sequence
<220> FEATURE:
<223> OTHER INFORMATION: Synthetic Construct
<220> FEATURE:
<223> OTHER INFORMATION: PCR primer Cac-CAC0078-385a-IBS

<400> SEQUENCE: 106
```

```
aaaaaagctt ataattatcc ttactgtacc tccaggtgcg cccagatagg gtg          53
```

<210> SEQ ID NO 107
<211> LENGTH: 60
<212> TYPE: DNA
<213> ORGANISM: Artificial Sequence
<220> FEATURE:
<223> OTHER INFORMATION: Synthetic Construct
<220> FEATURE:
<223> OTHER INFORMATION: PCR primer Cac-CAC0078-385a-EBS1d

<400> SEQUENCE: 107

```
cagattgtac aaatgtggtg ataacagata agtcctccag gctaacttac ctttctttgt   60
```

<210> SEQ ID NO 108
<211> LENGTH: 49
<212> TYPE: DNA
<213> ORGANISM: Artificial Sequence
<220> FEATURE:
<223> OTHER INFORMATION: Synthetic Construct
<220> FEATURE:
<223> OTHER INFORMATION: PCR primer Cac-CAC0078-385a-EBS2

<400> SEQUENCE: 108

```
tgaacgcaag tttctaattt cgatttacag tcgatagagg aaagtgtct               49
```

<210> SEQ ID NO 109
<211> LENGTH: 53
<212> TYPE: DNA
<213> ORGANISM: Artificial Sequence
<220> FEATURE:
<223> OTHER INFORMATION: Synthetic Construct
<220> FEATURE:
<223> OTHER INFORMATION: PCR primer Cac-CAC0080-121s-IBS

<400> SEQUENCE: 109

```
aaaaaagctt ataattatcc ttaaactgca attatgtgcg cccagatagg gtg          53
```

<210> SEQ ID NO 110
<211> LENGTH: 60
<212> TYPE: DNA
<213> ORGANISM: Artificial Sequence
<220> FEATURE:
<223> OTHER INFORMATION: Synthetic Construct
<220> FEATURE:
<223> OTHER INFORMATION: PCR primer Cac-CAC0080-121s-EBS1d

<400> SEQUENCE: 110

```
cagattgtac aaatgtggtg ataacagata agtcaattat tttaacttac ctttctttgt   60
```

<210> SEQ ID NO 111
<211> LENGTH: 49
<212> TYPE: DNA
<213> ORGANISM: Artificial Sequence
<220> FEATURE:
<223> OTHER INFORMATION: Synthetic Construct
<220> FEATURE:
<223> OTHER INFORMATION: PCR primer Cac-CAC0080-121s-EBS2

<400> SEQUENCE: 111

```
tgaacgcaag tttctaattt cggttcagtt ccgatagagg aaagtgtct               49
```

<210> SEQ ID NO 112
<211> LENGTH: 53
<212> TYPE: DNA
<213> ORGANISM: Artificial Sequence
<220> FEATURE:
<223> OTHER INFORMATION: Synthetic Construct

```
<220> FEATURE:
<223> OTHER INFORMATION: PCR primer Cac-CAC2208-201s-IBS

<400> SEQUENCE: 112
aaaaaagctt ataattatcc ttacatgtcg agtatgtgcg cccagatagg gtg          53

<210> SEQ ID NO 113
<211> LENGTH: 60
<212> TYPE: DNA
<213> ORGANISM: Artificial Sequence
<220> FEATURE:
<223> OTHER INFORMATION: Synthetic Construct
<220> FEATURE:
<223> OTHER INFORMATION: PCR primer Cac-CAC2208-201s-EBS1d

<400> SEQUENCE: 113
cagattgtac aaatgtggtg ataacagata agtcgagtat tctaacttac ctttctttgt   60

<210> SEQ ID NO 114
<211> LENGTH: 49
<212> TYPE: DNA
<213> ORGANISM: Artificial Sequence
<220> FEATURE:
<223> OTHER INFORMATION: Synthetic Construct
<220> FEATURE:
<223> OTHER INFORMATION: PCR primer Cac-CAC2208-201s-EBS2

<400> SEQUENCE: 114
tgaacgcaag tttctaattt cggttacatg tcgatagagg aaagtgtct              49

<210> SEQ ID NO 115
<211> LENGTH: 53
<212> TYPE: DNA
<213> ORGANISM: Artificial Sequence
<220> FEATURE:
<223> OTHER INFORMATION: Synthetic Construct
<220> FEATURE:
<223> OTHER INFORMATION: PCR primer Cdi-CD0153-784a-IBS

<400> SEQUENCE: 115
aaaaaagctt ataattatcc ttataccact aagccgtgcg cccagatagg gtg          53

<210> SEQ ID NO 116
<211> LENGTH: 60
<212> TYPE: DNA
<213> ORGANISM: Artificial Sequence
<220> FEATURE:
<223> OTHER INFORMATION: Synthetic Construct
<220> FEATURE:
<223> OTHER INFORMATION: PCR primer Cdi-CD0153-784a-EBS1d

<400> SEQUENCE: 116
cagattgtac aaatgtggtg ataacagata agtctaagcc cataacttac ctttctttgt  60

<210> SEQ ID NO 117
<211> LENGTH: 49
<212> TYPE: DNA
<213> ORGANISM: Artificial Sequence
<220> FEATURE:
<223> OTHER INFORMATION: Synthetic Construct
<220> FEATURE:
<223> OTHER INFORMATION: PCR primer Cdi-CD0153-784a-EBS2

<400> SEQUENCE: 117
tgaacgcaag tttctaattt cggtttggta tcgatagagg aaagtgtct              49

<210> SEQ ID NO 118
```

<211> LENGTH: 53
<212> TYPE: DNA
<213> ORGANISM: Artificial Sequence
<220> FEATURE:
<223> OTHER INFORMATION: Synthetic Construct
<220> FEATURE:
<223> OTHER INFORMATION: PCR primer Cbo-CBO0780-671a-IBS1

<400> SEQUENCE: 118
aaaaaagctt ataattatcc ttagctttct tatttgtgcg cccagatagg gtg         53

<210> SEQ ID NO 119
<211> LENGTH: 60
<212> TYPE: DNA
<213> ORGANISM: Artificial Sequence
<220> FEATURE:
<223> OTHER INFORMATION: Synthetic Construct
<220> FEATURE:
<223> OTHER INFORMATION: PCR primer Cbo-CBO0780-671a-EBS1d

<400> SEQUENCE: 119
cagattgtac aaatgtggtg ataacagata agtcttattt tctaacttac ctttctttgt    60

<210> SEQ ID NO 120
<211> LENGTH: 49
<212> TYPE: DNA
<213> ORGANISM: Artificial Sequence
<220> FEATURE:
<223> OTHER INFORMATION: Synthetic Construct
<220> FEATURE:
<223> OTHER INFORMATION: PCR primer Cbo-CBO0780-671a-EBS2

<400> SEQUENCE: 120
tgaacgcaag tttctaattt cgattaaagc tcgatagagg aaagtgtct              49

<210> SEQ ID NO 121
<211> LENGTH: 53
<212> TYPE: DNA
<213> ORGANISM: Artificial Sequence
<220> FEATURE:
<223> OTHER INFORMATION: Synthetic Construct
<220> FEATURE:
<223> OTHER INFORMATION: PCR primer Cbo-CBO1120-670s-IBS1

<400> SEQUENCE: 121
aaaaaagctt ataattatcc ttactgaact ttatggtgcg cccagatagg gtg         53

<210> SEQ ID NO 122
<211> LENGTH: 60
<212> TYPE: DNA
<213> ORGANISM: Artificial Sequence
<220> FEATURE:
<223> OTHER INFORMATION: Synthetic Construct
<220> FEATURE:
<223> OTHER INFORMATION: PCR primer Cbo-CBO1120-670s-EBS1d

<400> SEQUENCE: 122
cagattgtac aaatgtggtg ataacagata agtctttatg cttaacttac ctttctttgt    60

<210> SEQ ID NO 123
<211> LENGTH: 49
<212> TYPE: DNA
<213> ORGANISM: Artificial Sequence
<220> FEATURE:
<223> OTHER INFORMATION: Synthetic Construct
<220> FEATURE:
<223> OTHER INFORMATION: PCR primer Cbo-CBO1120-670s-EBS2

<400> SEQUENCE: 123
tgaacgcaag tttctaattt cggttttcag tcgatagagg aaagtgtct         49

<210> SEQ ID NO 124
<211> LENGTH: 53
<212> TYPE: DNA
<213> ORGANISM: Artificial Sequence
<220> FEATURE:
<223> OTHER INFORMATION: Synthetic Construct
<220> FEATURE:
<223> OTHER INFORMATION: PCR primer Cbo-CBO2762-1014s-IBS1

<400> SEQUENCE: 124
aaaaaagctt ataattatcc ttagatttca catatgtgcg cccagatagg gtg         53

<210> SEQ ID NO 125
<211> LENGTH: 60
<212> TYPE: DNA
<213> ORGANISM: Artificial Sequence
<220> FEATURE:
<223> OTHER INFORMATION: Synthetic Construct
<220> FEATURE:
<223> OTHER INFORMATION: PCR primer Cbo-CBO2762-1014s-EBS1d

<400> SEQUENCE: 125
cagattgtac aaatgtggtg ataacagata agtcacatat agtaacttac ctttctttgt         60

<210> SEQ ID NO 126
<211> LENGTH: 49
<212> TYPE: DNA
<213> ORGANISM: Artificial Sequence
<220> FEATURE:
<223> OTHER INFORMATION: Synthetic Construct
<220> FEATURE:
<223> OTHER INFORMATION: PCR primer Cbo-CBO2762-1014s-EBS2

<400> SEQUENCE: 126
tgaacgcaag tttctaattt cgattaaatc tcgatagagg aaagtgtct         49

<210> SEQ ID NO 127
<211> LENGTH: 53
<212> TYPE: DNA
<213> ORGANISM: Artificial Sequence
<220> FEATURE:
<223> OTHER INFORMATION: Synthetic Construct
<220> FEATURE:
<223> OTHER INFORMATION: PCR primer Cbo-spo0A-249s-IBS1

<400> SEQUENCE: 127
aaaaaagctt ataattatcc ttacctatcc caagggtgcg cccagatagg gtg         53

<210> SEQ ID NO 128
<211> LENGTH: 60
<212> TYPE: DNA
<213> ORGANISM: Artificial Sequence
<220> FEATURE:
<223> OTHER INFORMATION: Synthetic Construct
<220> FEATURE:
<223> OTHER INFORMATION: PCR primer Cbo-spo0A-249s-EBS1d

<400> SEQUENCE: 128
cagattgtac aaatgtggtg ataacagata agtcccaagg gttaacttac ctttctttgt         60

<210> SEQ ID NO 129
<211> LENGTH: 49
<212> TYPE: DNA
<213> ORGANISM: Artificial Sequence
<220> FEATURE:

```
<223> OTHER INFORMATION: Synthetic Construct
<220> FEATURE:
<223> OTHER INFORMATION: PCR primer Cbo-spo0A-249s-EBS2

<400> SEQUENCE: 129
tgaacgcaag tttctaattt cggttatagg tcgatagagg aaagtgtct            49

<210> SEQ ID NO 130
<211> LENGTH: 88
<212> TYPE: DNA
<213> ORGANISM: Artificial Sequence
<220> FEATURE:
<223> OTHER INFORMATION: Synthetic Construct
<220> FEATURE:
<223> OTHER INFORMATION: PCR primer linker-catP-F

<400> SEQUENCE: 130
atactcaggc tcaattaac ccaagagatg ctggtgcttc tggtgctggt atggtatttg    60
aaaaaattga taaaaatagt tggaacag                                     88

<210> SEQ ID NO 131
<211> LENGTH: 49
<212> TYPE: DNA
<213> ORGANISM: Artificial Sequence
<220> FEATURE:
<223> OTHER INFORMATION: Synthetic Construct
<220> FEATURE:
<223> OTHER INFORMATION: PCR primer catP-MluI-R1

<400> SEQUENCE: 131
atacgcgttt aactatttat caattcctgc aattcgttta caaaacggc             49

<210> SEQ ID NO 132
<211> LENGTH: 44
<212> TYPE: DNA
<213> ORGANISM: Artificial Sequence
<220> FEATURE:
<223> OTHER INFORMATION: Synthetic Construct

<400> SEQUENCE: 132
ctcgaggtac catgcatagg cctgagctca ctagtgcggc cgcg                  44
```